United States Patent
Ibrahim et al.

(10) Patent No.: US 10,130,691 B2
(45) Date of Patent: Nov. 20, 2018

(54) COMPOSITIONS AND METHODS FOR TREATING FUNGAL AND BACTERIAL PATHOGENS

(71) Applicants: Los Angeles Biomedical Research Institute at Harbor-UCLA Medical Center, Torrance, CA (US); NovaDigm Therapeutics, Inc., Grand Forks, ND (US)

(72) Inventors: Ashraf S. Ibrahim, Irvine, CA (US); Michael R. Yeaman, Redondo Beach, CA (US); Scott G. Filler, Rancho Palos Verdes, CA (US); John E. Edwards, Jr., Palos Verdes Estates, CA (US); John P. Hennessey, Jr., Lower Gwynedd, PA (US)

(73) Assignees: Los Angeles Biomedical Research Institute at Harbor-UCLA Medical Center, Torrance, CA (US); NovaDigm Therapeutics, Inc., Grand Forks, ND (US)

( * ) Notice: Subject to any disclaimer, the term of this patent is extended or adjusted under 35 U.S.C. 154(b) by 0 days.

(21) Appl. No.: 14/774,557

(22) PCT Filed: Mar. 14, 2014

(86) PCT No.: PCT/US2014/028521
§ 371 (c)(1),
(2) Date: Sep. 10, 2015

(87) PCT Pub. No.: WO2014/144211
PCT Pub. Date: Sep. 18, 2014

(65) Prior Publication Data
US 2016/0030534 A1    Feb. 4, 2016

Related U.S. Application Data

(60) Provisional application No. 61/789,091, filed on Mar. 15, 2013.

(51) Int. Cl.
| | | |
|---|---|---|
| A61K 39/00 | (2006.01) | |
| C07K 16/14 | (2006.01) | |
| A61K 39/39 | (2006.01) | |
| C07K 14/40 | (2006.01) | |

(52) U.S. Cl.
CPC .......... *A61K 39/0002* (2013.01); *A61K 39/39* (2013.01); *C07K 14/40* (2013.01); *C07K 16/14* (2013.01); *A61K 2039/54* (2013.01); *A61K 2039/55505* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,346,074 A | 8/1982 | Gilmour et al. | |
| 5,578,309 A | 11/1996 | Cutler et al. | |
| 5,622,939 A | 4/1997 | Jamas et al. | |
| 5,668,263 A | 9/1997 | Hoyer et al. | |
| 5,817,466 A | 10/1998 | Hoyer et al. | |
| 5,961,970 A | 10/1999 | Lowell et al. | |
| 6,248,329 B1 | 6/2001 | Chandrashekar et al. | |
| 6,703,025 B1 | 3/2004 | Patti et al. | |
| 6,747,137 B1 | 6/2004 | Weinstock et al. | |
| 7,067,138 B1 | 6/2006 | Edwards, Jr. et al. | |
| 7,241,613 B1 | 7/2007 | Willins et al. | |
| 7,250,286 B2 | 7/2007 | Ellison | |
| 7,666,438 B1 | 2/2010 | Patti et al. | |
| 7,732,187 B2 | 6/2010 | Cochran et al. | |
| 8,541,008 B2 | 9/2013 | Edwards, Jr. et al. | |
| 8,709,446 B2 | 4/2014 | Fu et al. | |
| 2002/0102262 A1 | 8/2002 | Hook et al. | |
| 2002/0146435 A1 | 10/2002 | Evans et al. | |
| 2003/0124134 A1 | 7/2003 | Edwards et al. | |
| 2003/0217373 A1 | 11/2003 | Green et al. | |
| 2004/0116380 A1 | 6/2004 | Jamas et al. | |
| 2004/0175731 A1 | 9/2004 | Pier et al. | |
| 2005/0287146 A1 | 12/2005 | Patti et al. | |
| 2006/0083750 A1 | 4/2006 | Edwards et al. | |
| 2007/0027309 A1 | 2/2007 | Weinstock et al. | |
| 2007/0077256 A1 | 4/2007 | Edwards et al. | |
| 2008/0311135 A1 | 12/2008 | Zheng et al. | |
| 2009/0297562 A1 | 12/2009 | Edwards et al. | |
| 2010/0015182 A1 | 1/2010 | Lang et al. | |
| 2010/0150942 A1 | 6/2010 | Cantor | |
| 2010/0150956 A1 | 6/2010 | Patti et al. | |
| 2012/0014995 A1 | 1/2012 | Edwards, Jr. et al. | |
| 2012/0107316 A1 | 5/2012 | Cassone et al. | |
| 2012/0237534 A1 | 9/2012 | Fu et al. | |
| 2014/0037689 A1 | 2/2014 | Edwards, Jr. et al. | |
| 2014/0127217 A1 | 5/2014 | Edwards, Jr. et al. | |
| 2014/0127218 A1 | 5/2014 | Edwards, Jr. et al. | |
| 2014/0127243 A1 | 5/2014 | Edwards, Jr. et al. | |
| 2014/0335114 A1 | 11/2014 | Fu et al. | |
| 2015/0191514 A1 | 7/2015 | Ibrahim et al. | |

FOREIGN PATENT DOCUMENTS

| | | |
|---|---|---|
| EP | 2428800 A1 | 3/2012 |
| JP | 2007-512312 A | 5/2007 |
| JP | 2008540453 A | 11/2008 |
| JP | 2009524601 A | 7/2009 |
| JP | 2012-530786 A | 12/2012 |
| WO | WO-2005/049081 A1 | 6/2005 |
| WO | WO-2006/036817 A2 | 4/2006 |
| WO | WO-2006/059228 A2 | 6/2006 |
| WO | WO-2006/121895 A2 | 11/2006 |
| WO | WO-2007/081896 A2 | 7/2007 |

(Continued)

OTHER PUBLICATIONS

Bowie et al (Science, 1990, 257:1306-1310).*

(Continued)

*Primary Examiner* — Robert A Zeman
(74) *Attorney, Agent, or Firm* — Clark & Elbing LLP

(57) ABSTRACT

The invention features fragments of the *Candida* cell surface proteins Als3 and Hyr1 and combinations thereof useful in immunizing a subject against fungal or bacterial infections or both.

12 Claims, No Drawings
Specification includes a Sequence Listing.

(56) References Cited

FOREIGN PATENT DOCUMENTS

| WO | WO-2007/126813 A2 | 11/2007 |
|---|---|---|
| WO | WO-2010/151544 A1 | 12/2010 |
| WO | WO-2011/003085 A1 | 1/2011 |
| WO | WO-2012/163533 A1 | 12/2012 |
| WO | WO-2013/015831 A1 | 1/2013 |
| WO | WO-2014/144024 A1 | 9/2014 |
| WO | WO-2014/144211 A2 | 9/2014 |
| WO | WO-2014/144222 A2 | 9/2014 |
| WO | WO-2016/142660 A1 | 9/2016 |
| WO | WO-2017/155949 A1 | 9/2017 |

OTHER PUBLICATIONS

Greenspan et al. (Nature Biotechnology 7: 936-937, 1999).*
Colman (Res. Immunology, Jan. 1994, vol. 145, pp. 33-36).*
Bork (Genome Research, 2000,10:398-400).*
Bailey et al., "The Candida albicans HYR1 gene, which is activated in response to hyphal development, belongs to a gene family encoding yeast cell wall proteins," J Bacteriol. 178(18):5353-60 (1996).
Bates et al., "Candida albicans Iff11, a secreted protein required for cell wall structure and virulence," Infect Immun. 75(6):2922-8 (2007).
Database Geneseq. "Candida albicans protein, SEQ ID No. 15577," retrieved from EBI Accession No. GSP:ATC95389 on Oct. 30, 2008.
Database Geneseq. "C. albicans hyphally regulated protein, SEQ ID No. 326," retrieved from EBI Accession No. GSP:AJF41554 on Nov. 1, 2007.
Barki et al., "Isolation of a Candida albicans DNA sequence conferring adhesion and aggregation on *Saccharomyces cerevisiae*," J Bacteriol. 175(17):5683-9 (1993).
Bendel et al., "Distinct mechanisms of epithelial adhesion for Candida albicans and Candida tropicalis. Identification of the participating ligands and development of inhibitory peptides," J Clin Invest. 92(4):1840-9 (1993).
Caesar-TonThat et al., "A monoclonal antibody to Candida albicans enhances mouse neutrophil candidacidal activity," Infect Immun. 65(12):5354-7 (1997).
Campbell, General properties and applications of monoclonal antibodies. *Monoclonal Antibody Technology*. Elsevier Science Publishers, 1-32 (1984).
Castaldo et al., "Clinical spectrum of fungal infections after orthotopic liver transplantation," Arch Surg. 126(2):149-56 (1991).
Cheng et al, "Comparison between Candida albicans agglutinin-like sequence gene expression patterns in human clinical specimens and models of vaginal candidiasis," Infect Immun. 73(3):1656-63 (2005).
Choi et al., "Acinetobacter baumannii invades epithelial cells and outer membrane protein A mediates interactions with epithelial cells," BMC Microbiol. 8:216 (2008) (11 pages).
Coleman et al., "Monoclonal antibodies specific for Candida albicans Als3 that immunolabel fungal cells in vitro and in vivo and block adhesion to host surfaces," J Microbiol Methods. 78(1):71-8 (2009) (19 pages).
Cormack et al., "An adhesion of the yeast pathogen Candida glabrata mediating adherence to human epithelial cells," Science. 285(5427):578-82 (1999).
Cutler et al., "Characteristics of Candida albicans adherence to mouse tissues," Infect Immun. 58(6):1902-8 (1990).
De Bernardis et al., "Protective role of antimannan and anti-aspartyl proteinase antibodies in an experimental model of Candida albicans vaginitis in rats," Infect Immun. 65(8):3399-405 (1997).
Dromer et al., "Protection of mice against experimental cryptococcosis by anti-Cryptococcus neoformans monoclonal antibody," Infect Immun. 55(3):749-52 (1987).
Ekenna et al., "Natural history of bloodstream infections in a burn patient population: the importance of candidemia," Am J Infect Control. 21(4):189-95 (1993).

Ellis, New technologies for making vaccines. *Vaccines*. Plotkin and Mortimer, 568-575 (1988).
Filler, "Candida-host cell receptor-ligand interactions," Curr Opin Microbiol. 9(4):333-9 (2006).
Fisher-Hoch et al., "Opportunistic candidiasis: an epidemic of the 1980's," Clin Infect Dis. 21(4):897-904 (1995).
Fonzi et al., "Isogenic strain construction and gene mapping in Candida albicans," Genetics. 134(3):717-28 (1993).
Fu et al., "Candida albicans Als1p: an adhesin that is a downstream effector of the EFG1 filamentation pathway," Mol Microbiol. 44(1):61-72 (2002).
Fu et al., "Cloning and characterization of a gene (LIP1) which encodes a lipase from the pathogenic yeast *Candida albicans*," Microbiology. 143(Pt 2):331-40 (1997).
Fu et al., "Cloning and characterization of CAD1/AAF1, a gene from Candida albicans that induces adherence to endothelial cells after expression in *Saccharomyces cerevisiae*," Infect Immun. 66(5):2078-84 (1998).
Fu et al., "Expression of the Candida albicans Gene ALS1 in *Saccharomyces cerevisiae* Induces Adherence to Endothelial and Epithelial Cells," Infect Immun. 66(4):1783-6 (1998).
Gale et al., "Cloning and expression of a gene encoding an integrin-like protein in Candida albicans," Proc Nat Acad Sci USA. 93(1):357-61 (1996).
Gale et al., "Linkage of adhesion, filamentous growth, and virulence in Candida albicans to a single gene, INT1," Science. 279(5355):1355-8 (1998).
Gaur et al., "Expression, cloning, and characterization of a Candida albicans gene, ALA1, that confers adherence properties upon *Saccharomyces cerevisiae* for extracellular matrix proteins," Infect Immun. 65(12):5289-94 (1997).
Gietz et al., "Studies on the transformation of intact yeast cells by the LiAc/SS-DNA/PEG procedure," Yeast. 11(4):355-60 (1995).
Greenspan et al., "Defining epitopes: It's not as easy as it seems," Nat Biotechnol. 17(10):936-7 (1999).
Gustafson et al., "Molecular mimicry in Candida albicans. Role of an integrin analogue in adhesion of the yeast to human endothelium," J Clin Invest. 87(6):1896-902 (1991).
Han et al., "Antibody response that protects against disseminated candidiasis," Infect Immun. 63(7):2714-9 (1995).
Hasenclever et al., "Antigenic relationships of Torulopsis glabrata and seven species of the genus *Candida*," J Bacteriol. 79:677-81 (1960).
Hoyer et al., "Candida albicans ALS1: domains related to a *Saccharomyces cerevisiae* sexual agglutinin separated by a repeating motif," Mol Microbiol. 15(1):39-54 (1995).
Hoyer et al., "Candida albicans ALS3 and insights into the nature of the ALS gene family," Curr Genet. 33(6):451-9 (1998).
Hoyer et al., "Characterization of agglutinin-like sequence genes from non-albicans Candida and phylogenetic analysis of the ALS family," Genetics. 157(4):1555-67 (2001).
Hoyer et al., "Detection of Als proteins on the cell wall of Candida albicans in murine tissues," Infect Immun. 67(8):4251-55 (1999).
Hoyer et al., "Identification of Candida albicans ALS2 and ALS4 and localization of als proteins to the fungal cell surface," J Bacteriol. 180(20):5334-43 (1998).
Hoyer, "The ALS gene family of Candida albicans," Trends Microbiol. 9(4):176-80 (2001).
Ibrahim et al., "Evidence implicating phospholipase as a virulence factor of Candida albicans," Infect Immun. 63(5):1993-8 (1995).
Ibrahim et al., "The anti-Candida vaccine based on the recombinant N-terminal domain of Als1p is broadly active against disseminated candidiasis," Infect Immun. 74(5):3039-41 (2006).
Ibrahim et al., "Vaccination with recombinant N-terminal domain of Als1p improves survival during murine disseminated candidiasis by enhancing cell-mediated, not humoral, immunity," Infect Immun. 73(2):999-1005 (2005).
Illustrated Stedman's Medical Dictionary, 24th Edition. Williams and Wilkins, London. p. 707 (1982).
Inhibitex reports favorable results from aurexis phase II trial for the treatment of staph bloodstream infections. Inhibitex Inc. (2005) (Accessed Sep. 19, 2005) (5 pages).

(56) References Cited

OTHER PUBLICATIONS

Jaffe et al., "Culture of human endothelial cells derived from umbilical veins. Identification by morphologic and immunologic criteria," J Clin Invest. 52(11):2745-56 (1973).
Jarvis et al., "Predominant pathogens in hospital infections," J Antimicrob Chemother. 29 (Suppl A): 19-24 (1992) (Abstract only) (2 pages).
Jimenez-Lucho et al., "Cryptococcus neoformans, Candida albicans, and other fungi bind specifically to the glycosphingolipid lactosylceramide (Gal beta 1-4Glc beta 1-1 Cer), a possible adhesion receptor for yeasts," Infect Immun. 58(7):2085-90 (1990).
Kim et al., "Partial characterization of leukocyte binding molecules on endothelial cells induced by minimally oxidized LDL," Arterioscler Thromb. 14(3):427-33 (1994).
Klein, "Role of cell surface molecules of Blastomyces dermatitidis in the pathogenesis and immunobiology of blastomycosis," Semin Respir Infect. 12(3):198-205 (1997).
Klotz et al., "Effect of an arginine-glycine-aspartic acid-containing peptide on hematogenous candidal infections in rabbits," Antimicrob Agents Chemother. 36(1):132-6 (1992).
Kramer et al., "How long do nosocomial pathogens persist on inanimate surfaces? A systematic review," BMC Infect Dis. 6:130 (2006) (8 pages).
Lipke et al., "AG alpha 1 is the structural gene for the *Saccharomyces cerevisiae* alpha-agglutinin, a cell surface glycoprotein involved in cell-cell interactions during mating," Mol Cell Biol. 9(8):3155-65 (1989).
Liu et al., "INH-A21 contains antibodies specific for the Candida ALS protein family," 44th ICAAC Abstracts, Oct. 30-Nov. 2, Washington D.C.. p. 425, M-1144 (2004).
Lotter et al., "Identification of an epitope on the Entamoeba histolytica 170-kD lectin conferring antibody-mediated protection against invasive amebiasis," J Exp Med. 185(10):1793-801 (1997).
Loza et al., "Functional Analysis of the Candida albicans ALS1 Gene Product," Yeast 21(6):473-82 (2004).
Luo et al., "Neutrophils Inhibit *Candidal* Expression of HYR1, Which Mediates Resistance to Neutrophil Killing," 48th Annual Interscience Conference on Antimicrobial Agents and Chemotherapy / 46th Annual Meeting of ISDA. Jan. 1, Washington, DC.. vol. 48: 654. Abstract M-1583 (2008).
Luo et al., "Candida albicans Hyr1p confers resistance to neutrophil killing and is a potential vaccine target," J Infect Dis. 201(11):1718-28 (2010) (11 pages).
Luo et al.,"Active and passive immunization with rHyr1p-N protects mice against hematogenously disseminated candidiasis," PloS One. 6(10):e25909 (2011) (8 pages).
Mamo et al., "Protection induced in mice vaccinated with recombinant collagen-binding protein (CnBP) and alpha-toxoid against intramammary infection with *Staphylococcus aureus*," Microbiol Immunol. 44(5):381-4 (2000).
Mamo et al., "Vaccination against *Staphylococcus aureus* mastitis: immunological response of mice vaccinated with fibronectin-binding protein (FnBP-A) to challenge with *S. aureus*," Vaccine. 12(11):988-92 (1994).
Mamo et al., "Vaccination with *Staphylococcus aureus* fibrinogen binding proteins (FgBPs) reduces colonisation of *S. aureus* in a mouse mastitis model," FEMS Immonol Med Microbiol. 10(1):47-53 (1994).
Manjarrez-Hernandez et al., "Binding of diarrheagenic *Escherichia coli* to 32- to 33-kilodalton human intestinal brush border proteins," Infect Immun. 65(11):4494-501 (1997).
Mayer et al., "Candida albicans adherence to endothelial cells," Microvasc Res. 43(2):218-26 (1992).
Mayer et al., "Recognition of binding sites on Candida albicans by monoclonal antibodies to human leukocyte antigens," Infect Immun. 58(11):3765-9 (1990).
Mukherjee et al., "Protective murine monoclonal antibodies to Cryptococcus neoformans," Infect Immun. 60(11):4534-41 (1992).
NCBI Blast for Accession No. YP 001084998. Retrieved on Nov. 27, 2012 (2 pages).
Nilsson et al., "Vaccination with a Recombinant Fragment of Collagen Adhesin Provides Protection against *Staphylococcus aureus*-mediated Septic Death," J Clin Invest. 101(12):2640-9 (1998).
Oh et al., "Functional specificity of Candida albicans Als3p proteins and clade specificity of ALS3 alleles discriminated by the number of the tandem repeat sequence in the central domain," Microbiology. 151(Pt 3):673-81 (2005).
Opal et al., "Systemic host responses in severe sepsis analyzed by causative microorganism and treatment effects of drotrecogin alfa (activated)," Clin Infect Dis. 37(1):50-8 (2003).
Palaszynski et al., "Systemic immunization with conserved pilus-associated adhesins protects against mucosal infections," Dev Biol Stand. 92:117-22 (1998).
Panaretou et al., Isolation of yeast plasma membranes. *Methods in Molecular Biology, vol. 53: Yeast Protocols*. I.H. Evans, 117-21 (1996).
Patti et al., "MSCRAMM-mediated adherence of microorganisms to host tissues," Annu Rev Microbiol. 48:585-617 (1994).
Patti, "Vaccines and immunotherapy for staphylococcal infections," Int J Artif Organs. 28(11):1157-62 (2005).
Peleg et al., "Prokaryote-eukaryote interactions identified by using Caenorhabditis elegans," Proc Natl Acad Sci USA. 105(38):14585-90 (2008).
Perraut et al., "Successful treatment of Candida albicans endophthalmitis with intravitreal amphotericin B," Arch Opthalmol. 99(9):1565-7 (1981).
Pfaller et al., "National surveillance of nosocomial blood stream infection due to species of Candida other than Candida albicans: frequency of occurrence and antifungal susceptibility in the SCOPE Program. SCOPE Participant Group. Surveillance and Control of Pathogens of Epidemiologic," Diagn Microbiol Infect Dis. 30(2):121-9 (1998).
Pietrella et al., "A beta-glucan-conjugate vaccine and anti-beta-glucan antibodies are effective against murine vaginal candidiasis as assessed by a novel in vivo imaging technique," Vaccine. 28(7):1717-25 (2010).
Polak, "Combination therapy of experimental candidiasis, cryptococcosis, aspergillosis and wangiellosis in mice," Chemotherapy. 33(5):381-95 (1987).
Prasadarao et al., "Identification and characterization of S fimbria-binding sialoglycoproteins on brain microvascular endothelial cells," Infect Immun. 65(7):2852-60 (1997).
Rieg et al., "Unanticipated heterogeneity in growth rate and virulence among Candida albicans AAF1 null mutants," Infect Immun. 67(7):3193-8 (1999).
Rotrosen et al., "Adherence of Candida to cultured vascular endothelial cells: mechanisms of attachment and endothelial cell penetration," J Infect Dis. 152(6):1264-74 (1985).
Sanford et al., "Passive immunization against Cryptococcus neoformans with an isotype-switch family of monoclonal antibodies reactive with cryptococcal polysaccharide," Infect Immun. 58(6):1919-23 (1990).
Sanger et al., "A rapid method for determining sequences in DNA by primed synthesis with DNA polymerase," J Mol Biol. 94(3):441-8 (1975).
Santoni, "Intravaginal and intranasal immunizations confer equal protection against Candida in experimental vaginitis," Abstracts of the General Meeting of the American Society for Microbiology 101:367-8 (2001) (3 pages).
Saporito-Irwin et al., "PHR1, a pH-regulated gene of Candida albicans, is required for morphogenesis," Mol Cell Biol. 15(2):601-13 (1995).
Schmidt et al., "NDV-3, a recombinant alum-adjuvanted vaccine for Candida and *Staphylococcus aureus* is safe and immunogenic in healthy adults," Vaccine. 30(52):7594-600 (2012) (18 pages).
Schnaar, "Isolation of glycosphingolipids," Methods Enzymol. 230:348-70 (1994).
Search Information Statement for Australian Patent Application No. 2006244401, dated Nov. 24, 2010 (3 pages).
Segal et al.,"Protection against systemic infections with various *Candida* species elicited by vaccination with *Candida albicans* ribosomes," Sabouraudia. 23(4):275-85 (1985).

(56) References Cited

OTHER PUBLICATIONS

Sheppard et al., "Functional and structural diversity in the Als protein family of Candida albicans," J Biol Chem. 279(29):30480-9 (2004).
Sheth et al., "Development of an anti-adhesive vaccine for Pseudomonas aeruginosa targeting the c-terminal region of the pilin structural protein," Biomed Pept Proteins Nucleic Acids. 1(3):141-8 (1995).
Smith et al., "New insights into Acinetobacter baumannii pathogenesis revealed by high-density pyrosequencing and transposon mutagenesis," Genes Dev. 21(5):601-14 (2007).
Soares et al.,"2-DE analysis indicates that Acinetobacter baumannii displays a robust and versatile metabolism," Proteome Sci. 7:37 (2009) (10 pages).
Spellberg et al., "Current treatment strategies for disseminated candidiasis," Clin Infect Dis 42(2):244-51 (2006).
Spellberg et al., "Efficacy of the Anti-Candida rAls3p-N or rAls1p-N Vaccines against Disseminated and Mucosal Candidiasis," J Infect Dis 194(2):256-60 (2006).
Spellberg et al., "Parenchymal organ, and not splenic, immunity correlates with host survival during disseminated candidiasis," Infect Immun. 71(10):5756-64 (2003).
Spellberg et al., "The antifungal vaccine derived from the recombinant N terminus of Als3p protects mice against the bacterium *Staphylococcus aureus*," Infect Immun. 76(10):4574-80 (2008).
Spellberg et al., "Mice with disseminated candidiasis die of progressive sepsis," J Infect Dis. 192(2):336-43 (2005).
Stuehler et al.,"Cross-protective TH1 immunity against Aspergillus fumigatus and Candida albicans," Blood. 117(22):5881-91 (2011).
Sundstrom, "Adhesion in *Candida* spp," Cell Microbiol. 4(8):461-9 (2002).
New Riverside University Dictionary, The Riverside Publishing Company, p. 933 (1984) (2 pages).
Translation of Cited Reference 3: Today's Therapy 2002, Igaku-Shoin Ltd., p. 155-156 from Japanese Application No. 2012-207831 (5 pages).
Translation of Cited Reference 2: Today's Therapy 2004, Igaku-Shoin Ltd, p. 166 from Japanese Application No. 2012-207831 (5 pages).
Torosantucci et al., "Protection by Anti-Beta-Glucan Antibodies is Associated with Restricted Beta-1,3 Glucan Binding Specificity and Inhibition of Fungal Growth and Adherence," PLoS ONE 4(4):e5392 (2009) (17 Pages).
Uniprot Submission P46591. Nov. 1995. <http://www.uniprot.org/uniprotIP46591.txt?version=39> Retrieved Sep. 16, 2010 (2 pages).
von Eiff et al., "Distribution of capsular and surface polysaccharide serotypes of *Staphylococcus aureus*," Diagn Microbiol Infect Dis. 58(3):297-302 (2007).
Wenzel et al., "Candida species: emerging hospital bloodstream pathogens [editoral]," Infect Control Hosp Epidermiol. 12(9):523-4 (1991).
Wey et al., "Hospital-acquired candidemia. The attributable mortality and excess length of stay," Arch Intern Med. 148(12):2642-5 (1988).
Wisplinghoff et al., "Nosocomial bloodstream infections in US hospitals: analysis of 24,179 cases from a prospective nationwide surveillance study," Clin Infect Dis. 39(3):309-17 (2004).
Wojciechowicz et al., "Cell surface anchorage and ligand-binding domains of the *Saccharomyces cerevisiae* cell adhesion protein alpha-agglutinin, a member of the immunoglobulin superfamily," Mol Cell Biol. 13(4):2554-63 (1993).
Xiong et al., "New Approaches to the Prevention and Treatment of Severe *S. aureus* Infections," Drugs Today (Barc). 36(8):529-39 (2000).
Yan et al., "Hemoglobin-induced binding of Candida albicans to the cell-binding domain of fibronectin is independent of the Arg-Gly-Asp sequence," Infect Immun. 66(5):1904-9 (1998).
Yeaman et al., "Mechanisms of NDV-3 vaccine efficacy in MRSA skin versus invasive infection," Proc Natl Acad Sci USA. 111(51):E5555-63 (2014).
Zhang et al., "Crystal Structure of Glutathione-Dependent Phospholipid Peroxidase Hyr1 from the Yeast *Saccharamvcas cerevisiae*," Proteins 73(4):1058-62 (2008).
Zhao et al., "Allelic variation in the contiguous loci encoding Candida albicans ALS5, ALS1 and ALS9," Microbiology. 149(Pt 10):2947-60 (2003).
Zhao et al., "ALS3 and ALS8 represent a single locus that encodes a Candida albicans adhesion; functional comparisons between Als3p and Als1p," Microbiology. 150(Pt 7):2415-28 (2004).
Zhao et al., "Analysis of the candida albicans Als2p and Als4p adhesins suggests the potential for compensatory function within the Als family," Microbiology. 151(Pt 5):1619-30 (2005).
Examiner's First Report for Australian Patent Application No. 2006244401, dated Nov. 25, 2010 (1 page).
Patent Examination Report No. 2 for Australian Patent Application No. 2006244401, dated Aug. 21, 2012 (3 pages).
Examiner's First Report for Australian Patent Application No. 2007205065, dated Jan. 18, 2012 (2 pages).
Patent Examination Report No. 2 for Australian Patent Application No. 2007205065, dated Mar. 12, 2013 (3 pages).
Patent Examination Report No. 3 for Australian Patent Application No. 2007205065, dated Oct. 15, 2013 (3 pages).
Patent Examination Report No. 1 for Australian Patent Application No. 2010266114, dated Dec. 31, 2014 (3 pages).
Patent Examination Report No. 1 for Australian Patent Application No. 2013203750, dated Aug. 20, 2014 (4 pages).
Examiner's Report for Canadian Patent Application No. 2,607,176, dated Nov. 26, 2012 (3 pages).
Examiner's Report for Canadian Patent Application No. 2,636,277, dated Dec. 4, 2012 (5 pages).
Examiner's Report for Canadian Patent Application No. 2,636,277, dated May 13, 2014 (2 pages).
First Office Action for Chinese Patent Application No. 201080039446.5, dated May 31, 2013 (English language Translation Provided) (11 Pages).
Second Office Action for Chinese Patent Application No. 201080039446.5, dated Nov. 18, 2013 (English language translation provided) (7 pages).
First Office Action for Chinese Patent Application No. 201280046321.4, dated Jan. 19, 2015 (20 pages, English language translation provided).
Second Office Action for Chinese Patent Application No. 201280046321.4, dated Oct. 26, 2015 (14 pages, English language translation provided).
Extended European Search Report for European Application No. 06752341.5, dated Nov. 13, 2009 (15 pages).
Extended European Search Report for European Patent Application No. 07709622.0, dated Nov. 19, 2009 (9 pages).
Communication pursuant to Article 94(3) EPC for European Patent Application No. 07709622.0, dated Nov. 17, 2010 (12 pages).
Communication pursuant to Article 94(3) EPC for European Patent Application No. 07709622.0, dated Mar. 3, 2010 (6 pages).
Communication pursuant to Article 94(3) EPC for European Patent Application No. 07709622.0, dated Jun. 30, 2011 (4 pages).
Communication under Rule 71(3) EPC for European Patent Application No. 07709622.0, dated Jan. 27, 2012 (8 pages).
Extended European Search Report for European Patent Application No. 10794828.3, dated Nov. 30, 2012 (9 pages).
Communication pursuant to Article 94(3) EPC for European Patent Application No. 10794828.3, dated May 19, 2014 (5 pages).
Invitation pursuant to Article 94(3) and Rule 71(1) EPC for European Patent Application No. 10794828.3, dated Sep. 21, 2015 (3 pages).
Extended European Search Report for European Patent Application No. 11008862.2, dated Feb. 10, 2012 (10 pages).
Communication pursuant to Article 94(3) EPC for European Patent Application No. 11008862.2, dated Apr. 23, 2014 (6 pages).
Summons to attend oral proceedings pursuant to Rule 115(1) EPC for European Patent Application No. 11008862.2, dated Oct. 20, 2015 (6 pages).
Extended European Search Report for European Patent Application No. 12001595.3, dated Nov. 13, 2012 (12 pages).

(56) References Cited

OTHER PUBLICATIONS

Communication pursuant to Article 94(3) EPC for European Patent Application No. 12001595.3, dated Apr. 23, 2014 (6 pages).
Extended European Search Report for European Patent Application No. 12001586.2, dated Nov. 13, 2012 (14 pages).
Communication pursuant to Article 94(3) EPC for European Patent Application No. 12001586.2, dated Apr. 23, 2014 (6 pages).
Summons to attend oral proceedings pursuant to Rule 115(1) EPC for European Patent Application No. 12001586.2, dated Oct. 19, 2015 (7 pages).
Extended European Search Report for European Application No. 12832321.9, dated Jun. 3, 2015 (9 pages).
Extended European Search Report for European Application No. 12817530.4, dated Dec. 18, 2014 (6 pages).
Notice of Reasons for Rejection for Japanese Patent Application No. 2008-549598, dated Mar. 21, 2012 (15 pages).
Final Japanese Office Action for Japanese Patent Application No. 2008-510281, dated Oct. 26, 2012 (3 pages).
English translation of the Final Japanese Office Action for Japanese Patent Application No. 2008-549598, dated Feb. 25, 2013 (5 pages).
Japanese Inquiry Rejection for Japanese Patent Application No. 2008-549598, dated Mar. 7, 2014 (13 pages).
Notice of Reasons for Rejection for Japanese Patent Application No. 2012-207831, dated Nov. 22, 2013 (15 pages).
Final Japanese Office Action for Japanese Patent Application No. 2012-207831, dated Dec. 16, 2014 (10 pages).
Japanese Office Action for Japanese Patent Application No. 2014-105980, dated Apr. 24, 2015 (2 pages).
Examination Report for New Zealand Patent Application No. 597442, dated Jul. 18, 2012 (2 pages).
Office Action for Russian Patent Application No. 2012103502, dated Oct. 14, 2014 (English language translation provided) (5 pages).
Office Action for Russian Patent Application No. 2012103502, dated May 21, 2014 (English translation provided) (6 pages).
Office Action for Ukrainian Patent Application No. a 2013 10981, dated Nov. 13, 2015 (English translation provided) (6 pages).
Office Action for Eurasian Patent Application No. 201391199/28, dated Sep. 20, 2015 (1 page, no English language translation provided).
Office Action for Georgian Patent Application No. 13226/01, dated Feb. 9, 2015 (2 pages, English language translation provided).
Office Action for Georgian Patent Application No. 13225/01, dated Sep. 23, 2015 (1 page, no English language translation provided).
International Search Report for International Application No. PCT/US2006/017482, dated Mar. 19, 2007 (2 pages).
Written Opinion of the International Searching Authority for International Application No. PCT/US2006/017482, dated Mar. 19, 2007 (3 pages).
International Preliminary Report on Patentability for International Application No. PCT/US2006/017482, dated Nov. 6, 2007 (4 pages).
International Search Report for International Patent Application No. PCT/US2007/000433, dated Oct. 1, 2007 (1 page).
Written Opinion of the International Searching Authority for International Application No. PCT/US2007/000433, dated Oct. 1, 2007 (4 pages).
International Preliminary Report on Patentability for International Application No. PCT/US2007/000433, dated Jul. 8, 2008 (5 pages).
International Search Report for International Patent Application No. PCT/US12/55604, dated Mar. 8, 2013 (9 pages).
Written Opinion of the International Searching Authority for International Patent Application No. PCT/US12/55604, dated Mar. 8, 2013 (10 pages).
International Preliminary Report on Patentability for International Patent Application No. PCT/US12/55604, dated Mar. 18, 2014 (11 pages).
International Search Report of International Application No. PCT/US12/00328, dated Dec. 18, 2012 (3 pages).
Written Opinion of the International Searching Authority for International Application No. PCT/US12/00328, dated Dec. 18, 2012 (5 pages).
International Preliminary Report on Patentability for International Application No. PCT/US12/00328, dated Jan. 28, 2014 (6 pages).
International Search Report for International Application No. PCT/US2010/040949, dated Jun. 6, 2011 (3 pages).
Written Opinion of the International Searching Authority for International Application No. PCT/US2010/040949, dated Jun. 6, 2011 (4 pages).
International Preliminary Report on Patentability for International Application No. PCT/US2010/040949, dated Jan. 4, 2012 (5 pages).
Liang et al., "Prediction of antigenic epitopes on protein surfaces by consensus scoring," BMC Bioinformatics 10:302 (2009) (10 pages).
Zhao et al., "ALS3 and ALS8 represent a single locus that encodes a Candida albicans adhesin; functional comparisons between Als3p and Als1p," GenBank AAO72958.1 (Definition: agglutinin-like sequence 3 [Candida albicans]), PLN Jul. 16, 1004 (2 pages).
International Search Report for International Patent Application No. PCT/US2014/28535, dated Oct. 24, 2014 (5 pages).
Written Opinion of the International Searching Authority for International Patent Application No. PCT/US2014/28535, dated Oct. 24, 2014 (6 pages).
International Preliminary Report on Patentability for International Patent Application No. PCT/US2014/28535, dated Sep. 15, 2015 (7 pages).
International Search Report for International Patent Application No. PCT/US2014/28521, dated Nov. 13, 2014 (7 pages).
Written Opinion of the International Searching Authority for International Patent Application No. PCT/US2014/28521, dated Nov. 13, 2014 (10 pages).
International Preliminary Report on Patentability for International Patent Application No. PCT/US2014/28521, dated Oct. 13, 2015 (11 pages).
International Search Report for International Patent Application No. PCT/US2014/28256, dated Aug. 18, 2014 (4 pages).
Written Opinion of the International Searching Authority for International Patent Application No. PCT/US2014/28256, dated Aug. 18, 2014 (6 pages).
International Preliminary Report on Patentability for International Patent Application No. PCT/US2014/28256, dated Sep. 15, 2015 (7 pages).
First Office Action for Chinese Patent Application No. 201280056018.2, dated Mar. 14, 2016 (English language translation provided) (27 pages).
Notification of Reason for Rejection for Japanese Patent Application No. 2014-105980, dated Jan. 29, 2016 (English language translation provided, 13 pages).
Notice of Reasons for Rejection for Japanese Patent Application No. 2015-018131, dated Mar. 16, 2016 (9 pages) (English language translation provided).
Notice of Reasons for Rejection for Japanese Patent Application No. 2014-521610, dated Apr. 20, 2016 (11 pages) (English language translation provided).
Notice of Reasons for Rejection for Japanese Patent Application No. 2014-530899, dated Jul. 21, 2016 (English language translation provided) (14 pages).
Search Report for Eurasian Patent Application No. 201591808/26, dated Mar. 23, 2016 (No English language translation provided) (3 pages).
Office Action for Georgian Patent Application No. 13226/01, dated Feb. 15, 2016 (No English translation provided) (2 pages).
Office Action for Ukrainian Patent Application No. a 2013 10982, dated Jan. 15, 2016 (No English language translation provided, 6 pages).
Examiner Report for Canadian Patent Application No. 2,636,277, dated May 12, 2016 (5 pages).
Communication pursuant to Rule 164(1) EPC for European Patent Application No. 14764623.6, dated Aug. 2, 2016 (7 pages).
Non-Final Office Action for U.S. Appl. No. 11/327,197, dated Aug. 31, 2016 (24 pages).

(56) References Cited

OTHER PUBLICATIONS

Harlow et al., Monoclonal Antibodies. *Antibodies: A Laboratory Manual*. Cold Spring Harbor Laboratory, 139-172 (1988).
Lin et al., "Acinetobacter baumannii rOmpA vaccine dose alters immune polarization and immunodominant epitopes," available in PMC Jan. 2, 2014, published in final edited form as: Vaccine 31(2):313-8 (2013) (14 pages).
Spellberg et al., "The pathophysiology and treatment of Candida sepsis," Curr Infect Dis Rep. 4(5):387-99 (2002).
Skolnick et al., "From genes to protein structure and function: novel applications of computational approaches in the genomic era," Trends Biotechnol. 18(1):34-9 (2000).
Zhao et al., "Candida albicans Als3p is required for wild-type biofilm formation on silicone elastomer surfaces," available in PMC Nov. 14, 2008, published in final edited form as: Microbiology. 152(Pt 8):2287-2299 (2006) (25 pages).
International Search Report for International Application No. PCT/US2018/026889, dated Jul. 11, 2018 (4 pages).
Written Opinion of the International Searching Authority for International Application No. PCT/US2018/026889, dated Jul. 11, 2018 (13 pages).
Chowdhary et al., "Candida auris: A rapidly emerging cause of hospital-acquired multidrug-resistant fungal infections globally," PLoS Pathog. 13(5):e1006290 (2017) (10 pages).
Kaur et al., "Strategies to reduce mortality in adult and neonatal Candidemia in developing countries," J Fungi (Basel). 3(3):pii:E41 (2017) (20 pages).
Sherry et al., "Biofilm-forming capability of highly virulent, multidrug-resistant *Candida auris*," Emerg Infect Dis. 23(2):328-331 (2017).
Extended European Search Report for European Patent Application No. 18166876.5, dated Jul. 31, 2018 (10 pages).
Larkin et al., "The Emerging Pathogen Candida auris: Growth Phenotype, Virulence Factors, Activity of Antifungals, and Effect of SCY-078, a Novel Glucan Synthesis Inhibitor, on Growth Morphology and Biofilm Formation," Antimicrob Agents Chemother. 61(5). pii: e02396-16 (2017).
Sui et al., "The vaccines and antibodies associated with Als3p for treatment of Candida albicans infections," Vaccine 35(43):5786-5793 (2017).
Tsay et al., "Approach to the Investigation and Management of Patients With Candida auris, an Emerging Multidrug-Resistant Yeast," Clin Infect Dis. 66(2):306-311 (2018).

\* cited by examiner

SEQUENCE LISTING

<160> NUMBER OF SEQ ID NOS: 34

<210> SEQ ID NO 1
<211> LENGTH: 1119
<212> TYPE: PRT
<213> ORGANISM: Candida albicans

<400> SEQUENCE: 1

```
Met Leu Gln Gln Tyr Thr Leu Leu Ile Tyr Leu Ser Val Ala Thr
1               5                   10                  15

Ala Lys Thr Ile Thr Gly Val Phe Asn Ser Phe Asn Ser Leu Thr Trp
            20                  25                  30

Ser Asn Ala Ala Thr Tyr Asn Tyr Lys Gly Pro Gly Thr Pro Thr Trp
            35                  40                  45

Asn Ala Val Leu Gly Trp Ser Leu Asp Gly Thr Ser Ala Ser Pro Gly
            50                  55                  60

Asp Thr Phe Thr Leu Asn Met Pro Cys Val Phe Lys Phe Thr Thr Ser
65                  70                  75                  80

Gln Thr Ser Val Asp Leu Thr Ala His Gly Val Lys Tyr Ala Thr Cys
                85                  90                  95

Gln Phe Gln Ala Gly Glu Glu Phe Met Thr Phe Ser Thr Leu Thr Cys
            100                 105                 110

Thr Val Ser Asn Thr Leu Thr Pro Ser Ile Lys Ala Leu Gly Thr Val
            115                 120                 125

Thr Leu Pro Leu Ala Phe Asn Val Gly Gly Thr Gly Ser Ser Val Asp
130                 135                 140

Leu Glu Asp Ser Lys Cys Phe Thr Ala Gly Thr Asn Thr Val Thr Phe
145                 150                 155                 160

Asn Asp Gly Gly Lys Lys Ile Ser Ile Asn Val Asp Phe Glu Arg Ser
                165                 170                 175

Asn Val Asp Pro Lys Gly Tyr Leu Thr Asp Ser Arg Val Ile Pro Ser
            180                 185                 190

Leu Asn Lys Val Ser Thr Leu Phe Val Ala Pro Gln Cys Ala Asn Gly
            195                 200                 205

Tyr Thr Ser Gly Thr Met Gly Phe Ala Asn Thr Tyr Gly Asp Val Gln
210                 215                 220

Ile Asp Cys Ser Asn Ile His Val Gly Ile Thr Lys Gly Leu Asn Asp
225                 230                 235                 240

Trp Asn Tyr Pro Val Ser Ser Glu Ser Phe Ser Tyr Thr Lys Thr Cys
                245                 250                 255

Ser Ser Asn Gly Ile Phe Ile Thr Tyr Lys Asn Val Pro Ala Gly Tyr
            260                 265                 270

Arg Pro Phe Val Asp Ala Tyr Ile Ser Ala Thr Asp Val Asn Ser Tyr
            275                 280                 285

Thr Leu Ser Tyr Ala Asn Glu Tyr Thr Cys Ala Gly Gly Tyr Trp Gln
            290                 295                 300

Arg Ala Pro Phe Thr Leu Arg Trp Thr Gly Tyr Arg Asn Ser Asp Ala
305                 310                 315                 320

Gly Ser Asn Gly Ile Val Ile Val Ala Thr Thr Arg Thr Val Thr Asp
                325                 330                 335

Ser Thr Thr Ala Val Thr Thr Leu Pro Phe Asp Pro Asn Arg Asp Lys
            340                 345                 350

Thr Lys Thr Ile Glu Ile Leu Lys Pro Ile Pro Thr Thr Thr Ile Thr
            355                 360                 365

Thr Ser Tyr Val Gly Val Thr Thr Ser Tyr Ser Thr Lys Thr Ala Pro
            370                 375                 380

Ile Gly Glu Thr Ala Thr Val Ile Val Asp Ile Pro Tyr His Thr Thr
385                 390                 395                 400

Thr Thr Val Thr Ser Lys Trp Thr Gly Thr Ile Thr Ser Thr Thr Thr
                405                 410                 415
```

His Thr Asn Pro Thr Asp Ser Ile Asp Thr Val Ile Val Gln Val Pro
            420                 425                 430

Ser Pro Asn Pro Thr Val Thr Thr Glu Tyr Trp Ser Gln Ser Phe
            435                 440                 445

Ala Thr Thr Thr Thr Ile Thr Gly Pro Pro Gly Asn Thr Asp Thr Val
            450                 455                 460

Leu Ile Arg Glu Pro Pro Asn His Thr Val Thr Thr Glu Tyr Trp
465                 470                 475                 480

Ser Glu Ser Tyr Thr Thr Thr Ser Thr Phe Thr Ala Pro Pro Gly Gly
            485                 490                 495

Thr Asp Ser Val Ile Ile Lys Glu Pro Pro Asn Pro Thr Val Thr Thr
            500                 505                 510

Thr Glu Tyr Trp Ser Glu Ser Tyr Thr Thr Ser Thr Phe Thr Ala
            515                 520                 525

Pro Pro Gly Gly Thr Asp Ser Val Ile Ile Lys Glu Pro Pro Asn His
            530                 535                 540

Thr Val Thr Thr Thr Glu Tyr Trp Ser Gln Ser Tyr Thr Thr Thr Thr
545                 550                 555                 560

Thr Val Thr Ala Pro Pro Gly Gly Thr Asp Thr Val Leu Val Arg Glu
            565                 570                 575

Pro Pro Asn His Thr Val Thr Thr Thr Glu Tyr Trp Ser Gln Ser Tyr
            580                 585                 590

Thr Thr Thr Thr Thr Val Ile Ala Pro Pro Gly Gly Thr Asp Ser Val
            595                 600                 605

Ile Ile Arg Glu Pro Pro Asn Pro Thr Val Thr Thr Glu Tyr Trp
            610                 615                 620

Ser Gln Ser Tyr Ala Thr Thr Thr Thr Ile Thr Ala Pro Pro Gly Glu
625                 630                 635                 640

Thr Asp Thr Val Leu Ile Arg Glu Pro Pro Asn His Thr Val Thr Thr
            645                 650                 655

Thr Glu Tyr Trp Ser Gln Ser Tyr Ala Thr Thr Thr Ile Thr Ala
            660                 665                 670

Pro Pro Gly Glu Thr Asp Thr Val Leu Ile Arg Glu Pro Pro Asn His
            675                 680                 685

Thr Val Thr Thr Thr Glu Tyr Trp Ser Gln Ser Phe Ala Thr Thr Thr
            690                 695                 700

Thr Val Thr Ala Pro Pro Gly Gly Thr Asp Thr Val Ile Ile Arg Glu
705                 710                 715                 720

Pro Pro Asn His Thr Val Thr Thr Thr Glu Tyr Trp Ser Gln Ser Tyr
            725                 730                 735

Ala Thr Thr Thr Thr Ile Thr Ala Pro Pro Gly Glu Thr Asp Thr Val
            740                 745                 750

Leu Ile Arg Glu Pro Pro Asn His Thr Val Thr Thr Glu Tyr Trp
            755                 760                 765

Ser Gln Ser Tyr Ala Thr Thr Thr Ile Ile Ala Pro Pro Gly Glu
            770                 775                 780

Thr Asp Thr Val Leu Ile Arg Glu Pro Pro Asn Pro Thr Val Thr Thr
785                 790                 795                 800

Thr Glu Tyr Trp Ser Gln Ser Tyr Thr Thr Ala Thr Thr Val Thr Ala
            805                 810                 815

Pro Pro Gly Gly Thr Asp Thr Val Ile Ile Tyr Asp Thr Met Ser Ser
            820                 825                 830

```
Ser Glu Ile Ser Ser Phe Ser Arg Pro His Tyr Thr Asn His Thr Thr
        835                 840                 845

Leu Trp Ser Thr Thr Trp Val Ile Glu Thr Lys Thr Ile Thr Glu Thr
    850                 855                 860

Ser Cys Glu Gly Asp Lys Gly Cys Ser Trp Val Ser Val Ser Thr Arg
865                 870                 875                 880

Ile Val Thr Ile Pro Asn Asn Ile Glu Thr Pro Met Val Thr Asn Thr
                885                 890                 895

Val Asp Ser Thr Thr Glu Ser Ser Gln Ser Pro Ser Gly Ile
                900                 905                 910

Phe Ser Glu Ser Gly Val Ser Val Glu Thr Glu Ser Thr Val Thr
    915                 920                 925

Thr Ala Gln Thr Asn Pro Ser Val Pro Thr Thr Glu Ser Glu Val Val
    930                 935                 940

Phe Thr Thr Lys Gly Asn Asn Glu Asn Gly Pro Tyr Glu Ser Pro Ser
945                 950                 955                 960

Thr Asn Val Lys Ser Ser Met Asp Glu Asn Ser Glu Phe Thr Thr Ser
                965                 970                 975

Thr Ala Ala Ser Thr Ser Thr Asp Ile Glu Asn Glu Thr Ile Ala Thr
                980                 985                 990

Thr Gly Ser Val Glu Ala Ser Ser Pro Ile Ile Ser Ser Ser Ala Asp
    995                 1000                1005

Glu Thr Thr Thr Val Thr Thr Thr Ala Glu Ser Thr Ser Val Ile
    1010                1015                1020

Glu Gln Pro Thr Asn Asn Asn Gly Gly Gly Lys Ala Pro Ser Ala
    1025                1030                1035

Thr Ser Ser Pro Ser Thr Thr Thr Thr Ala Asn Asn Asp Ser Val
    1040                1045                1050

Ile Thr Gly Thr Thr Ser Thr Asn Gln Ser Gln Ser Gln Ser Gln
    1055                1060                1065

Tyr Asn Ser Asp Thr Gln Gln Thr Thr Leu Ser Gln Gln Met Thr
    1070                1075                1080

Ser Ser Leu Val Ser Leu His Met Leu Thr Thr Phe Asp Gly Ser
    1085                1090                1095

Gly Ser Val Ile Gln His Ser Thr Trp Leu Cys Gly Leu Ile Thr
    1100                1105                1110

Leu Leu Ser Leu Phe Ile
    1115

<210> SEQ ID NO 2
<211> LENGTH: 307
<212> TYPE: PRT
<213> ORGANISM: Candida albicans

<400> SEQUENCE: 2

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
                20                  25                  30

Ala Val Leu Gly Trp Ser Leu Asp Gly Thr Ser Ala Ser Pro Gly Asp
            35                  40                  45

Thr Phe Thr Leu Asn Met Pro Cys Val Phe Lys Phe Thr Thr Ser Gln
        50                  55                  60

Thr Ser Val Asp Leu Thr Ala His Gly Val Lys Tyr Ala Thr Cys Gln
65                  70                  75                  80
```

```
Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

Ser Asn Gly
305

<210> SEQ ID NO 3
<211> LENGTH: 108
<212> TYPE: PRT
<213> ORGANISM: Candida albicans

<400> SEQUENCE: 3

Ile Val Ile Val Ala Thr Thr Arg Thr Val Thr Asp Ser Thr Thr Ala
1               5                   10                  15

Val Thr Thr Leu Pro Phe Asp Pro Asn Arg Asp Lys Thr Lys Thr Ile
            20                  25                  30

Glu Ile Leu Lys Pro Ile Pro Thr Thr Ile Thr Thr Ser Tyr Val
        35                  40                  45

Gly Val Thr Thr Ser Tyr Ser Thr Lys Thr Ala Pro Ile Gly Glu Thr
    50                  55                  60

Ala Thr Val Ile Val Asp Ile Pro Tyr His Thr Thr Thr Thr Val Thr
65                  70                  75                  80

Ser Lys Trp Thr Gly Thr Ile Thr Ser Thr Thr Thr His Thr Asn Pro
                85                  90                  95

Thr Asp Ser Ile Asp Thr Val Ile Val Gln Val Pro
            100                 105

<210> SEQ ID NO 4
<211> LENGTH: 937
<212> TYPE: PRT
```

<213> ORGANISM: Candida albicans

<400> SEQUENCE: 4

```
Met Lys Val Val Ser Asn Phe Ile Phe Thr Ile Leu Leu Thr Leu Asn
1               5                   10                  15

Leu Ser Ala Ala Leu Glu Val Val Thr Ser Arg Ile Asp Arg Gly Gly
            20                  25                  30

Ile Gln Gly Phe His Gly Asp Val Lys Val His Ser Gly Ala Thr Trp
        35                  40                  45

Ala Ile Leu Gly Thr Thr Leu Cys Ser Phe Phe Gly Gly Leu Glu Val
    50                  55                  60

Glu Lys Gly Ala Ser Leu Phe Ile Lys Ser Asp Asn Gly Pro Val Leu
65                  70                  75                  80

Ala Leu Asn Val Ala Leu Ser Thr Leu Val Arg Pro Val Ile Asn Asn
                85                  90                  95

Gly Val Ile Ser Leu Asn Ser Lys Ser Ser Thr Ser Phe Ser Asn Phe
            100                 105                 110

Asp Ile Gly Gly Ser Ser Phe Thr Asn Asn Gly Glu Ile Tyr Leu Asp
        115                 120                 125

Ser Ser Gly Leu Val Lys Ser Thr Ala Tyr Leu Tyr Ala Arg Glu Trp
    130                 135                 140

Thr Asn Asn Gly Leu Ile Val Ala Tyr Gln Asn Gln Lys Ala Ala Gly
145                 150                 155                 160

Asn Ile Ala Phe Gly Thr Ala Tyr Gln Thr Ile Thr Asn Asn Gly Gln
                165                 170                 175

Ile Cys Leu Arg His Gln Asp Phe Val Pro Ala Thr Lys Ile Lys Gly
            180                 185                 190

Thr Gly Cys Val Thr Ala Asp Glu Asp Thr Trp Ile Lys Leu Gly Asn
        195                 200                 205

Thr Ile Leu Ser Val Glu Pro Thr His Asn Phe Tyr Leu Lys Asp Ser
    210                 215                 220

Lys Ser Ser Leu Ile Val His Ala Val Ser Ser Asn Gln Thr Phe Thr
225                 230                 235                 240

Val His Gly Phe Gly Asn Gly Asn Lys Leu Gly Leu Thr Leu Pro Leu
                245                 250                 255

Thr Gly Asn Arg Asp His Phe Arg Phe Glu Tyr Tyr Pro Asp Thr Gly
            260                 265                 270

Ile Leu Gln Leu Arg Ala Asp Ala Leu Pro Gln Tyr Phe Lys Ile Gly
        275                 280                 285

Lys Gly Tyr Asp Ser Lys Leu Phe Arg Ile Val Asn Ser Arg Gly Leu
    290                 295                 300

Lys Asn Ala Val Thr Tyr Asp Gly Pro Val Pro Asn Asn Glu Ile Pro
305                 310                 315                 320

Ala Val Cys Leu Ile Pro Cys Thr Asn Gly Pro Ser Ala Pro Glu Ser
                325                 330                 335

Glu Ser Asp Leu Asn Thr Pro Thr Ser Ser Ile Glu Thr Ser Ser
            340                 345                 350

Tyr Ser Ser Ala Ala Thr Glu Ser Ser Val Val Ser Glu Ser Ser Ser
        355                 360                 365

Ala Val Asp Ser Leu Thr Ser Ser Ser Leu Ser Ser Lys Ser Glu Ser
    370                 375                 380

Ser Asp Val Val Ser Ser Thr Thr Asn Ile Glu Ser Ser Ser Thr Ala
385                 390                 395                 400
```

-continued

```
Ile Glu Thr Thr Met Asn Ser Glu Ser Ser Thr Asp Ala Gly Ser Ser
                405                 410                 415

Ser Ile Ser Gln Ser Glu Ser Ser Thr Ala Ile Thr Ser Ser Ser
        420                 425                 430

Glu Thr Ser Ser Ser Glu Ser Met Ser Ala Ser Ser Thr Thr Ala Ser
            435                 440                 445

Asn Thr Ser Ile Glu Thr Asp Ser Gly Ile Val Ser Gln Ser Glu Ser
    450                 455                 460

Ser Ser Asn Ala Leu Ser Ser Thr Glu Gln Ser Ile Thr Ser Ser Pro
465                 470                 475                 480

Gly Gln Ser Thr Ile Tyr Val Asn Ser Thr Val Thr Ser Thr Ile Thr
                485                 490                 495

Ser Cys Asp Glu Asn Lys Cys Thr Glu Asp Val Val Thr Ile Phe Thr
                500                 505                 510

Thr Val Pro Cys Ser Thr Asp Cys Val Pro Thr Thr Gly Asp Ile Pro
            515                 520                 525

Met Ser Thr Ser Tyr Thr Gln Arg Thr Val Ser Thr Ile Thr Asn
    530                 535                 540

Cys Asp Glu Val Ser Cys Ser Gln Asp Val Val Thr Tyr Thr Thr Asn
545                 550                 555                 560

Val Pro His Thr Thr Val Asp Ala Thr Thr Thr Thr Thr Thr Ser Thr
                565                 570                 575

Gly Gly Asp Asn Ser Thr Gly Gly Asn Glu Ser Gly Ser Asn His Gly
            580                 585                 590

Pro Gly Asn Gly Ser Thr Glu Gly Ser Asn Gly Ser Gly Ala Gly
            595                 600                 605

Ser Asn Glu Gly Ser Gln Ser Gly Pro Asn Asn Gly Ser Gly Ser Gly
        610                 615                 620

Ser Glu Gly Gly Ser Asn Asn Gly Ser Gly Ser Asp Ser Gly Ser Asn
625                 630                 635                 640

Asn Gly Ser Gly Ser Gly Ser Asn Asn Gly Ser Gly Ser Gly Ser Thr
                645                 650                 655

Glu Gly Ser Glu Gly Gly Ser Gly Ser Asn Glu Gly Ser Gln Ser Gly
            660                 665                 670

Ser Gly Ser Gln Pro Gly Pro Asn Glu Gly Ser Glu Gly Gly Ser Gly
        675                 680                 685

Ser Asn Glu Gly Ser Asn His Gly Ser Asn Glu Gly Ser Gly Ser Gly
        690                 695                 700

Ser Gly Ser Gly Ser Asn Asn Gly Ser Gly Ser Gly Ser Gln Ser Gly
705                 710                 715                 720

Ser Gly Ser Gly Ser Gln Ser Gly Ser Glu Ser Gly Ser Asn Ser Gly
                725                 730                 735

Ser Asn Glu Gly Ser Asn Pro Gly Ala Gly Asn Gly Ser Asn Glu Gly
            740                 745                 750

Ser Gly Gln Gly Ser Gly Asn Gly Ser Glu Ala Gly Ser Gly Gln Gly
        755                 760                 765

Ser Gly Pro Asn Asn Gly Ser Gly Ser His Asn Asp Gly Ser Gly
        770                 775                 780

Ser Gly Ser Asn Gln Gly Ser Asn Pro Gly Ala Gly Ser Gly Ser Gly
785                 790                 795                 800

Ser Glu Ser Gly Ser Lys Ala Gly Ser His Ser Gly Ser Asn Glu Gly
                805                 810                 815

Ala Lys Thr Asp Ser Ile Glu Gly Phe His Thr Glu Ser Lys Pro Gly
```

```
                820                 825                 830
Phe Asn Thr Gly Ala His Thr Asp Ala Thr Val Thr Gly Asn Ser Val
            835                 840                 845

Ala Asn Pro Val Thr Thr Ser Thr Glu Ser Asp Thr Thr Ile Ser Val
850                 855                 860

Thr Val Ser Ile Thr Ser Tyr Met Thr Gly Phe Asp Gly Lys Pro Lys
865                 870                 875                 880

Pro Phe Thr Thr Val Asp Val Ile Pro Val Pro His Ser Met Pro Ser
                885                 890                 895

Asn Thr Thr Asp Ser Ser Ser Val Pro Thr Ile Asp Thr Asn Glu
            900                 905                 910

Asn Gly Ser Ser Ile Val Thr Gly Lys Ser Ile Leu Phe Gly Leu
        915                 920                 925

Ile Val Ser Met Val Val Leu Phe Met
        930                 935

<210> SEQ ID NO 5
<211> LENGTH: 129
<212> TYPE: PRT
<213> ORGANISM: Candida albicans

<400> SEQUENCE: 5

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
            20                  25                  30

Ser Phe Phe Gly Gly Leu Glu Val Glu Lys Gly Ala Ser Leu Phe Ile
        35                  40                  45

Lys Ser Asp Asn Gly Pro Val Leu Ala Leu Asn Val Ala Leu Ser Thr
50                  55                  60

Leu Val Arg Pro Val Ile Asn Asn Gly Val Ile Ser Leu Asn Ser Lys
65                  70                  75                  80

Ser Ser Thr Ser Phe Ser Asn Phe Asp Ile Gly Gly Ser Ser Phe Thr
            85                  90                  95

Asn Asn Gly Glu Ile Tyr Leu Asp Ser Ser Gly Leu Val Lys Ser Thr
        100                 105                 110

Ala Tyr Leu Tyr Ala Arg Glu Trp Thr Asn Asn Gly Leu Ile Val Ala
        115                 120                 125

Tyr

<210> SEQ ID NO 6
<211> LENGTH: 197
<212> TYPE: PRT
<213> ORGANISM: Candida albicans

<400> SEQUENCE: 6

Gln Asn Gln Lys Ala Ala Gly Asn Ile Ala Phe Gly Thr Ala Tyr Gln
1               5                   10                  15

Thr Ile Thr Asn Asn Gly Gln Ile Cys Leu Arg His Gln Asp Phe Val
            20                  25                  30

Pro Ala Thr Lys Ile Lys Gly Thr Gly Cys Val Thr Ala Asp Glu Asp
        35                  40                  45

Thr Trp Ile Lys Leu Gly Asn Thr Ile Leu Ser Val Glu Pro Thr His
        50                  55                  60

Asn Phe Tyr Leu Lys Asp Ser Lys Ser Ser Leu Ile Val His Ala Val
65                  70                  75                  80
```

```
Ser Ser Asn Gln Thr Phe Thr Val His Gly Phe Gly Asn Gly Asn Lys
            85                  90                  95

Leu Gly Leu Thr Leu Pro Leu Thr Gly Asn Arg Asp His Phe Arg Phe
            100                 105                 110

Glu Tyr Tyr Pro Asp Thr Gly Ile Leu Gln Leu Arg Ala Asp Ala Leu
            115                 120                 125

Pro Gln Tyr Phe Lys Ile Gly Lys Gly Tyr Asp Ser Lys Leu Phe Arg
            130                 135                 140

Ile Val Asn Ser Arg Gly Leu Lys Asn Ala Val Thr Tyr Asp Gly Pro
145                 150                 155                 160

Val Pro Asn Asn Glu Ile Pro Ala Val Cys Leu Ile Pro Cys Thr Asn
            165                 170                 175

Gly Pro Ser Ala Pro Glu Ser Glu Ser Asp Leu Asn Thr Pro Thr Thr
            180                 185                 190

Ser Ser Ile Glu Thr
            195

<210> SEQ ID NO 7
<211> LENGTH: 150
<212> TYPE: PRT
<213> ORGANISM: Candida albicans

<400> SEQUENCE: 7

Asp Thr Trp Ile Lys Leu Gly Asn Thr Ile Leu Ser Val Glu Pro Thr
1               5                   10                  15

His Asn Phe Tyr Leu Lys Asp Ser Lys Ser Ser Leu Ile Val His Ala
            20                  25                  30

Val Ser Ser Asn Gln Thr Phe Thr Val His Gly Phe Gly Asn Gly Asn
            35                  40                  45

Lys Leu Gly Leu Thr Leu Pro Leu Thr Gly Asn Arg Asp His Phe Arg
    50                  55                  60

Phe Glu Tyr Tyr Pro Asp Thr Gly Ile Leu Gln Leu Arg Ala Asp Ala
65                  70                  75                  80

Leu Pro Gln Tyr Phe Lys Ile Gly Lys Gly Tyr Asp Ser Lys Leu Phe
            85                  90                  95

Arg Ile Val Asn Ser Arg Gly Leu Lys Asn Ala Val Thr Tyr Asp Gly
            100                 105                 110

Pro Val Pro Asn Asn Glu Ile Pro Ala Val Cys Leu Ile Pro Cys Thr
            115                 120                 125

Asn Gly Pro Ser Ala Pro Glu Ser Glu Ser Asp Leu Asn Thr Pro Thr
            130                 135                 140

Thr Ser Ser Ile Glu Thr
145                 150

<210> SEQ ID NO 8
<211> LENGTH: 445
<212> TYPE: PRT
<213> ORGANISM: Candida albicans

<400> SEQUENCE: 8

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
            20                  25                  30

Ser Phe Phe Gly Gly Leu Glu Val Glu Lys Gly Ala Ser Leu Phe Ile
            35                  40                  45
```

```
Lys Ser Asp Asn Gly Pro Val Leu Ala Leu Asn Val Ala Leu Ser Thr
 50              55                  60

Leu Val Arg Pro Val Ile Asn Asn Gly Val Ile Ser Leu Asn Ser Lys
 65              70                  75                  80

Ser Ser Thr Ser Phe Ser Asn Phe Asp Ile Gly Gly Ser Ser Phe Thr
                 85                  90                  95

Asn Asn Gly Glu Ile Tyr Leu Asp Ser Ser Gly Leu Val Lys Ser Thr
                100                 105                 110

Ala Tyr Leu Tyr Ala Arg Glu Trp Thr Asn Asn Gly Leu Ile Val Ala
            115                 120                 125

Tyr Gln Asn Gln Lys Ala Ala Gly Asn Ile Ala Phe Gly Thr Ala Tyr
130                 135                 140

Gln Thr Ile Thr Asn Asn Gly Gln Ile Cys Leu Arg His Gln Asp Phe
145                 150                 155                 160

Val Pro Ala Thr Lys Ile Lys Gly Thr Gly Cys Val Thr Ala Asp Glu
                165                 170                 175

Asp Thr Trp Ile Lys Leu Gly Asn Thr Ile Leu Ser Val Glu Pro Thr
            180                 185                 190

His Asn Phe Tyr Leu Lys Asp Ser Lys Ser Ser Leu Ile Val His Ala
            195                 200                 205

Val Ser Ser Asn Gln Thr Phe Thr Val His Gly Phe Gly Asn Gly Asn
210                 215                 220

Lys Leu Gly Leu Thr Leu Pro Leu Thr Gly Asn Arg Asp His Phe Arg
225                 230                 235                 240

Phe Glu Tyr Tyr Pro Asp Thr Gly Ile Leu Gln Leu Arg Ala Asp Ala
                245                 250                 255

Leu Pro Gln Tyr Phe Lys Ile Gly Lys Gly Tyr Asp Ser Lys Leu Phe
            260                 265                 270

Arg Ile Val Asn Ser Arg Gly Leu Lys Asn Ala Val Thr Tyr Asp Gly
            275                 280                 285

Pro Val Pro Asn Asn Glu Ile Pro Ala Val Cys Leu Ile Pro Cys Thr
290                 295                 300

Asn Gly Pro Ser Ala Pro Glu Ser Glu Ser Asp Leu Asn Thr Pro Thr
305                 310                 315                 320

Thr Ser Ser Ile Glu Thr Ser Ser Tyr Ser Ser Ala Ala Thr Glu Ser
                325                 330                 335

Ser Val Val Ser Glu Ser Ser Ala Val Asp Ser Leu Thr Ser Ser
            340                 345                 350

Ser Leu Ser Ser Lys Ser Glu Ser Ser Asp Val Val Ser Ser Thr Thr
            355                 360                 365

Asn Ile Glu Ser Ser Thr Ala Ile Glu Thr Thr Met Asn Ser Glu
370                 375                 380

Ser Ser Thr Asp Ala Gly Ser Ser Ile Ser Gln Ser Glu Ser Ser
385                 390                 395                 400

Ser Thr Ala Ile Thr Ser Ser Glu Thr Ser Ser Glu Ser Met
            405                 410                 415

Ser Ala Ser Ser Thr Thr Ala Ser Asn Thr Ser Ile Glu Thr Asp Ser
            420                 425                 430

Gly Ile Val Ser Gln Ser Glu Ser Ser Asn Ala Leu
            435                 440                 445

<210> SEQ ID NO 9
<211> LENGTH: 269
```

```
<212> TYPE: PRT
<213> ORGANISM: Candida albicans

<400> SEQUENCE: 9

Asp Thr Trp Ile Lys Leu Gly Asn Thr Ile Leu Ser Val Glu Pro Thr
1               5                   10                  15

His Asn Phe Tyr Leu Lys Asp Ser Lys Ser Ser Leu Ile Val His Ala
            20                  25                  30

Val Ser Ser Asn Gln Thr Phe Thr Val His Gly Phe Gly Asn Gly Asn
        35                  40                  45

Lys Leu Gly Leu Thr Leu Pro Leu Thr Gly Asn Arg Asp His Phe Arg
    50                  55                  60

Phe Glu Tyr Tyr Pro Asp Thr Gly Ile Leu Gln Leu Arg Ala Asp Ala
65              70                  75                  80

Leu Pro Gln Tyr Phe Lys Ile Gly Lys Gly Tyr Asp Ser Lys Leu Phe
            85                  90                  95

Arg Ile Val Asn Ser Arg Gly Leu Lys Asn Ala Val Thr Tyr Asp Gly
        100                 105                 110

Pro Val Pro Asn Asn Glu Ile Pro Ala Val Cys Leu Ile Pro Cys Thr
    115                 120                 125

Asn Gly Pro Ser Ala Pro Glu Ser Glu Ser Asp Leu Asn Thr Pro Thr
130                 135                 140

Thr Ser Ser Ile Glu Thr Ser Ser Tyr Ser Ser Ala Ala Thr Glu Ser
145                 150                 155                 160

Ser Val Val Ser Glu Ser Ser Ala Val Asp Ser Leu Thr Ser Ser
            165                 170                 175

Ser Leu Ser Ser Lys Ser Glu Ser Ser Asp Val Val Ser Ser Thr Thr
        180                 185                 190

Asn Ile Glu Ser Ser Ser Thr Ala Ile Glu Thr Thr Met Asn Ser Glu
    195                 200                 205

Ser Ser Thr Asp Ala Gly Ser Ser Ser Ile Ser Gln Ser Glu Ser Ser
210                 215                 220

Ser Thr Ala Ile Thr Ser Ser Glu Thr Ser Ser Ser Glu Ser Met Ser
225                 230                 235                 240

Ser Ala Ser Ser Thr Thr Ala Ser Asn Thr Ser Ile Glu Thr Asp Ser
            245                 250                 255

Gly Ile Val Ser Gln Ser Glu Ser Ser Ser Asn Ala Leu
        260                 265

<210> SEQ ID NO 10
<211> LENGTH: 119
<212> TYPE: PRT
<213> ORGANISM: Candida albicans

<400> SEQUENCE: 10

Ser Ser Tyr Ser Ser Ala Ala Thr Glu Ser Ser Val Val Ser Glu Ser
1               5                   10                  15

Ser Ser Ala Val Asp Ser Leu Thr Ser Ser Ser Leu Ser Ser Lys Ser
            20                  25                  30

Glu Ser Ser Asp Val Val Ser Ser Thr Thr Asn Ile Glu Ser Ser Ser
        35                  40                  45

Thr Ala Ile Glu Thr Thr Met Asn Ser Glu Ser Ser Thr Asp Ala Gly
    50                  55                  60

Ser Ser Ser Ile Ser Gln Ser Glu Ser Ser Ser Thr Ala Ile Thr Ser
65              70                  75                  80
```

Ser Ser Glu Thr Ser Ser Ser Glu Ser Met Ser Ala Ser Ser Thr Thr
            85                  90                  95

Ala Ser Asn Thr Ser Ile Glu Thr Asp Ser Gly Ile Val Ser Gln Ser
            100                 105                 110

Glu Ser Ser Ser Asn Ala Leu
        115

<210> SEQ ID NO 11
<211> LENGTH: 741
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (415)..(416)
<223> OTHER INFORMATION: Residues at these positions may or may not be
      separated by an undisclosed linker peptide

<400> SEQUENCE: 11

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

```
Ala Pro Phe Thr Leu Arg Trp Thr Gly Tyr Arg Asn Ser Asp Ala Gly
    290                 295                 300

Ser Asn Gly Ile Val Ile Val Ala Thr Thr Arg Thr Val Thr Asp Ser
305                 310                 315                 320

Thr Thr Ala Val Thr Thr Leu Pro Phe Asp Pro Asn Arg Asp Lys Thr
                325                 330                 335

Lys Thr Ile Glu Ile Leu Lys Pro Ile Pro Thr Thr Ile Thr Thr
                340                 345                 350

Ser Tyr Val Gly Val Thr Ser Tyr Ser Thr Lys Thr Ala Pro Ile
                355                 360                 365

Gly Glu Thr Ala Thr Val Ile Val Asp Ile Pro Tyr His Thr Thr Thr
    370                 375                 380

Thr Val Thr Ser Lys Trp Thr Gly Thr Ile Thr Ser Thr Thr Thr His
385                 390                 395                 400

Thr Asn Pro Thr Asp Ser Ile Asp Thr Val Ile Val Gln Val Pro Thr
                405                 410                 415

Ser Arg Ile Asp Arg Gly Gly Ile Gln Gly Phe His Gly Asp Val Lys
                420                 425                 430

Val His Ser Gly Ala Thr Trp Ala Ile Leu Gly Thr Thr Leu Cys Ser
    435                 440                 445

Phe Phe Gly Gly Leu Glu Val Glu Lys Gly Ala Ser Leu Phe Ile Lys
    450                 455                 460

Ser Asp Asn Gly Pro Val Leu Ala Leu Asn Val Ala Leu Ser Thr Leu
465                 470                 475                 480

Val Arg Pro Val Ile Asn Asn Gly Val Ile Ser Leu Asn Ser Lys Ser
                485                 490                 495

Ser Thr Ser Phe Ser Asn Phe Asp Ile Gly Gly Ser Ser Phe Thr Asn
                500                 505                 510

Asn Gly Glu Ile Tyr Leu Asp Ser Ser Gly Leu Val Lys Ser Thr Ala
    515                 520                 525

Tyr Leu Tyr Ala Arg Glu Trp Thr Asn Asn Gly Leu Ile Val Ala Tyr
    530                 535                 540

Gln Asn Gln Lys Ala Ala Gly Asn Ile Ala Phe Gly Thr Ala Tyr Gln
545                 550                 555                 560

Thr Ile Thr Asn Asn Gly Gln Ile Cys Leu Arg His Gln Asp Phe Val
                565                 570                 575

Pro Ala Thr Lys Ile Lys Gly Thr Gly Cys Val Thr Ala Asp Glu Asp
                580                 585                 590

Thr Trp Ile Lys Leu Gly Asn Thr Ile Leu Ser Val Glu Pro Thr His
    595                 600                 605

Asn Phe Tyr Leu Lys Asp Ser Lys Ser Ser Leu Ile Val His Ala Val
    610                 615                 620

Ser Ser Asn Gln Thr Phe Thr Val His Gly Phe Gly Asn Gly Asn Lys
625                 630                 635                 640

Leu Gly Leu Thr Leu Pro Leu Thr Gly Asn Arg Asp His Phe Arg Phe
                645                 650                 655

Glu Tyr Tyr Pro Asp Thr Gly Ile Leu Gln Leu Arg Ala Asp Ala Leu
                660                 665                 670

Pro Gln Tyr Phe Lys Ile Gly Lys Gly Tyr Asp Ser Lys Leu Phe Arg
                675                 680                 685

Ile Val Asn Ser Arg Gly Leu Lys Asn Ala Val Thr Tyr Asp Gly Pro
    690                 695                 700

Val Pro Asn Asn Glu Ile Pro Ala Val Cys Leu Ile Pro Cys Thr Asn
```

```
705                 710                 715                 720
Gly Pro Ser Ala Pro Glu Ser Glu Ser Asp Leu Asn Thr Pro Thr Thr
                725                 730                 735

Ser Ser Ile Glu Thr
            740

<210> SEQ ID NO 12
<211> LENGTH: 741
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

Ser Asn Gly Ile Val Ile Val Ala Thr Thr Arg Thr Val Thr Asp Ser
305                 310                 315                 320
```

```
Thr Thr Ala Val Thr Thr Leu Pro Phe Asp Pro Asn Arg Asp Lys Thr
                325                 330                 335

Lys Thr Ile Glu Ile Leu Lys Pro Ile Pro Thr Thr Thr Ile Thr Thr
            340                 345                 350

Ser Tyr Val Gly Val Thr Thr Ser Tyr Ser Lys Thr Ala Pro Ile
        355                 360                 365

Gly Glu Thr Ala Thr Val Ile Val Asp Ile Pro Tyr His Thr Thr Thr
        370                 375                 380

Thr Val Thr Ser Lys Trp Thr Gly Thr Ile Thr Ser Thr Thr Thr His
385                 390                 395                 400

Thr Asn Pro Thr Asp Ser Ile Asp Thr Val Ile Val Gln Val Pro Thr
                405                 410                 415

Ser Arg Ile Asp Arg Gly Gly Ile Gln Gly Phe His Gly Asp Val Lys
                420                 425                 430

Val His Ser Gly Ala Thr Trp Ala Ile Leu Gly Thr Thr Leu Cys Ser
            435                 440                 445

Phe Phe Gly Gly Leu Glu Val Glu Lys Gly Ala Ser Leu Phe Ile Lys
    450                 455                 460

Ser Asp Asn Gly Pro Val Leu Ala Leu Asn Val Ala Leu Ser Thr Leu
465                 470                 475                 480

Val Arg Pro Val Ile Asn Asn Gly Val Ile Ser Leu Asn Ser Lys Ser
                485                 490                 495

Ser Thr Ser Phe Ser Asn Phe Asp Ile Gly Ser Ser Phe Thr Asn
        500                 505                 510

Asn Gly Glu Ile Tyr Leu Asp Ser Ser Gly Leu Val Lys Ser Thr Ala
        515                 520                 525

Tyr Leu Tyr Ala Arg Glu Trp Thr Asn Asn Gly Leu Ile Val Ala Tyr
    530                 535                 540

Gln Asn Gln Lys Ala Ala Gly Asn Ile Ala Phe Gly Thr Ala Tyr Gln
545                 550                 555                 560

Thr Ile Thr Asn Asn Gly Gln Ile Cys Leu Arg His Gln Asp Phe Val
                565                 570                 575

Pro Ala Thr Lys Ile Lys Gly Thr Gly Cys Val Thr Ala Asp Glu Asp
                580                 585                 590

Thr Trp Ile Lys Leu Gly Asn Thr Ile Leu Ser Val Glu Pro Thr His
            595                 600                 605

Asn Phe Tyr Leu Lys Asp Ser Lys Ser Ser Leu Ile Val His Ala Val
        610                 615                 620

Ser Ser Asn Gln Thr Phe Thr Val His Gly Phe Gly Asn Gly Asn Lys
625                 630                 635                 640

Leu Gly Leu Thr Leu Pro Leu Thr Gly Asn Arg Asp His Phe Arg Phe
                645                 650                 655

Glu Tyr Tyr Pro Asp Thr Gly Ile Leu Gln Leu Arg Ala Asp Ala Leu
                660                 665                 670

Pro Gln Tyr Phe Lys Ile Gly Lys Gly Tyr Asp Ser Lys Leu Phe Arg
            675                 680                 685

Ile Val Asn Ser Arg Gly Leu Lys Asn Ala Val Thr Tyr Asp Gly Pro
        690                 695                 700

Val Pro Asn Asn Glu Ile Pro Ala Val Cys Leu Ile Pro Cys Thr Asn
705                 710                 715                 720

Gly Pro Ser Ala Pro Glu Ser Glu Ser Asp Leu Asn Thr Pro Thr Thr
                725                 730                 735

Ser Ser Ile Glu Thr
```

```
                            740

<210> SEQ ID NO 13
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (307)..(308)
<223> OTHER INFORMATION: Residues at these positions may or may not be
      separated by an undisclosed linker peptide

<400> SEQUENCE: 13

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

Ser Asn Gly Thr Ser Arg Ile Asp Arg Gly Ile Gln Gly Phe His
305                 310                 315                 320

Gly Asp Val Lys Val His Ser Gly Ala Thr Trp Ala Ile Leu Gly Thr
```

```
                    325                 330                 335
Thr Leu Cys Ser Phe Phe Gly Gly Leu Glu Val Glu Lys Gly Ala Ser
                340                 345                 350

Leu Phe Ile Lys Ser Asp Asn Gly Pro Val Leu Ala Leu Asn Val Ala
            355                 360                 365

Leu Ser Thr Leu Val Arg Pro Val Ile Asn Asn Gly Val Ile Ser Leu
        370                 375                 380

Asn Ser Lys Ser Ser Thr Ser Phe Ser Asn Phe Asp Ile Gly Gly Ser
385                 390                 395                 400

Ser Phe Thr Asn Asn Gly Glu Ile Tyr Leu Asp Ser Ser Gly Leu Val
                405                 410                 415

Lys Ser Thr Ala Tyr Leu Tyr Ala Arg Glu Trp Thr Asn Asn Gly Leu
            420                 425                 430

Ile Val Ala Tyr Gln Asn Gln Lys Ala Ala Gly Asn Ile Ala Phe Gly
        435                 440                 445

Thr Ala Tyr Gln Thr Ile Thr Asn Asn Gly Gln Ile Cys Leu Arg His
    450                 455                 460

Gln Asp Phe Val Pro Ala Thr Lys Ile Lys Gly Thr Gly Cys Val Thr
465                 470                 475                 480

Ala Asp Glu Asp Thr Trp Ile Lys Leu Gly Asn Thr Ile Leu Ser Val
                485                 490                 495

Glu Pro Thr His Asn Phe Tyr Leu Lys Asp Ser Lys Ser Ser Leu Ile
            500                 505                 510

Val His Ala Val Ser Ser Asn Gln Thr Phe Thr Val His Gly Phe Gly
        515                 520                 525

Asn Gly Asn Lys Leu Gly Leu Thr Leu Pro Leu Thr Gly Asn Arg Asp
    530                 535                 540

His Phe Arg Phe Glu Tyr Tyr Pro Asp Thr Gly Ile Leu Gln Leu Arg
545                 550                 555                 560

Ala Asp Ala Leu Pro Gln Tyr Phe Lys Ile Gly Lys Gly Tyr Asp Ser
                565                 570                 575

Lys Leu Phe Arg Ile Val Asn Ser Arg Gly Leu Lys Asn Ala Val Thr
            580                 585                 590

Tyr Asp Gly Pro Val Pro Asn Asn Glu Ile Pro Ala Val Cys Leu Ile
        595                 600                 605

Pro Cys Thr Asn Gly Pro Ser Ala Pro Glu Ser Glu Ser Asp Leu Asn
    610                 615                 620

Thr Pro Thr Thr Ser Ser Ile Glu Thr
625                 630

<210> SEQ ID NO 14
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45
```

```
Thr Phe Thr Leu Asn Met Pro Cys Val Phe Lys Phe Thr Thr Ser Gln
 50                  55                      60

Thr Ser Val Asp Leu Thr Ala His Gly Val Lys Tyr Ala Thr Cys Gln
 65                      70              75                      80

Phe Gln Ala Gly Glu Glu Phe Met Thr Phe Ser Thr Leu Thr Cys Thr
                     85                  90                  95

Val Ser Asn Thr Leu Thr Pro Ser Ile Lys Ala Leu Gly Thr Val Thr
                100                 105                 110

Leu Pro Leu Ala Phe Asn Val Gly Gly Thr Gly Ser Ser Val Asp Leu
            115                 120                 125

Glu Asp Ser Lys Cys Phe Thr Ala Gly Thr Asn Thr Val Thr Phe Asn
130                     135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
                180                 185                 190

Thr Ser Gly Thr Met Gly Phe Ala Asn Thr Tyr Gly Asp Val Gln Ile
            195                 200                 205

Asp Cys Ser Asn Ile His Val Gly Ile Thr Lys Gly Leu Asn Asp Trp
210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
                260                 265                 270

Leu Ser Tyr Ala Asn Glu Tyr Thr Cys Ala Gly Gly Tyr Trp Gln Arg
            275                 280                 285

Ala Pro Phe Thr Leu Arg Trp Thr Gly Tyr Arg Asn Ser Asp Ala Gly
290                 295                 300

Ser Asn Gly Thr Ser Arg Ile Asp Arg Gly Ile Gln Gly Phe His
305                 310                 315                 320

Gly Asp Val Lys Val His Ser Gly Ala Thr Trp Ala Ile Leu Gly Thr
                325                 330                 335

Thr Leu Cys Ser Phe Phe Gly Gly Leu Glu Val Glu Lys Gly Ala Ser
            340                 345                 350

Leu Phe Ile Lys Ser Asp Asn Gly Pro Val Leu Ala Leu Asn Val Ala
            355                 360                 365

Leu Ser Thr Leu Val Arg Pro Val Ile Asn Asn Gly Val Ile Ser Leu
370                 375                 380

Asn Ser Lys Ser Ser Thr Ser Phe Ser Asn Phe Asp Ile Gly Gly Ser
385                 390                 395                 400

Ser Phe Thr Asn Asn Gly Glu Ile Tyr Leu Asp Ser Ser Gly Leu Val
                405                 410                 415

Lys Ser Thr Ala Tyr Leu Tyr Ala Arg Glu Trp Thr Asn Asn Gly Leu
                420                 425                 430

Ile Val Ala Tyr Gln Asn Gln Lys Ala Ala Gly Asn Ile Ala Phe Gly
            435                 440                 445

Thr Ala Tyr Gln Thr Ile Thr Asn Asn Gly Gln Ile Cys Leu Arg His
450                 455                 460

Gln Asp Phe Val Pro Ala Thr Lys Ile Lys Gly Thr Gly Cys Val Thr
```

```
                465                 470                 475                 480
Ala Asp Glu Asp Thr Trp Ile Lys Leu Gly Asn Thr Ile Leu Ser Val
                        485                 490                 495

Glu Pro Thr His Asn Phe Tyr Leu Lys Asp Ser Lys Ser Ser Leu Ile
                500                 505                 510

Val His Ala Val Ser Ser Asn Gln Thr Phe Thr Val His Gly Phe Gly
            515                 520                 525

Asn Gly Asn Lys Leu Gly Leu Thr Leu Pro Leu Thr Gly Asn Arg Asp
        530                 535                 540

His Phe Arg Phe Glu Tyr Tyr Pro Asp Thr Gly Ile Leu Gln Leu Arg
545                 550                 555                 560

Ala Asp Ala Leu Pro Gln Tyr Phe Lys Ile Gly Lys Gly Tyr Asp Ser
                565                 570                 575

Lys Leu Phe Arg Ile Val Asn Ser Arg Gly Leu Lys Asn Ala Val Thr
                580                 585                 590

Tyr Asp Gly Pro Val Pro Asn Asn Glu Ile Pro Ala Val Cys Leu Ile
            595                 600                 605

Pro Cys Thr Asn Gly Pro Ser Ala Pro Glu Ser Glu Ser Asp Leu Asn
        610                 615                 620

Thr Pro Thr Thr Ser Ser Ile Glu Thr
625                 630

<210> SEQ ID NO 15
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (307)..(308)
<223> OTHER INFORMATION: Residues at these positions may or may not be
      separated by an undisclosed linker peptide

<400> SEQUENCE: 15

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
                20                  25                  30

Ala Val Leu Gly Trp Ser Leu Asp Gly Thr Ser Ala Ser Pro Gly Asp
            35                  40                  45

Thr Phe Thr Leu Asn Met Pro Cys Val Phe Lys Phe Thr Thr Ser Gln
        50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
                100                 105                 110

Leu Pro Leu Ala Phe Asn Val Gly Gly Thr Gly Ser Ser Val Asp Leu
            115                 120                 125

Glu Asp Ser Lys Cys Phe Thr Ala Gly Thr Asn Thr Val Thr Phe Asn
        130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
```

165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
            195                 200                 205

Asp Cys Ser Asn Ile His Val Gly Ile Thr Lys Gly Leu Asn Asp Trp
        210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
            245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
            275                 280                 285

Ala Pro Phe Thr Leu Arg Trp Thr Gly Tyr Arg Asn Ser Asp Ala Gly
            290                 295                 300

Ser Asn Gly Gln Asn Gln Lys Ala Ala Gly Asn Ile Ala Phe Gly Thr
305                 310                 315                 320

Ala Tyr Gln Thr Ile Thr Asn Asn Gly Gln Ile Cys Leu Arg His Gln
                325                 330                 335

Asp Phe Val Pro Ala Thr Lys Ile Lys Gly Thr Gly Cys Val Thr Ala
            340                 345                 350

Asp Glu Asp Thr Trp Ile Lys Leu Gly Asn Thr Ile Leu Ser Val Glu
            355                 360                 365

Pro Thr His Asn Phe Tyr Leu Lys Asp Ser Lys Ser Ser Leu Ile Val
        370                 375                 380

His Ala Val Ser Ser Asn Gln Thr Phe Thr Val His Gly Phe Gly Asn
385                 390                 395                 400

Gly Asn Lys Leu Gly Leu Thr Leu Pro Leu Thr Gly Asn Arg Asp His
                405                 410                 415

Phe Arg Phe Glu Tyr Tyr Pro Asp Thr Gly Ile Leu Gln Leu Arg Ala
            420                 425                 430

Asp Ala Leu Pro Gln Tyr Phe Lys Ile Gly Lys Gly Tyr Asp Ser Lys
            435                 440                 445

Leu Phe Arg Ile Val Asn Ser Arg Gly Leu Lys Asn Ala Val Thr Tyr
        450                 455                 460

Asp Gly Pro Val Pro Asn Asn Glu Ile Pro Ala Val Cys Leu Ile Pro
465                 470                 475                 480

Cys Thr Asn Gly Pro Ser Ala Pro Glu Ser Glu Ser Asp Leu Asn Thr
                485                 490                 495

Pro Thr Thr Ser Ser Ile Glu Thr
            500

<210> SEQ ID NO 16
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Lys Thr Ile Thr Gly Val Phe Asn Ser Phe Asn Ser Leu Thr Trp Ser
1               5                   10                  15

```
Asn Ala Ala Thr Tyr Asn Tyr Lys Gly Pro Gly Thr Pro Trp Asn
             20                  25                  30

Ala Val Leu Gly Trp Ser Leu Asp Gly Thr Ser Ala Ser Pro Gly Asp
         35                  40                  45

Thr Phe Thr Leu Asn Met Pro Cys Val Phe Lys Phe Thr Thr Ser Gln
     50                  55                  60

Thr Ser Val Asp Leu Thr Ala His Gly Val Lys Tyr Ala Thr Cys Gln
 65              70                  75                      80

Phe Gln Ala Gly Glu Glu Phe Met Thr Phe Ser Thr Leu Thr Cys Thr
                 85                  90                  95

Val Ser Asn Thr Leu Thr Pro Ser Ile Lys Ala Leu Gly Thr Val Thr
            100                 105                 110

Leu Pro Leu Ala Phe Asn Val Gly Thr Gly Ser Ser Val Asp Leu
        115                 120                 125

Glu Asp Ser Lys Cys Phe Thr Ala Gly Thr Asn Thr Val Thr Phe Asn
        130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

Ser Asn Gly Gln Asn Gln Lys Ala Ala Gly Asn Ile Ala Phe Gly Thr
305                 310                 315                 320

Ala Tyr Gln Thr Ile Thr Asn Asn Gly Gln Ile Cys Leu Arg His Gln
                325                 330                 335

Asp Phe Val Pro Ala Thr Lys Ile Lys Gly Thr Gly Cys Val Thr Ala
            340                 345                 350

Asp Glu Asp Thr Trp Ile Lys Leu Gly Asn Thr Ile Leu Ser Val Glu
        355                 360                 365

Pro Thr His Asn Phe Tyr Leu Lys Asp Ser Lys Ser Ser Leu Ile Val
    370                 375                 380

His Ala Val Ser Ser Asn Gln Thr Phe Thr Val His Gly Phe Gly Asn
385                 390                 395                 400

Gly Asn Lys Leu Gly Leu Thr Leu Pro Leu Thr Gly Asn Arg Asp His
                405                 410                 415

Phe Arg Phe Glu Tyr Tyr Pro Asp Thr Gly Ile Leu Gln Leu Arg Ala
            420                 425                 430

Asp Ala Leu Pro Gln Tyr Phe Lys Ile Gly Lys Gly Tyr Asp Ser Lys
```

-continued

```
                435                 440                 445
Leu Phe Arg Ile Val Asn Ser Arg Gly Leu Lys Asn Ala Val Thr Tyr
    450                 455                 460

Asp Gly Pro Val Pro Asn Asn Glu Ile Pro Ala Val Cys Leu Ile Pro
465                 470                 475                 480

Cys Thr Asn Gly Pro Ser Ala Pro Glu Ser Glu Ser Asp Leu Asn Thr
                485                 490                 495

Pro Thr Thr Ser Ser Ile Glu Thr
            500
```

<210> SEQ ID NO 17
<211> LENGTH: 741
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (326)..(327)
<223> OTHER INFORMATION: Residues at these positions may or may not be
      separated by an undisclosed linker peptide

<400> SEQUENCE: 17

```
Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
            20                  25                  30

Ser Phe Phe Gly Gly Leu Glu Val Glu Lys Gly Ala Ser Leu Phe Ile
        35                  40                  45

Lys Ser Asp Asn Gly Pro Val Leu Ala Leu Asn Val Ala Leu Ser Thr
    50                  55                  60

Leu Val Arg Pro Val Ile Asn Asn Gly Val Ile Ser Leu Asn Ser Lys
65                  70                  75                  80

Ser Ser Thr Ser Phe Ser Asn Phe Asp Ile Gly Gly Ser Ser Phe Thr
                85                  90                  95

Asn Asn Gly Glu Ile Tyr Leu Asp Ser Ser Gly Leu Val Lys Ser Thr
            100                 105                 110

Ala Tyr Leu Tyr Ala Arg Glu Trp Thr Asn Asn Gly Leu Ile Val Ala
        115                 120                 125

Tyr Gln Asn Gln Lys Ala Ala Gly Asn Ile Ala Phe Gly Thr Ala Tyr
    130                 135                 140

Gln Thr Ile Thr Asn Asn Gly Gln Ile Cys Leu Arg His Gln Asp Phe
145                 150                 155                 160

Val Pro Ala Thr Lys Ile Lys Gly Thr Gly Cys Val Thr Ala Asp Glu
                165                 170                 175

Asp Thr Trp Ile Lys Leu Gly Asn Thr Ile Leu Ser Val Glu Pro Thr
            180                 185                 190

His Asn Phe Tyr Leu Lys Asp Ser Lys Ser Ser Leu Ile Val His Ala
        195                 200                 205

Val Ser Ser Asn Gln Thr Phe Thr Val His Gly Phe Gly Asn Gly Asn
    210                 215                 220

Lys Leu Gly Leu Thr Leu Pro Leu Thr Gly Asn Arg Asp His Phe Arg
225                 230                 235                 240

Phe Glu Tyr Tyr Pro Asp Thr Gly Ile Leu Gln Leu Arg Ala Asp Ala
                245                 250                 255

Leu Pro Gln Tyr Phe Lys Ile Gly Lys Gly Tyr Asp Ser Lys Leu Phe
```

```
            260                 265                 270
Arg Ile Val Asn Ser Arg Gly Leu Lys Asn Ala Val Thr Tyr Asp Gly
            275                 280                 285
Pro Val Pro Asn Asn Glu Ile Pro Ala Val Cys Leu Ile Pro Cys Thr
            290                 295                 300
Asn Gly Pro Ser Ala Pro Glu Ser Glu Ser Asp Leu Asn Thr Pro Thr
305                 310                 315                 320
Thr Ser Ser Ile Glu Thr Lys Thr Ile Thr Gly Val Phe Asn Ser Phe
            325                 330                 335
Asn Ser Leu Thr Trp Ser Asn Ala Ala Thr Tyr Asn Tyr Lys Gly Pro
            340                 345                 350
Gly Thr Pro Thr Trp Asn Ala Val Leu Gly Trp Ser Leu Asp Gly Thr
            355                 360                 365
Ser Ala Ser Pro Gly Asp Thr Phe Thr Leu Asn Met Pro Cys Val Phe
            370                 375                 380
Lys Phe Thr Thr Ser Gln Thr Ser Val Asp Leu Thr Ala His Gly Val
385                 390                 395                 400
Lys Tyr Ala Thr Cys Gln Phe Gln Ala Gly Glu Glu Phe Met Thr Phe
            405                 410                 415
Ser Thr Leu Thr Cys Thr Val Ser Asn Thr Leu Thr Pro Ser Ile Lys
            420                 425                 430
Ala Leu Gly Thr Val Thr Leu Pro Leu Ala Phe Asn Val Gly Gly Thr
            435                 440                 445
Gly Ser Ser Val Asp Leu Glu Asp Ser Lys Cys Phe Thr Ala Gly Thr
            450                 455                 460
Asn Thr Val Thr Phe Asn Asp Gly Gly Lys Lys Ile Ser Ile Asn Val
465                 470                 475                 480
Asp Phe Glu Arg Ser Asn Val Asp Pro Lys Gly Tyr Leu Thr Asp Ser
            485                 490                 495
Arg Val Ile Pro Ser Leu Asn Lys Val Ser Thr Leu Phe Val Ala Pro
            500                 505                 510
Gln Cys Ala Asn Gly Tyr Thr Ser Gly Thr Met Gly Phe Ala Asn Thr
            515                 520                 525
Tyr Gly Asp Val Gln Ile Asp Cys Ser Asn Ile His Val Gly Ile Thr
            530                 535                 540
Lys Gly Leu Asn Asp Trp Asn Tyr Pro Val Ser Ser Glu Ser Phe Ser
545                 550                 555                 560
Tyr Thr Lys Thr Cys Ser Ser Asn Gly Ile Phe Ile Thr Tyr Lys Asn
            565                 570                 575
Val Pro Ala Gly Tyr Arg Pro Phe Val Asp Ala Tyr Ile Ser Ala Thr
            580                 585                 590
Asp Val Asn Ser Tyr Thr Leu Ser Tyr Ala Asn Glu Tyr Thr Cys Ala
            595                 600                 605
Gly Gly Tyr Trp Gln Arg Ala Pro Phe Thr Leu Arg Trp Thr Gly Tyr
            610                 615                 620
Arg Asn Ser Asp Ala Gly Ser Asn Gly Ile Val Ile Val Ala Thr Thr
625                 630                 635                 640
Arg Thr Val Thr Asp Ser Thr Thr Ala Val Thr Thr Leu Pro Phe Asp
            645                 650                 655
Pro Asn Arg Asp Lys Thr Lys Thr Ile Glu Ile Leu Lys Pro Ile Pro
            660                 665                 670
Thr Thr Thr Ile Thr Thr Ser Tyr Val Gly Val Thr Thr Ser Tyr Ser
            675                 680                 685
```

```
Thr Lys Thr Ala Pro Ile Gly Glu Thr Ala Thr Val Ile Val Asp Ile
    690                 695                 700

Pro Tyr His Thr Thr Thr Val Thr Ser Lys Trp Thr Gly Thr Ile
705                 710                 715                 720

Thr Ser Thr Thr Thr His Thr Asn Pro Thr Asp Ser Ile Asp Thr Val
                725                 730                 735

Ile Val Gln Val Pro
            740

<210> SEQ ID NO 18
<211> LENGTH: 741
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
            20                  25                  30

Ser Phe Phe Gly Gly Leu Glu Val Glu Lys Gly Ala Ser Leu Phe Ile
        35                  40                  45

Lys Ser Asp Asn Gly Pro Val Leu Ala Leu Asn Val Ala Leu Ser Thr
    50                  55                  60

Leu Val Arg Pro Val Ile Asn Asn Gly Val Ile Ser Leu Asn Ser Lys
65                  70                  75                  80

Ser Ser Thr Ser Phe Ser Asn Phe Asp Ile Gly Gly Ser Ser Phe Thr
                85                  90                  95

Asn Asn Gly Glu Ile Tyr Leu Asp Ser Ser Gly Leu Val Lys Ser Thr
            100                 105                 110

Ala Tyr Leu Tyr Ala Arg Glu Trp Thr Asn Asn Gly Leu Ile Val Ala
        115                 120                 125

Tyr Gln Asn Gln Lys Ala Ala Gly Asn Ile Ala Phe Gly Thr Ala Tyr
130                 135                 140

Gln Thr Ile Thr Asn Asn Gly Gln Ile Cys Leu Arg His Gln Asp Phe
145                 150                 155                 160

Val Pro Ala Thr Lys Ile Lys Gly Thr Gly Cys Val Thr Ala Asp Glu
                165                 170                 175

Asp Thr Trp Ile Lys Leu Gly Asn Thr Ile Leu Ser Val Glu Pro Thr
            180                 185                 190

His Asn Phe Tyr Leu Lys Asp Ser Lys Ser Ser Leu Ile Val His Ala
        195                 200                 205

Val Ser Ser Asn Gln Thr Phe Thr Val His Gly Phe Gly Asn Gly Asn
    210                 215                 220

Lys Leu Gly Leu Thr Leu Pro Leu Thr Gly Asn Arg Asp His Phe Arg
225                 230                 235                 240

Phe Glu Tyr Tyr Pro Asp Thr Gly Ile Leu Gln Leu Arg Ala Asp Ala
                245                 250                 255

Leu Pro Gln Tyr Phe Lys Ile Gly Lys Gly Tyr Asp Ser Lys Leu Phe
            260                 265                 270

Arg Ile Val Asn Ser Arg Gly Leu Lys Asn Ala Val Thr Tyr Asp Gly
        275                 280                 285

Pro Val Pro Asn Asn Glu Ile Pro Ala Val Cys Leu Ile Pro Cys Thr
```

```
            290             295             300
Asn Gly Pro Ser Ala Pro Glu Ser Glu Ser Asp Leu Asn Thr Pro Thr
305             310             315             320
Thr Ser Ser Ile Glu Thr Lys Thr Ile Thr Gly Val Phe Asn Ser Phe
                325             330             335
Asn Ser Leu Thr Trp Ser Asn Ala Ala Thr Tyr Asn Tyr Lys Gly Pro
            340             345             350
Gly Thr Pro Thr Trp Asn Ala Val Leu Gly Trp Ser Leu Asp Gly Thr
            355             360             365
Ser Ala Ser Pro Gly Asp Thr Phe Thr Leu Asn Met Pro Cys Val Phe
370             375             380
Lys Phe Thr Thr Ser Gln Thr Ser Val Asp Leu Thr Ala His Gly Val
385             390             395             400
Lys Tyr Ala Thr Cys Gln Phe Gln Ala Gly Glu Glu Phe Met Thr Phe
                405             410             415
Ser Thr Leu Thr Cys Thr Val Ser Asn Thr Leu Thr Pro Ser Ile Lys
                420             425             430
Ala Leu Gly Thr Val Thr Leu Pro Leu Ala Phe Asn Val Gly Gly Thr
            435             440             445
Gly Ser Ser Val Asp Leu Glu Asp Ser Lys Cys Phe Thr Ala Gly Thr
            450             455             460
Asn Thr Val Thr Phe Asn Asp Gly Gly Lys Lys Ile Ser Ile Asn Val
465             470             475             480
Asp Phe Glu Arg Ser Asn Val Asp Pro Lys Gly Tyr Leu Thr Asp Ser
                485             490             495
Arg Val Ile Pro Ser Leu Asn Lys Val Ser Thr Leu Phe Val Ala Pro
                500             505             510
Gln Cys Ala Asn Gly Tyr Thr Ser Gly Thr Met Gly Phe Ala Asn Thr
                515             520             525
Tyr Gly Asp Val Gln Ile Asp Cys Ser Asn Ile His Val Gly Ile Thr
            530             535             540
Lys Gly Leu Asn Asp Trp Asn Tyr Pro Val Ser Ser Glu Ser Phe Ser
545             550             555             560
Tyr Thr Lys Thr Cys Ser Ser Asn Gly Ile Phe Ile Thr Tyr Lys Asn
                565             570             575
Val Pro Ala Gly Tyr Arg Pro Phe Val Asp Ala Tyr Ile Ser Ala Thr
            580             585             590
Asp Val Asn Ser Tyr Thr Leu Ser Tyr Ala Asn Glu Tyr Thr Cys Ala
            595             600             605
Gly Gly Tyr Trp Gln Arg Ala Pro Phe Thr Leu Arg Trp Thr Gly Tyr
            610             615             620
Arg Asn Ser Asp Ala Gly Ser Asn Gly Ile Val Ile Val Ala Thr Thr
625             630             635             640
Arg Thr Val Thr Asp Ser Thr Thr Ala Val Thr Thr Leu Pro Phe Asp
                645             650             655
Pro Asn Arg Asp Lys Thr Lys Thr Ile Glu Ile Leu Lys Pro Ile Pro
                660             665             670
Thr Thr Thr Ile Thr Thr Ser Tyr Val Gly Val Thr Ser Tyr Ser
            675             680             685
Thr Lys Thr Ala Pro Ile Gly Glu Thr Ala Thr Val Ile Val Asp Ile
            690             695             700
Pro Tyr His Thr Thr Thr Val Thr Ser Lys Trp Thr Gly Thr Ile
705             710             715             720
```

Thr Ser Thr Thr Thr His Thr Asn Pro Thr Asp Ser Ile Asp Thr Val
                725                 730                 735

Ile Val Gln Val Pro
            740

<210> SEQ ID NO 19
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (326)..(327)
<223> OTHER INFORMATION: Residues at these positions may or may not be
      separated by an undisclosed linker peptide

<400> SEQUENCE: 19

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
            20                  25                  30

Ser Phe Phe Gly Gly Leu Glu Val Glu Lys Gly Ala Ser Leu Phe Ile
        35                  40                  45

Lys Ser Asp Asn Gly Pro Val Leu Ala Leu Asn Val Ala Leu Ser Thr
    50                  55                  60

Leu Val Arg Pro Val Ile Asn Asn Gly Val Ile Ser Leu Asn Ser Lys
65                  70                  75                  80

Ser Ser Thr Ser Phe Ser Asn Phe Asp Ile Gly Gly Ser Ser Phe Thr
                85                  90                  95

Asn Asn Gly Glu Ile Tyr Leu Asp Ser Ser Gly Leu Val Lys Ser Thr
            100                 105                 110

Ala Tyr Leu Tyr Ala Arg Glu Trp Thr Asn Asn Gly Leu Ile Val Ala
        115                 120                 125

Tyr Gln Asn Gln Lys Ala Ala Gly Asn Ile Ala Phe Gly Thr Ala Tyr
    130                 135                 140

Gln Thr Ile Thr Asn Asn Gly Gln Ile Cys Leu Arg His Gln Asp Phe
145                 150                 155                 160

Val Pro Ala Thr Lys Ile Lys Gly Thr Gly Cys Val Thr Ala Asp Glu
                165                 170                 175

Asp Thr Trp Ile Lys Leu Gly Asn Thr Ile Leu Ser Val Glu Pro Thr
            180                 185                 190

His Asn Phe Tyr Leu Lys Asp Ser Lys Ser Ser Leu Ile Val His Ala
        195                 200                 205

Val Ser Ser Asn Gln Thr Phe Thr Val His Gly Phe Gly Asn Gly Asn
    210                 215                 220

Lys Leu Gly Leu Thr Leu Pro Leu Thr Gly Asn Arg Asp His Phe Arg
225                 230                 235                 240

Phe Glu Tyr Tyr Pro Asp Thr Gly Ile Leu Gln Leu Arg Ala Asp Ala
                245                 250                 255

Leu Pro Gln Tyr Phe Lys Ile Gly Lys Gly Tyr Asp Ser Lys Leu Phe
            260                 265                 270

Arg Ile Val Asn Ser Arg Gly Leu Lys Asn Ala Val Thr Tyr Asp Gly
        275                 280                 285

Pro Val Pro Asn Asn Glu Ile Pro Ala Val Cys Leu Ile Pro Cys Thr
    290                 295                 300

Asn Gly Pro Ser Ala Pro Glu Ser Glu Ser Asp Leu Asn Thr Pro Thr
305                 310                 315                 320

Thr Ser Ser Ile Glu Thr Lys Thr Ile Thr Gly Val Phe Asn Ser Phe
            325                 330                 335

Asn Ser Leu Thr Trp Ser Asn Ala Ala Thr Tyr Asn Tyr Lys Gly Pro
        340                 345                 350

Gly Thr Pro Thr Trp Asn Ala Val Leu Gly Trp Ser Leu Asp Gly Thr
    355                 360                 365

Ser Ala Ser Pro Gly Asp Thr Phe Thr Leu Asn Met Pro Cys Val Phe
370                 375                 380

Lys Phe Thr Thr Ser Gln Thr Ser Val Asp Leu Thr Ala His Gly Val
385                 390                 395                 400

Lys Tyr Ala Thr Cys Gln Phe Gln Ala Gly Glu Glu Phe Met Thr Phe
                405                 410                 415

Ser Thr Leu Thr Cys Thr Val Ser Asn Thr Leu Thr Pro Ser Ile Lys
            420                 425                 430

Ala Leu Gly Thr Val Thr Leu Pro Leu Ala Phe Asn Val Gly Gly Thr
        435                 440                 445

Gly Ser Ser Val Asp Leu Glu Asp Ser Lys Cys Phe Thr Ala Gly Thr
    450                 455                 460

Asn Thr Val Thr Phe Asn Asp Gly Gly Lys Lys Ile Ser Ile Asn Val
465                 470                 475                 480

Asp Phe Glu Arg Ser Asn Val Asp Pro Lys Gly Tyr Leu Thr Asp Ser
                485                 490                 495

Arg Val Ile Pro Ser Leu Asn Lys Val Ser Thr Leu Phe Val Ala Pro
            500                 505                 510

Gln Cys Ala Asn Gly Tyr Thr Ser Gly Thr Met Gly Phe Ala Asn Thr
        515                 520                 525

Tyr Gly Asp Val Gln Ile Asp Cys Ser Asn Ile His Val Gly Ile Thr
    530                 535                 540

Lys Gly Leu Asn Asp Trp Asn Tyr Pro Val Ser Ser Glu Ser Phe Ser
545                 550                 555                 560

Tyr Thr Lys Thr Cys Ser Ser Asn Gly Ile Phe Ile Thr Tyr Lys Asn
                565                 570                 575

Val Pro Ala Gly Tyr Arg Pro Phe Val Asp Ala Tyr Ile Ser Ala Thr
            580                 585                 590

Asp Val Asn Ser Tyr Thr Leu Ser Tyr Ala Asn Glu Tyr Thr Cys Ala
        595                 600                 605

Gly Gly Tyr Trp Gln Arg Ala Pro Phe Thr Leu Arg Trp Thr Gly Tyr
    610                 615                 620

Arg Asn Ser Asp Ala Gly Ser Asn Gly
625                 630

<210> SEQ ID NO 20
<211> LENGTH: 633
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys

-continued

```
                20                  25                  30
Ser Phe Phe Gly Gly Leu Glu Val Glu Lys Gly Ala Ser Leu Phe Ile
            35                  40                  45
Lys Ser Asp Asn Gly Pro Val Leu Ala Leu Asn Val Ala Leu Ser Thr
 50                  55                  60
Leu Val Arg Pro Val Ile Asn Asn Gly Val Ile Ser Leu Asn Ser Lys
 65                  70                  75                  80
Ser Ser Thr Ser Phe Ser Asn Phe Asp Ile Gly Gly Ser Ser Phe Thr
                85                  90                  95
Asn Asn Gly Glu Ile Tyr Leu Asp Ser Ser Gly Leu Val Lys Ser Thr
            100                 105                 110
Ala Tyr Leu Tyr Ala Arg Glu Trp Thr Asn Asn Gly Leu Ile Val Ala
            115                 120                 125
Tyr Gln Asn Gln Lys Ala Ala Gly Asn Ile Ala Phe Gly Thr Ala Tyr
            130                 135                 140
Gln Thr Ile Thr Asn Asn Gly Gln Ile Cys Leu Arg His Gln Asp Phe
145                 150                 155                 160
Val Pro Ala Thr Lys Ile Lys Gly Thr Gly Cys Val Thr Ala Asp Glu
            165                 170                 175
Asp Thr Trp Ile Lys Leu Gly Asn Thr Ile Leu Ser Val Glu Pro Thr
            180                 185                 190
His Asn Phe Tyr Leu Lys Asp Ser Lys Ser Ser Leu Ile Val His Ala
            195                 200                 205
Val Ser Ser Asn Gln Thr Phe Thr Val His Gly Phe Gly Asn Gly Asn
            210                 215                 220
Lys Leu Gly Leu Thr Leu Pro Leu Thr Gly Asn Arg Asp His Phe Arg
225                 230                 235                 240
Phe Glu Tyr Tyr Pro Asp Thr Gly Ile Leu Gln Leu Arg Ala Asp Ala
            245                 250                 255
Leu Pro Gln Tyr Phe Lys Ile Gly Lys Gly Tyr Asp Ser Lys Leu Phe
            260                 265                 270
Arg Ile Val Asn Ser Arg Gly Leu Lys Asn Ala Val Thr Tyr Asp Gly
            275                 280                 285
Pro Val Pro Asn Asn Glu Ile Pro Ala Val Cys Leu Ile Pro Cys Thr
            290                 295                 300
Asn Gly Pro Ser Ala Pro Glu Ser Glu Ser Asp Leu Asn Thr Pro Thr
305                 310                 315                 320
Thr Ser Ser Ile Glu Thr Lys Thr Ile Thr Gly Val Phe Asn Ser Phe
            325                 330                 335
Asn Ser Leu Thr Trp Ser Asn Ala Ala Thr Tyr Asn Tyr Lys Gly Pro
            340                 345                 350
Gly Thr Pro Thr Trp Asn Ala Val Leu Gly Trp Ser Leu Asp Gly Thr
            355                 360                 365
Ser Ala Ser Pro Gly Asp Thr Phe Thr Leu Asn Met Pro Cys Val Phe
            370                 375                 380
Lys Phe Thr Thr Ser Gln Thr Ser Val Asp Leu Thr Ala His Gly Val
385                 390                 395                 400
Lys Tyr Ala Thr Cys Gln Phe Gln Ala Gly Glu Glu Phe Met Thr Phe
            405                 410                 415
Ser Thr Leu Thr Cys Thr Val Ser Asn Thr Leu Thr Pro Ser Ile Lys
            420                 425                 430
Ala Leu Gly Thr Val Thr Leu Pro Leu Ala Phe Asn Val Gly Gly Thr
            435                 440                 445
```

```
Gly Ser Ser Val Asp Leu Glu Asp Ser Lys Cys Phe Thr Ala Gly Thr
        450                 455                 460

Asn Thr Val Thr Phe Asn Asp Gly Gly Lys Lys Ile Ser Ile Asn Val
465                 470                 475                 480

Asp Phe Glu Arg Ser Asn Val Asp Pro Lys Gly Tyr Leu Thr Asp Ser
                485                 490                 495

Arg Val Ile Pro Ser Leu Asn Lys Val Ser Thr Leu Phe Val Ala Pro
                500                 505                 510

Gln Cys Ala Asn Gly Tyr Thr Ser Gly Thr Met Gly Phe Ala Asn Thr
            515                 520                 525

Tyr Gly Asp Val Gln Ile Asp Cys Ser Asn Ile His Val Gly Ile Thr
        530                 535                 540

Lys Gly Leu Asn Asp Trp Asn Tyr Pro Val Ser Ser Glu Ser Phe Ser
545                 550                 555                 560

Tyr Thr Lys Thr Cys Ser Ser Asn Gly Ile Phe Ile Thr Tyr Lys Asn
                565                 570                 575

Val Pro Ala Gly Tyr Arg Pro Phe Val Asp Ala Tyr Ile Ser Ala Thr
            580                 585                 590

Asp Val Asn Ser Tyr Thr Leu Ser Tyr Ala Asn Glu Tyr Thr Cys Ala
        595                 600                 605

Gly Gly Tyr Trp Gln Arg Ala Pro Phe Thr Leu Arg Trp Thr Gly Tyr
    610                 615                 620

Arg Asn Ser Asp Ala Gly Ser Asn Gly
625                 630

<210> SEQ ID NO 21
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (197)..(198)
<223> OTHER INFORMATION: Residues at these positions may or may not be
      separated by an undisclosed linker peptide

<400> SEQUENCE: 21

Gln Asn Gln Lys Ala Ala Gly Asn Ile Ala Phe Gly Thr Ala Tyr Gln
1               5                   10                  15

Thr Ile Thr Asn Asn Gly Gln Ile Cys Leu Arg His Gln Asp Phe Val
                20                  25                  30

Pro Ala Thr Lys Ile Lys Gly Thr Gly Cys Val Thr Ala Asp Glu Asp
            35                  40                  45

Thr Trp Ile Lys Leu Gly Asn Thr Ile Leu Ser Val Glu Pro Thr His
        50                  55                  60

Asn Phe Tyr Leu Lys Asp Ser Lys Ser Ser Leu Ile Val His Ala Val
65                  70                  75                  80

Ser Ser Asn Gln Thr Phe Thr Val His Gly Phe Gly Asn Gly Asn Lys
                85                  90                  95

Leu Gly Leu Thr Leu Pro Leu Thr Gly Asn Arg Asp His Phe Arg Phe
                100                 105                 110

Glu Tyr Tyr Pro Asp Thr Gly Ile Leu Gln Leu Arg Ala Asp Ala Leu
            115                 120                 125

Pro Gln Tyr Phe Lys Ile Gly Lys Gly Tyr Asp Ser Lys Leu Phe Arg
        130                 135                 140
```

```
Ile Val Asn Ser Arg Gly Leu Lys Asn Ala Val Thr Tyr Asp Gly Pro
145                 150                 155                 160

Val Pro Asn Asn Glu Ile Pro Ala Val Cys Leu Ile Pro Cys Thr Asn
                165                 170                 175

Gly Pro Ser Ala Pro Glu Ser Glu Ser Asp Leu Asn Thr Pro Thr Thr
            180                 185                 190

Ser Ser Ile Glu Thr Lys Thr Ile Thr Gly Val Phe Asn Ser Phe Asn
        195                 200                 205

Ser Leu Thr Trp Ser Asn Ala Ala Thr Tyr Asn Tyr Lys Gly Pro Gly
        210                 215                 220

Thr Pro Thr Trp Asn Ala Val Leu Gly Trp Ser Leu Asp Gly Thr Ser
225                 230                 235                 240

Ala Ser Pro Gly Asp Thr Phe Thr Leu Asn Met Pro Cys Val Phe Lys
            245                 250                 255

Phe Thr Thr Ser Gln Thr Ser Val Asp Leu Thr Ala His Gly Val Lys
            260                 265                 270

Tyr Ala Thr Cys Gln Phe Gln Ala Gly Glu Glu Phe Met Thr Phe Ser
            275                 280                 285

Thr Leu Thr Cys Thr Val Ser Asn Thr Leu Thr Pro Ser Ile Lys Ala
            290                 295                 300

Leu Gly Thr Val Thr Leu Pro Leu Ala Phe Asn Val Gly Gly Thr Gly
305                 310                 315                 320

Ser Ser Val Asp Leu Glu Asp Ser Lys Cys Phe Thr Ala Gly Thr Asn
                325                 330                 335

Thr Val Thr Phe Asn Asp Gly Lys Lys Ile Ser Ile Asn Val Asp
                340                 345                 350

Phe Glu Arg Ser Asn Val Asp Pro Lys Gly Tyr Leu Thr Asp Ser Arg
            355                 360                 365

Val Ile Pro Ser Leu Asn Lys Val Ser Thr Leu Phe Val Ala Pro Gln
        370                 375                 380

Cys Ala Asn Gly Tyr Thr Ser Gly Thr Met Gly Phe Ala Asn Thr Tyr
385                 390                 395                 400

Gly Asp Val Gln Ile Asp Cys Ser Asn Ile His Val Gly Ile Thr Lys
                405                 410                 415

Gly Leu Asn Asp Trp Asn Tyr Pro Val Ser Ser Glu Ser Phe Ser Tyr
            420                 425                 430

Thr Lys Thr Cys Ser Ser Asn Gly Ile Phe Ile Thr Tyr Lys Asn Val
        435                 440                 445

Pro Ala Gly Tyr Arg Pro Phe Val Asp Ala Tyr Ile Ser Ala Thr Asp
    450                 455                 460

Val Asn Ser Tyr Thr Leu Ser Tyr Ala Asn Glu Tyr Thr Cys Ala Gly
465                 470                 475                 480

Gly Tyr Trp Gln Arg Ala Pro Phe Thr Leu Arg Trp Thr Gly Tyr Arg
            485                 490                 495

Asn Ser Asp Ala Gly Ser Asn Gly Ile Val Ile Val Ala Thr Thr Arg
            500                 505                 510

Thr Val Thr Asp Ser Thr Thr Ala Val Thr Thr Leu Pro Phe Asp Pro
            515                 520                 525

Asn Arg Asp Lys Thr Lys Thr Ile Glu Ile Leu Lys Pro Ile Pro Thr
            530                 535                 540

Thr Thr Ile Thr Thr Ser Tyr Val Gly Val Thr Thr Ser Tyr Ser Thr
545                 550                 555                 560
```

```
Lys Thr Ala Pro Ile Gly Glu Thr Ala Thr Val Ile Val Asp Ile Pro
            565                 570                 575

Tyr His Thr Thr Thr Thr Val Thr Ser Lys Trp Thr Gly Thr Ile Thr
            580                 585                 590

Ser Thr Thr Thr His Thr Asn Pro Thr Asp Ser Ile Asp Thr Val Ile
            595                 600                 605

Val Gln Val Pro
    610

<210> SEQ ID NO 22
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Asn Gln Lys Ala Ala Gly Asn Ile Ala Phe Gly Thr Ala Tyr Gln
1               5                   10                  15

Thr Ile Thr Asn Asn Gly Gln Ile Cys Leu Arg His Gln Asp Phe Val
            20                  25                  30

Pro Ala Thr Lys Ile Lys Gly Thr Gly Cys Val Thr Ala Asp Glu Asp
            35                  40                  45

Thr Trp Ile Lys Leu Gly Asn Thr Ile Leu Ser Val Glu Pro Thr His
    50                  55                  60

Asn Phe Tyr Leu Lys Asp Ser Lys Ser Ser Leu Ile Val His Ala Val
65                  70                  75                  80

Ser Ser Asn Gln Thr Phe Thr Val His Gly Phe Gly Asn Gly Asn Lys
                85                  90                  95

Leu Gly Leu Thr Leu Pro Leu Thr Gly Asn Arg Asp His Phe Arg Phe
            100                 105                 110

Glu Tyr Tyr Pro Asp Thr Gly Ile Leu Gln Leu Arg Ala Asp Ala Leu
            115                 120                 125

Pro Gln Tyr Phe Lys Ile Gly Lys Gly Tyr Asp Ser Lys Leu Phe Arg
    130                 135                 140

Ile Val Asn Ser Arg Gly Leu Lys Asn Ala Val Thr Tyr Asp Gly Pro
145                 150                 155                 160

Val Pro Asn Asn Glu Ile Pro Ala Val Cys Leu Ile Pro Cys Thr Asn
                165                 170                 175

Gly Pro Ser Ala Pro Glu Ser Glu Ser Asp Leu Asn Thr Pro Thr Thr
            180                 185                 190

Ser Ser Ile Glu Thr Lys Thr Ile Thr Gly Val Phe Asn Ser Phe Asn
            195                 200                 205

Ser Leu Thr Trp Ser Asn Ala Ala Thr Tyr Asn Tyr Lys Gly Pro Gly
    210                 215                 220

Thr Pro Thr Trp Asn Ala Val Leu Gly Trp Ser Leu Asp Gly Thr Ser
225                 230                 235                 240

Ala Ser Pro Gly Asp Thr Phe Thr Leu Asn Met Pro Cys Val Phe Lys
                245                 250                 255

Phe Thr Thr Ser Gln Thr Ser Val Asp Leu Thr Ala His Gly Val Lys
            260                 265                 270

Tyr Ala Thr Cys Gln Phe Gln Ala Gly Glu Glu Phe Met Thr Phe Ser
            275                 280                 285

Thr Leu Thr Cys Thr Val Ser Asn Thr Leu Thr Pro Ser Ile Lys Ala
    290                 295                 300
```

Leu Gly Thr Val Thr Leu Pro Leu Ala Phe Asn Val Gly Thr Gly
305                 310                 315                 320

Ser Ser Val Asp Leu Glu Asp Ser Lys Cys Phe Thr Ala Gly Thr Asn
            325                 330                 335

Thr Val Thr Phe Asn Asp Gly Lys Lys Ile Ser Ile Asn Val Asp
        340                 345                 350

Phe Glu Arg Ser Asn Val Asp Pro Lys Gly Tyr Leu Thr Asp Ser Arg
            355                 360                 365

Val Ile Pro Ser Leu Asn Lys Val Ser Thr Leu Phe Val Ala Pro Gln
    370                 375                 380

Cys Ala Asn Gly Tyr Thr Ser Gly Thr Met Gly Phe Ala Asn Thr Tyr
385                 390                 395                 400

Gly Asp Val Gln Ile Asp Cys Ser Asn Ile His Val Gly Ile Thr Lys
                405                 410                 415

Gly Leu Asn Asp Trp Asn Tyr Pro Val Ser Glu Ser Phe Ser Tyr
            420                 425                 430

Thr Lys Thr Cys Ser Ser Asn Gly Ile Phe Ile Thr Tyr Lys Asn Val
    435                 440                 445

Pro Ala Gly Tyr Arg Pro Phe Val Asp Ala Tyr Ile Ser Ala Thr Asp
    450                 455                 460

Val Asn Ser Tyr Thr Leu Ser Tyr Ala Asn Glu Tyr Thr Cys Ala Gly
465                 470                 475                 480

Gly Tyr Trp Gln Arg Ala Pro Phe Thr Leu Arg Trp Thr Gly Tyr Arg
                485                 490                 495

Asn Ser Asp Ala Gly Ser Asn Gly Ile Val Ile Val Ala Thr Thr Arg
            500                 505                 510

Thr Val Thr Asp Ser Thr Thr Ala Val Thr Thr Leu Pro Phe Asp Pro
        515                 520                 525

Asn Arg Asp Lys Thr Lys Thr Ile Glu Ile Leu Lys Pro Ile Pro Thr
    530                 535                 540

Thr Thr Ile Thr Thr Ser Tyr Val Gly Val Thr Ser Tyr Ser Thr
545                 550                 555                 560

Lys Thr Ala Pro Ile Gly Glu Thr Ala Thr Val Ile Val Asp Ile Pro
                565                 570                 575

Tyr His Thr Thr Thr Thr Val Thr Ser Lys Trp Thr Gly Thr Ile Thr
            580                 585                 590

Ser Thr Thr Thr His Thr Asn Pro Thr Asp Ser Ile Asp Thr Val Ile
        595                 600                 605

Val Gln Val Pro
    610

<210> SEQ ID NO 23
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (197)..(198)
<223> OTHER INFORMATION: Residues at these positions may or may not be
      separated by an undisclosed linker peptide

<400> SEQUENCE: 23

Gln Asn Gln Lys Ala Ala Gly Asn Ile Ala Phe Gly Thr Ala Tyr Gln
1               5                   10                  15

-continued

Thr Ile Thr Asn Asn Gly Gln Ile Cys Leu Arg His Gln Asp Phe Val
            20                  25                  30

Pro Ala Thr Lys Ile Lys Gly Thr Gly Cys Val Thr Ala Asp Glu Asp
            35                  40                  45

Thr Trp Ile Lys Leu Gly Asn Thr Ile Leu Ser Val Glu Pro Thr His
 50                  55                  60

Asn Phe Tyr Leu Lys Asp Ser Lys Ser Ser Leu Ile Val His Ala Val
 65                  70                  75                  80

Ser Ser Asn Gln Thr Phe Thr Val His Gly Phe Gly Asn Gly Asn Lys
                85                  90                  95

Leu Gly Leu Thr Leu Pro Leu Thr Gly Asn Arg Asp His Phe Arg Phe
            100                 105                 110

Glu Tyr Tyr Pro Asp Thr Gly Ile Leu Gln Leu Arg Ala Asp Ala Leu
            115                 120                 125

Pro Gln Tyr Phe Lys Ile Gly Lys Gly Tyr Asp Ser Lys Leu Phe Arg
            130                 135                 140

Ile Val Asn Ser Arg Gly Leu Lys Asn Ala Val Thr Tyr Asp Gly Pro
145                 150                 155                 160

Val Pro Asn Asn Glu Ile Pro Ala Val Cys Leu Ile Pro Cys Thr Asn
            165                 170                 175

Gly Pro Ser Ala Pro Glu Ser Glu Ser Asp Leu Asn Thr Pro Thr Thr
            180                 185                 190

Ser Ser Ile Glu Thr Lys Thr Ile Thr Gly Val Phe Asn Ser Phe Asn
            195                 200                 205

Ser Leu Thr Trp Ser Asn Ala Ala Thr Tyr Asn Tyr Lys Gly Pro Gly
210                 215                 220

Thr Pro Thr Trp Asn Ala Val Leu Gly Trp Ser Leu Asp Gly Thr Ser
225                 230                 235                 240

Ala Ser Pro Gly Asp Thr Phe Thr Leu Asn Met Pro Cys Val Phe Lys
            245                 250                 255

Phe Thr Thr Ser Gln Thr Ser Val Asp Leu Thr Ala His Gly Val Lys
            260                 265                 270

Tyr Ala Thr Cys Gln Phe Gln Ala Gly Glu Glu Phe Met Thr Phe Ser
            275                 280                 285

Thr Leu Thr Cys Thr Val Ser Asn Thr Leu Thr Pro Ser Ile Lys Ala
            290                 295                 300

Leu Gly Thr Val Thr Leu Pro Leu Ala Phe Asn Val Gly Gly Thr Gly
305                 310                 315                 320

Ser Ser Val Asp Leu Glu Asp Ser Lys Cys Phe Thr Ala Gly Thr Asn
            325                 330                 335

Thr Val Thr Phe Asn Asp Gly Lys Lys Ile Ser Ile Asn Val Asp
            340                 345                 350

Phe Glu Arg Ser Asn Val Asp Pro Lys Gly Tyr Leu Thr Asp Ser Arg
            355                 360                 365

Val Ile Pro Ser Leu Asn Lys Val Ser Thr Leu Phe Val Ala Pro Gln
            370                 375                 380

Cys Ala Asn Gly Tyr Thr Ser Gly Thr Met Gly Phe Ala Asn Thr Tyr
385                 390                 395                 400

Gly Asp Val Gln Ile Asp Cys Ser Asn Ile His Val Gly Ile Thr Lys
            405                 410                 415

Gly Leu Asn Asp Trp Asn Tyr Pro Val Ser Ser Glu Ser Phe Ser Tyr
            420                 425                 430

```
Thr Lys Thr Cys Ser Ser Asn Gly Ile Phe Ile Thr Tyr Lys Asn Val
            435                 440                 445

Pro Ala Gly Tyr Arg Pro Phe Val Asp Ala Tyr Ile Ser Ala Thr Asp
450                 455                 460

Val Asn Ser Tyr Thr Leu Ser Tyr Ala Asn Glu Tyr Thr Cys Ala Gly
465                 470                 475                 480

Gly Tyr Trp Gln Arg Ala Pro Phe Thr Leu Arg Trp Thr Gly Tyr Arg
                485                 490                 495

Asn Ser Asp Ala Gly Ser Asn Gly
            500

<210> SEQ ID NO 24
<211> LENGTH: 504
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Asn Gln Lys Ala Ala Gly Asn Ile Ala Phe Gly Thr Ala Tyr Gln
1               5                   10                  15

Thr Ile Thr Asn Asn Gly Gln Ile Cys Leu Arg His Gln Asp Phe Val
            20                  25                  30

Pro Ala Thr Lys Ile Lys Gly Thr Gly Cys Val Thr Ala Asp Glu Asp
            35                  40                  45

Thr Trp Ile Lys Leu Gly Asn Thr Ile Leu Ser Val Glu Pro Thr His
        50                  55                  60

Asn Phe Tyr Leu Lys Asp Ser Lys Ser Ser Leu Ile Val His Ala Val
65                  70                  75                  80

Ser Ser Asn Gln Thr Phe Thr Val His Gly Phe Gly Asn Gly Asn Lys
                85                  90                  95

Leu Gly Leu Thr Leu Pro Leu Thr Gly Asn Arg Asp His Phe Arg Phe
            100                 105                 110

Glu Tyr Tyr Pro Asp Thr Gly Ile Leu Gln Leu Arg Ala Asp Ala Leu
            115                 120                 125

Pro Gln Tyr Phe Lys Ile Gly Lys Gly Tyr Asp Ser Lys Leu Phe Arg
        130                 135                 140

Ile Val Asn Ser Arg Gly Leu Lys Asn Ala Val Thr Tyr Asp Gly Pro
145                 150                 155                 160

Val Pro Asn Asn Glu Ile Pro Ala Val Cys Leu Ile Pro Cys Thr Asn
                165                 170                 175

Gly Pro Ser Ala Pro Glu Ser Glu Ser Asp Leu Asn Thr Pro Thr Thr
            180                 185                 190

Ser Ser Ile Glu Thr Lys Thr Ile Thr Gly Val Phe Asn Ser Phe Asn
        195                 200                 205

Ser Leu Thr Trp Ser Asn Ala Ala Thr Asn Tyr Lys Gly Pro Gly
        210                 215                 220

Thr Pro Thr Trp Asn Ala Val Leu Gly Trp Ser Leu Asp Gly Thr Ser
225                 230                 235                 240

Ala Ser Pro Gly Asp Thr Phe Thr Leu Asn Met Pro Cys Val Phe Lys
                245                 250                 255

Phe Thr Thr Ser Gln Thr Ser Val Asp Leu Thr Ala His Gly Val Lys
            260                 265                 270

Tyr Ala Thr Cys Gln Phe Gln Ala Gly Glu Glu Phe Met Thr Phe Ser
        275                 280                 285
```

```
Thr Leu Thr Cys Thr Val Ser Asn Thr Leu Thr Pro Ser Ile Lys Ala
    290                 295                 300

Leu Gly Thr Val Thr Leu Pro Leu Ala Phe Asn Val Gly Gly Thr Gly
305                 310                 315                 320

Ser Ser Val Asp Leu Glu Asp Ser Lys Cys Phe Thr Ala Gly Thr Asn
                325                 330                 335

Thr Val Thr Phe Asn Asp Gly Lys Lys Ile Ser Ile Asn Val Asp
            340                 345                 350

Phe Glu Arg Ser Asn Val Asp Pro Lys Gly Tyr Leu Thr Asp Ser Arg
                355                 360                 365

Val Ile Pro Ser Leu Asn Lys Val Ser Thr Leu Phe Val Ala Pro Gln
            370                 375                 380

Cys Ala Asn Gly Tyr Thr Ser Gly Thr Met Gly Phe Ala Asn Thr Tyr
385                 390                 395                 400

Gly Asp Val Gln Ile Asp Cys Ser Asn Ile His Val Gly Ile Thr Lys
                405                 410                 415

Gly Leu Asn Asp Trp Asn Tyr Pro Val Ser Ser Glu Ser Phe Ser Tyr
                420                 425                 430

Thr Lys Thr Cys Ser Ser Asn Gly Ile Phe Ile Thr Tyr Lys Asn Val
            435                 440                 445

Pro Ala Gly Tyr Arg Pro Phe Val Asp Ala Tyr Ile Ser Ala Thr Asp
450                 455                 460

Val Asn Ser Tyr Thr Leu Ser Tyr Ala Asn Glu Tyr Thr Cys Ala Gly
465                 470                 475                 480

Gly Tyr Trp Gln Arg Ala Pro Phe Thr Leu Arg Trp Thr Gly Tyr Arg
                485                 490                 495

Asn Ser Asp Ala Gly Ser Asn Gly
            500
```

<210> SEQ ID NO 25
<211> LENGTH: 752
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: misc_feature
<222> LOCATION: (307)..(308)
<223> OTHER INFORMATION: Residues at these positions may or may not be separated by an undisclosed linker peptide

<400> SEQUENCE: 25

```
Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
                20                  25                  30

Ala Val Leu Gly Trp Ser Leu Asp Gly Thr Ser Ala Ser Pro Gly Asp
            35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110
```

```
Leu Pro Leu Ala Phe Asn Val Gly Gly Thr Gly Ser Ser Val Asp Leu
    115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
                180                 185                 190

Thr Ser Gly Thr Met Gly Phe Ala Asn Thr Tyr Gly Asp Val Gln Ile
                195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
                260                 265                 270

Leu Ser Tyr Ala Asn Glu Tyr Thr Cys Ala Gly Gly Tyr Trp Gln Arg
                275                 280                 285

Ala Pro Phe Thr Leu Arg Trp Thr Gly Tyr Arg Asn Ser Asp Ala Gly
                290                 295                 300

Ser Asn Gly Thr Ser Arg Ile Asp Arg Gly Ile Gln Gly Phe His
305                 310                 315                 320

Gly Asp Val Lys Val His Ser Gly Ala Thr Trp Ala Ile Leu Gly Thr
                325                 330                 335

Thr Leu Cys Ser Phe Phe Gly Gly Leu Glu Val Glu Lys Gly Ala Ser
                340                 345                 350

Leu Phe Ile Lys Ser Asp Asn Gly Pro Val Leu Ala Leu Asn Val Ala
                355                 360                 365

Leu Ser Thr Leu Val Arg Pro Val Ile Asn Asn Gly Val Ile Ser Leu
                370                 375                 380

Asn Ser Lys Ser Ser Thr Ser Phe Ser Asn Phe Asp Ile Gly Gly Ser
385                 390                 395                 400

Ser Phe Thr Asn Asn Gly Glu Ile Tyr Leu Asp Ser Ser Gly Leu Val
                405                 410                 415

Lys Ser Thr Ala Tyr Leu Tyr Ala Arg Glu Trp Thr Asn Asn Gly Leu
                420                 425                 430

Ile Val Ala Tyr Gln Asn Gln Lys Ala Ala Gly Asn Ile Ala Phe Gly
                435                 440                 445

Thr Ala Tyr Gln Thr Ile Thr Asn Asn Gly Gln Ile Cys Leu Arg His
                450                 455                 460

Gln Asp Phe Val Pro Ala Thr Lys Ile Lys Gly Thr Gly Cys Val Thr
465                 470                 475                 480

Ala Asp Glu Asp Thr Trp Ile Lys Leu Gly Asn Thr Ile Leu Ser Val
                485                 490                 495

Glu Pro Thr His Asn Phe Tyr Leu Lys Asp Ser Lys Ser Ser Leu Ile
                500                 505                 510

Val His Ala Val Ser Ser Asn Gln Thr Phe Thr Val His Gly Phe Gly
                515                 520                 525
```

```
Asn Gly Asn Lys Leu Gly Leu Thr Leu Pro Leu Thr Gly Asn Arg Asp
            530                 535                 540

His Phe Arg Phe Glu Tyr Tyr Pro Asp Thr Gly Ile Leu Gln Leu Arg
545                 550                 555                 560

Ala Asp Ala Leu Pro Gln Tyr Phe Lys Ile Gly Lys Gly Tyr Asp Ser
                565                 570                 575

Lys Leu Phe Arg Ile Val Asn Ser Arg Gly Leu Lys Asn Ala Val Thr
            580                 585                 590

Tyr Asp Gly Pro Val Pro Asn Asn Glu Ile Pro Ala Val Cys Leu Ile
                595                 600                 605

Pro Cys Thr Asn Gly Pro Ser Ala Pro Glu Ser Glu Ser Asp Leu Asn
610                 615                 620

Thr Pro Thr Thr Ser Ser Ile Glu Thr Ser Ser Tyr Ser Ser Ala Ala
625                 630                 635                 640

Thr Glu Ser Ser Val Val Ser Glu Ser Ser Ala Val Asp Ser Leu
                    645                 650                 655

Thr Ser Ser Ser Leu Ser Ser Lys Ser Glu Ser Ser Asp Val Val Ser
            660                 665                 670

Ser Thr Thr Asn Ile Glu Ser Ser Thr Ala Ile Glu Thr Thr Met
                675                 680             685

Asn Ser Glu Ser Ser Thr Asp Ala Gly Ser Ser Ser Ile Ser Gln Ser
690                 695                 700

Glu Ser Ser Ser Thr Ala Ile Thr Ser Ser Ser Glu Thr Ser Ser Ser
705                 710                 715                 720

Glu Ser Met Ser Ala Ser Ser Thr Thr Ala Ser Asn Thr Ser Ile Glu
                725                 730                 735

Thr Asp Ser Gly Ile Val Ser Gln Ser Glu Ser Ser Asn Ala Leu
                740                 745                 750

<210> SEQ ID NO 26
<211> LENGTH: 752
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140
```

```
Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
            165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
        210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
            245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
        290                 295                 300

Ser Asn Gly Thr Ser Arg Ile Asp Arg Gly Ile Gln Gly Phe His
305                 310                 315                 320

Gly Asp Val Lys Val His Ser Gly Ala Thr Trp Ala Ile Leu Gly Thr
            325                 330                 335

Thr Leu Cys Ser Phe Phe Gly Gly Leu Glu Val Glu Lys Gly Ala Ser
        340                 345                 350

Leu Phe Ile Lys Ser Asp Asn Gly Pro Val Leu Ala Leu Asn Val Ala
        355                 360                 365

Leu Ser Thr Leu Val Arg Pro Val Ile Asn Asn Gly Val Ile Ser Leu
        370                 375                 380

Asn Ser Lys Ser Ser Thr Ser Phe Ser Asn Phe Asp Ile Gly Gly Ser
385                 390                 395                 400

Ser Phe Thr Asn Asn Gly Glu Ile Tyr Leu Asp Ser Ser Gly Leu Val
            405                 410                 415

Lys Ser Thr Ala Tyr Leu Tyr Ala Arg Glu Trp Thr Asn Asn Gly Leu
        420                 425                 430

Ile Val Ala Tyr Gln Asn Gln Lys Ala Ala Gly Asn Ile Ala Phe Gly
        435                 440                 445

Thr Ala Tyr Gln Thr Ile Thr Asn Asn Gly Gln Ile Cys Leu Arg His
        450                 455                 460

Gln Asp Phe Val Pro Ala Thr Lys Ile Lys Gly Thr Gly Cys Val Thr
465                 470                 475                 480

Ala Asp Glu Asp Thr Trp Ile Lys Leu Gly Asn Thr Ile Leu Ser Val
            485                 490                 495

Glu Pro Thr His Asn Phe Tyr Leu Lys Asp Ser Lys Ser Ser Leu Ile
            500                 505                 510

Val His Ala Val Ser Ser Asn Gln Thr Phe Thr Val His Gly Phe Gly
        515                 520                 525

Asn Gly Asn Lys Leu Gly Leu Thr Leu Pro Leu Thr Gly Asn Arg Asp
        530                 535                 540

His Phe Arg Phe Glu Tyr Tyr Pro Asp Thr Gly Ile Leu Gln Leu Arg
545                 550                 555                 560
```

```
Ala Asp Ala Leu Pro Gln Tyr Phe Lys Ile Gly Lys Gly Tyr Asp Ser
            565                 570                 575

Lys Leu Phe Arg Ile Val Asn Ser Arg Gly Leu Lys Asn Ala Val Thr
        580                 585                 590

Tyr Asp Gly Pro Val Pro Asn Asn Glu Ile Pro Ala Val Cys Leu Ile
        595                 600                 605

Pro Cys Thr Asn Gly Pro Ser Ala Pro Glu Ser Glu Ser Asp Leu Asn
        610                 615                 620

Thr Pro Thr Thr Ser Ser Ile Glu Thr Ser Ser Tyr Ser Ser Ala Ala
625                 630                 635                 640

Thr Glu Ser Ser Val Val Ser Glu Ser Ser Ala Val Asp Ser Leu
                645                 650                 655

Thr Ser Ser Ser Leu Ser Ser Lys Ser Glu Ser Ser Asp Val Val Ser
                660                 665                 670

Ser Thr Thr Asn Ile Glu Ser Ser Thr Ala Ile Glu Thr Thr Met
        675                 680                 685

Asn Ser Glu Ser Ser Thr Asp Ala Gly Ser Ser Ile Ser Gln Ser
        690                 695                 700

Glu Ser Ser Ser Thr Ala Ile Thr Ser Ser Ser Glu Thr Ser Ser Ser
705                 710                 715                 720

Glu Ser Met Ser Ala Ser Ser Thr Thr Ala Ser Asn Thr Ser Ile Glu
                725                 730                 735

Thr Asp Ser Gly Ile Val Ser Gln Ser Glu Ser Ser Asn Ala Leu
                740                 745                 750

<210> SEQ ID NO 27
<211> LENGTH: 623
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (307)..(308)
<223> OTHER INFORMATION: Residues at these positions may or may not be
      separated by an undisclosed linker peptide

<400> SEQUENCE: 27

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140
```

```
Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
            165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
        210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
290                 295                 300

Ser Asn Gly Gln Asn Gln Lys Ala Ala Gly Asn Ile Ala Phe Gly Thr
305                 310                 315                 320

Ala Tyr Gln Thr Ile Thr Asn Asn Gly Gln Ile Cys Leu Arg His Gln
                325                 330                 335

Asp Phe Val Pro Ala Thr Lys Ile Lys Gly Thr Gly Cys Val Thr Ala
            340                 345                 350

Asp Glu Asp Thr Trp Ile Lys Leu Gly Asn Thr Ile Leu Ser Val Glu
        355                 360                 365

Pro Thr His Asn Phe Tyr Leu Lys Asp Ser Lys Ser Ser Leu Ile Val
    370                 375                 380

His Ala Val Ser Ser Asn Gln Thr Phe Thr Val His Gly Phe Gly Asn
385                 390                 395                 400

Gly Asn Lys Leu Gly Leu Thr Leu Pro Leu Thr Gly Asn Arg Asp His
                405                 410                 415

Phe Arg Phe Glu Tyr Tyr Pro Asp Thr Gly Ile Leu Gln Leu Arg Ala
            420                 425                 430

Asp Ala Leu Pro Gln Tyr Phe Lys Ile Gly Lys Gly Tyr Asp Ser Lys
        435                 440                 445

Leu Phe Arg Ile Val Asn Ser Arg Gly Leu Lys Asn Ala Val Thr Tyr
    450                 455                 460

Asp Gly Pro Val Pro Asn Asn Glu Ile Pro Ala Val Cys Leu Ile Pro
465                 470                 475                 480

Cys Thr Asn Gly Pro Ser Ala Pro Glu Ser Glu Ser Asp Leu Asn Thr
                485                 490                 495

Pro Thr Thr Ser Ser Ile Glu Thr Ser Ser Tyr Ser Ser Ala Ala Thr
            500                 505                 510

Glu Ser Ser Val Val Ser Glu Ser Ser Ala Val Asp Ser Leu Thr
        515                 520                 525

Ser Ser Ser Leu Ser Ser Lys Ser Glu Ser Asp Val Val Ser Ser
        530                 535                 540

Thr Thr Asn Ile Glu Ser Ser Thr Ala Ile Glu Thr Thr Met Asn
545                 550                 555                 560

Ser Glu Ser Ser Thr Asp Ala Gly Ser Ser Ser Ile Ser Gln Ser Glu
```

Ser Ser Ser Thr Ala Ile Thr Ser Ser Glu Thr Ser Ser Ser Glu
            565                 570                 575

Ser Met Ser Ala Ser Ser Thr Thr Ala Ser Asn Thr Ser Ile Glu Thr
        580                 585                 590

Asp Ser Gly Ile Val Ser Gln Ser Glu Ser Ser Asn Ala Leu
    595                 600                 605

610                 615                 620

<210> SEQ ID NO 28
<211> LENGTH: 623
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 28

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

```
Ser Asn Gly Gln Asn Gln Lys Ala Ala Gly Asn Ile Ala Phe Gly Thr
305                 310                 315                 320

Ala Tyr Gln Thr Ile Thr Asn Asn Gly Gln Ile Cys Leu Arg His Gln
            325                 330                 335

Asp Phe Val Pro Ala Thr Lys Ile Lys Gly Thr Gly Cys Val Thr Ala
        340                 345                 350

Asp Glu Asp Thr Trp Ile Lys Leu Gly Asn Thr Ile Leu Ser Val Glu
    355                 360                 365

Pro Thr His Asn Phe Tyr Leu Lys Asp Ser Lys Ser Ser Leu Ile Val
370                 375                 380

His Ala Val Ser Ser Asn Gln Thr Phe Thr Val His Gly Phe Gly Asn
385                 390                 395                 400

Gly Asn Lys Leu Gly Leu Thr Leu Pro Leu Thr Gly Asn Arg Asp His
            405                 410                 415

Phe Arg Phe Glu Tyr Tyr Pro Asp Thr Gly Ile Leu Gln Leu Arg Ala
        420                 425                 430

Asp Ala Leu Pro Gln Tyr Phe Lys Ile Gly Lys Gly Tyr Asp Ser Lys
    435                 440                 445

Leu Phe Arg Ile Val Asn Ser Arg Gly Leu Lys Asn Ala Val Thr Tyr
450                 455                 460

Asp Gly Pro Val Pro Asn Asn Glu Ile Pro Ala Val Cys Leu Ile Pro
465                 470                 475                 480

Cys Thr Asn Gly Pro Ser Ala Pro Glu Ser Glu Ser Asp Leu Asn Thr
            485                 490                 495

Pro Thr Thr Ser Ser Ile Glu Thr Ser Ser Tyr Ser Ser Ala Ala Thr
        500                 505                 510

Glu Ser Ser Val Val Ser Glu Ser Ser Ala Val Asp Ser Leu Thr
    515                 520                 525

Ser Ser Ser Leu Ser Ser Lys Ser Glu Ser Ser Asp Val Val Ser Ser
530                 535                 540

Thr Thr Asn Ile Glu Ser Ser Thr Ala Ile Glu Thr Thr Met Asn
545                 550                 555                 560

Ser Glu Ser Ser Thr Asp Ala Gly Ser Ser Ile Ser Gln Ser Glu
            565                 570                 575

Ser Ser Ser Thr Ala Ile Thr Ser Ser Glu Thr Ser Ser Ser Glu
        580                 585                 590

Ser Met Ser Ala Ser Ser Thr Thr Ala Ser Asn Thr Ser Ile Glu Thr
    595                 600                 605

Asp Ser Gly Ile Val Ser Gln Ser Glu Ser Ser Asn Ala Leu
610                 615                 620

<210> SEQ ID NO 29
<211> LENGTH: 860
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(129)
<223> OTHER INFORMATION: This region may or may not be present in its
      entirety
<220> FEATURE:
<221> NAME/KEY: misc_feature
<222> LOCATION: (130)..(326)
<223> OTHER INFORMATION: This region may or may not be present in its
      entirety
<220> FEATURE:
```

```
<221> NAME/KEY: misc_feature
<222> LOCATION: (327)..(445)
<223> OTHER INFORMATION: This region may or may not be present in its
      entirety
<220> FEATURE:
<221> NAME/KEY: misc_feature
<222> LOCATION: (445)..(446)
<223> OTHER INFORMATION: Residues at these positions may or may not be
      separated by an undisclosed linker peptide
<220> FEATURE:
<221> NAME/KEY: misc_feature
<222> LOCATION: (446)..(752)
<223> OTHER INFORMATION: This region may or may not be present in its
      entirety
<220> FEATURE:
<221> NAME/KEY: misc_feature
<222> LOCATION: (753)..(860)
<223> OTHER INFORMATION: This region may or may not be present in its
      entirety

<400> SEQUENCE: 29

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
            20                  25                  30

Ser Phe Phe Gly Gly Leu Glu Val Glu Lys Gly Ala Ser Leu Phe Ile
        35                  40                  45

Lys Ser Asp Asn Gly Pro Val Leu Ala Leu Asn Val Ala Leu Ser Thr
50                  55                  60

Leu Val Arg Pro Val Ile Asn Asn Gly Val Ile Ser Leu Asn Ser Lys
65                  70                  75                  80

Ser Ser Thr Ser Phe Ser Asn Phe Asp Ile Gly Gly Ser Phe Thr
                85                  90                  95

Asn Asn Gly Glu Ile Tyr Leu Asp Ser Ser Gly Leu Val Lys Ser Thr
            100                 105                 110

Ala Tyr Leu Tyr Ala Arg Glu Trp Thr Asn Asn Gly Leu Ile Val Ala
        115                 120                 125

Tyr Gln Asn Gln Lys Ala Ala Gly Asn Ile Ala Phe Gly Thr Ala Tyr
130                 135                 140

Gln Thr Ile Thr Asn Asn Gly Gln Ile Cys Leu Arg His Gln Asp Phe
145                 150                 155                 160

Val Pro Ala Thr Lys Ile Lys Gly Thr Gly Cys Val Thr Ala Asp Glu
                165                 170                 175

Asp Thr Trp Ile Lys Leu Gly Asn Thr Ile Leu Ser Val Glu Pro Thr
            180                 185                 190

His Asn Phe Tyr Leu Lys Asp Ser Lys Ser Ser Leu Ile Val His Ala
        195                 200                 205

Val Ser Ser Asn Gln Thr Phe Thr Val His Gly Phe Gly Asn Gly Asn
210                 215                 220

Lys Leu Gly Leu Thr Leu Pro Leu Thr Gly Asn Arg Asp His Phe Arg
225                 230                 235                 240

Phe Glu Tyr Tyr Pro Asp Thr Gly Ile Leu Gln Leu Arg Ala Asp Ala
                245                 250                 255

Leu Pro Gln Tyr Phe Lys Ile Gly Lys Gly Tyr Asp Ser Lys Leu Phe
            260                 265                 270

Arg Ile Val Asn Ser Arg Gly Leu Lys Asn Ala Val Thr Tyr Asp Gly
        275                 280                 285

Pro Val Pro Asn Asn Glu Ile Pro Ala Val Cys Leu Ile Pro Cys Thr
290                 295                 300
```

```
Asn Gly Pro Ser Ala Pro Glu Ser Glu Ser Asp Leu Asn Thr Pro Thr
305                 310                 315                 320

Thr Ser Ser Ile Glu Thr Ser Ser Tyr Ser Ser Ala Ala Thr Glu Ser
                325                 330                 335

Ser Val Val Ser Glu Ser Ser Ser Ala Val Asp Ser Leu Thr Ser Ser
            340                 345                 350

Ser Leu Ser Ser Lys Ser Glu Ser Ser Asp Val Val Ser Ser Thr Thr
            355                 360                 365

Asn Ile Glu Ser Ser Ser Thr Ala Ile Glu Thr Thr Met Asn Ser Glu
        370                 375                 380

Ser Ser Thr Asp Ala Gly Ser Ser Ser Ile Ser Gln Ser Glu Ser Ser
385                 390                 395                 400

Ser Thr Ala Ile Thr Ser Ser Glu Thr Ser Ser Ser Glu Ser Met
                405                 410                 415

Ser Ala Ser Ser Thr Thr Ala Ser Asn Thr Ser Ile Glu Thr Asp Ser
            420                 425                 430

Gly Ile Val Ser Gln Ser Glu Ser Ser Ser Asn Ala Leu Lys Thr Ile
            435                 440                 445

Thr Gly Val Phe Asn Ser Phe Asn Ser Leu Thr Trp Ser Asn Ala Ala
    450                 455                 460

Thr Tyr Asn Tyr Lys Gly Pro Gly Thr Pro Thr Trp Asn Ala Val Leu
465                 470                 475                 480

Gly Trp Ser Leu Asp Gly Thr Ser Ala Ser Pro Gly Asp Thr Phe Thr
                485                 490                 495

Leu Asn Met Pro Cys Val Phe Lys Phe Thr Thr Ser Gln Thr Ser Val
            500                 505                 510

Asp Leu Thr Ala His Gly Val Lys Tyr Ala Thr Cys Gln Phe Gln Ala
            515                 520                 525

Gly Glu Glu Phe Met Thr Phe Ser Thr Leu Thr Cys Thr Val Ser Asn
            530                 535                 540

Thr Leu Thr Pro Ser Ile Lys Ala Leu Gly Thr Val Thr Leu Pro Leu
545                 550                 555                 560

Ala Phe Asn Val Gly Gly Thr Gly Ser Ser Val Asp Leu Glu Asp Ser
                565                 570                 575

Lys Cys Phe Thr Ala Gly Thr Asn Thr Val Thr Phe Asn Asp Gly Gly
                580                 585                 590

Lys Lys Ile Ser Ile Asn Val Asp Phe Glu Arg Ser Asn Val Asp Pro
            595                 600                 605

Lys Gly Tyr Leu Thr Asp Ser Arg Val Ile Pro Ser Leu Asn Lys Val
            610                 615                 620

Ser Thr Leu Phe Val Ala Pro Gln Cys Ala Asn Gly Tyr Thr Ser Gly
625                 630                 635                 640

Thr Met Gly Phe Ala Asn Thr Tyr Gly Asp Val Gln Ile Asp Cys Ser
                645                 650                 655

Asn Ile His Val Gly Ile Thr Lys Gly Leu Asn Asp Trp Asn Tyr Pro
                660                 665                 670

Val Ser Ser Glu Ser Phe Ser Tyr Thr Lys Thr Cys Ser Ser Asn Gly
            675                 680                 685

Ile Phe Ile Thr Tyr Lys Asn Val Pro Ala Gly Tyr Arg Pro Phe Val
            690                 695                 700

Asp Ala Tyr Ile Ser Ala Thr Asp Val Asn Ser Tyr Thr Leu Ser Tyr
705                 710                 715                 720

Ala Asn Glu Tyr Thr Cys Ala Gly Gly Tyr Trp Gln Arg Ala Pro Phe
```

```
                    725                 730                 735

Thr Leu Arg Trp Thr Gly Tyr Arg Asn Ser Asp Ala Gly Ser Asn Gly
                740                 745                 750

Ile Val Ile Val Ala Thr Thr Arg Thr Val Thr Asp Ser Thr Thr Ala
                755                 760                 765

Val Thr Thr Leu Pro Phe Asp Pro Asn Arg Asp Lys Thr Lys Thr Ile
770                 775                 780

Glu Ile Leu Lys Pro Ile Pro Thr Thr Ile Thr Thr Ser Tyr Val
785                 790                 795                 800

Gly Val Thr Thr Ser Tyr Ser Thr Lys Thr Ala Pro Ile Gly Glu Thr
                805                 810                 815

Ala Thr Val Ile Val Asp Ile Pro Tyr His Thr Thr Thr Val Thr
                820                 825                 830

Ser Lys Trp Thr Gly Thr Ile Thr Ser Thr Thr Thr His Thr Asn Pro
                835                 840                 845

Thr Asp Ser Ile Asp Thr Val Ile Val Gln Val Pro
850                 855                 860

<210> SEQ ID NO 30
<211> LENGTH: 860
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr Ser Arg Ile Asp Arg Gly Gly Ile Gln Gly Phe His Gly Asp Val
1               5                   10                  15

Lys Val His Ser Gly Ala Thr Trp Ala Ile Leu Gly Thr Thr Leu Cys
                20                  25                  30

Ser Phe Phe Gly Gly Leu Glu Val Glu Lys Gly Ala Ser Leu Phe Ile
            35                  40                  45

Lys Ser Asp Asn Gly Pro Val Leu Ala Leu Asn Val Ala Leu Ser Thr
    50                  55                  60

Leu Val Arg Pro Val Ile Asn Asn Gly Val Ile Ser Leu Asn Ser Lys
65                  70                  75                  80

Ser Ser Thr Ser Phe Ser Asn Phe Asp Ile Gly Gly Ser Ser Phe Thr
                85                  90                  95

Asn Asn Gly Glu Ile Tyr Leu Asp Ser Ser Gly Leu Val Lys Ser Thr
            100                 105                 110

Ala Tyr Leu Tyr Ala Arg Glu Trp Thr Asn Asn Gly Leu Ile Val Ala
        115                 120                 125

Tyr Gln Asn Gln Lys Ala Ala Gly Asn Ile Ala Phe Gly Thr Ala Tyr
    130                 135                 140

Gln Thr Ile Thr Asn Asn Gly Gln Ile Cys Leu Arg His Gln Asp Phe
145                 150                 155                 160

Val Pro Ala Thr Lys Ile Lys Gly Thr Gly Cys Val Thr Ala Asp Glu
                165                 170                 175

Asp Thr Trp Ile Lys Leu Gly Asn Thr Ile Leu Ser Val Glu Pro Thr
            180                 185                 190

His Asn Phe Tyr Leu Lys Asp Ser Lys Ser Ser Leu Ile Val His Ala
        195                 200                 205

Val Ser Ser Asn Gln Thr Phe Thr Val His Gly Phe Gly Asn Gly Asn
    210                 215                 220
```

-continued

```
Lys Leu Gly Leu Thr Leu Pro Leu Thr Gly Asn Arg Asp His Phe Arg
225                 230                 235                 240

Phe Glu Tyr Tyr Pro Asp Thr Gly Ile Leu Gln Leu Arg Ala Asp Ala
            245                 250                 255

Leu Pro Gln Tyr Phe Lys Ile Gly Lys Gly Tyr Asp Ser Lys Leu Phe
        260                 265                 270

Arg Ile Val Asn Ser Arg Gly Leu Lys Asn Ala Val Thr Tyr Asp Gly
    275                 280                 285

Pro Val Pro Asn Asn Glu Ile Pro Ala Val Cys Leu Ile Pro Cys Thr
290                 295                 300

Asn Gly Pro Ser Ala Pro Glu Ser Glu Ser Asp Leu Asn Thr Pro Thr
305                 310                 315                 320

Thr Ser Ser Ile Glu Thr Ser Ser Tyr Ser Ser Ala Ala Thr Glu Ser
            325                 330                 335

Ser Val Val Ser Glu Ser Ser Ala Val Asp Ser Leu Thr Ser Ser
        340                 345                 350

Ser Leu Ser Ser Lys Ser Glu Ser Ser Asp Val Val Ser Ser Thr Thr
        355                 360                 365

Asn Ile Glu Ser Ser Ser Thr Ala Ile Glu Thr Thr Met Asn Ser Glu
370                 375                 380

Ser Ser Thr Asp Ala Gly Ser Ser Ser Ile Ser Gln Ser Glu Ser Ser
385                 390                 395                 400

Ser Thr Ala Ile Thr Ser Ser Ser Glu Thr Ser Ser Ser Glu Ser Met
                405                 410                 415

Ser Ala Ser Ser Thr Thr Ala Ser Asn Thr Ser Ile Glu Thr Asp Ser
        420                 425                 430

Gly Ile Val Ser Gln Ser Glu Ser Ser Ser Asn Ala Leu Lys Thr Ile
        435                 440                 445

Thr Gly Val Phe Asn Ser Phe Asn Ser Leu Thr Trp Ser Asn Ala Ala
450                 455                 460

Thr Tyr Asn Tyr Lys Gly Pro Gly Thr Pro Thr Trp Asn Ala Val Leu
465                 470                 475                 480

Gly Trp Ser Leu Asp Gly Thr Ser Ala Ser Pro Gly Asp Thr Phe Thr
            485                 490                 495

Leu Asn Met Pro Cys Val Phe Lys Phe Thr Thr Ser Gln Thr Ser Val
            500                 505                 510

Asp Leu Thr Ala His Gly Val Lys Tyr Ala Thr Cys Gln Phe Gln Ala
        515                 520                 525

Gly Glu Glu Phe Met Thr Phe Ser Thr Leu Thr Cys Thr Val Ser Asn
530                 535                 540

Thr Leu Thr Pro Ser Ile Lys Ala Leu Gly Thr Val Thr Leu Pro Leu
545                 550                 555                 560

Ala Phe Asn Val Gly Gly Thr Gly Ser Ser Val Asp Leu Glu Asp Ser
                565                 570                 575

Lys Cys Phe Thr Ala Gly Thr Asn Thr Val Thr Phe Asn Asp Gly Gly
            580                 585                 590

Lys Lys Ile Ser Ile Asn Val Asp Phe Glu Arg Ser Asn Val Asp Pro
        595                 600                 605

Lys Gly Tyr Leu Thr Asp Ser Arg Val Ile Pro Ser Leu Asn Lys Val
            610                 615                 620

Ser Thr Leu Phe Val Ala Pro Gln Cys Ala Asn Gly Tyr Thr Ser Gly
625                 630                 635                 640

Thr Met Gly Phe Ala Asn Thr Tyr Gly Asp Val Gln Ile Asp Cys Ser
```

```
                   645                 650                 655

Asn Ile His Val Gly Ile Thr Lys Gly Leu Asn Asp Trp Asn Tyr Pro
            660                 665                 670

Val Ser Ser Glu Ser Phe Ser Tyr Thr Lys Thr Cys Ser Ser Asn Gly
        675                 680                 685

Ile Phe Ile Thr Tyr Lys Asn Val Pro Ala Gly Tyr Arg Pro Phe Val
690                 695                 700

Asp Ala Tyr Ile Ser Ala Thr Asp Val Asn Ser Tyr Thr Leu Ser Tyr
705                 710                 715                 720

Ala Asn Glu Tyr Thr Cys Ala Gly Gly Tyr Trp Gln Arg Ala Pro Phe
            725                 730                 735

Thr Leu Arg Trp Thr Gly Tyr Arg Asn Ser Asp Ala Gly Ser Asn Gly
        740                 745                 750

Ile Val Ile Val Ala Thr Thr Arg Thr Val Thr Asp Ser Thr Thr Ala
    755                 760                 765

Val Thr Thr Leu Pro Phe Asp Pro Asn Arg Asp Lys Thr Lys Thr Ile
770                 775                 780

Glu Ile Leu Lys Pro Ile Pro Thr Thr Thr Ile Thr Thr Ser Tyr Val
785                 790                 795                 800

Gly Val Thr Thr Ser Tyr Ser Thr Lys Thr Ala Pro Ile Gly Glu Thr
            805                 810                 815

Ala Thr Val Ile Val Asp Ile Pro Tyr His Thr Thr Thr Thr Val Thr
        820                 825                 830

Ser Lys Trp Thr Gly Thr Ile Thr Ser Thr Thr Thr His Thr Asn Pro
    835                 840                 845

Thr Asp Ser Ile Asp Thr Val Ile Val Gln Val Pro
850                 855                 860

<210> SEQ ID NO 31
<211> LENGTH: 860
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(307)
<223> OTHER INFORMATION: This region may or may not be present in its
      entirety
<220> FEATURE:
<221> NAME/KEY: misc_feature
<222> LOCATION: (308)..(415)
<223> OTHER INFORMATION: This region may or may not be present in its
      entirety
<220> FEATURE:
<221> NAME/KEY: misc_feature
<222> LOCATION: (415)..(416)
<223> OTHER INFORMATION: Residues at these positions may or may not be
      separated by an undisclosed linker peptide
<220> FEATURE:
<221> NAME/KEY: misc_feature
<222> LOCATION: (416)..(544)
<223> OTHER INFORMATION: This region may or may not be present in its
      entirety
<220> FEATURE:
<221> NAME/KEY: misc_feature
<222> LOCATION: (545)..(741)
<223> OTHER INFORMATION: This region may or may not be present in it
      s entirety
<220> FEATURE:
<221> NAME/KEY: misc_feature
<222> LOCATION: (742)..(860)
<223> OTHER INFORMATION: This region may or may not be present in its
      entirety
```

<400> SEQUENCE: 31

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
290                 295                 300

Ser Asn Gly Ile Val Ile Val Ala Thr Thr Arg Thr Val Thr Asp Ser
305                 310                 315                 320

Thr Thr Ala Val Thr Thr Leu Pro Phe Asp Pro Asn Arg Asp Lys Thr
                325                 330                 335

Lys Thr Ile Glu Ile Leu Lys Pro Ile Pro Thr Thr Thr Ile Thr Thr
            340                 345                 350

Ser Tyr Val Gly Val Thr Thr Ser Tyr Ser Thr Lys Thr Ala Pro Ile
        355                 360                 365

Gly Glu Thr Ala Thr Val Ile Val Asp Ile Pro Tyr His Thr Thr Thr
    370                 375                 380

Thr Val Thr Ser Lys Trp Thr Gly Thr Ile Ser Thr Thr Thr His
385                 390                 395                 400

Thr Asn Pro Thr Asp Ser Ile Asp Thr Val Ile Val Gln Val Pro Thr

-continued

```
                    405                 410                 415
Ser Arg Ile Asp Arg Gly Gly Ile Gln Gly Phe His Gly Asp Val Lys
                420                 425                 430

Val His Ser Gly Ala Thr Trp Ala Ile Leu Gly Thr Thr Leu Cys Ser
                435                 440                 445

Phe Phe Gly Gly Leu Glu Val Glu Lys Gly Ala Ser Leu Phe Ile Lys
                450                 455                 460

Ser Asp Asn Gly Pro Val Leu Ala Leu Asn Val Ala Leu Ser Thr Leu
465                 470                 475                 480

Val Arg Pro Val Ile Asn Asn Gly Val Ile Ser Leu Asn Ser Lys Ser
                485                 490                 495

Ser Thr Ser Phe Ser Asn Phe Asp Ile Gly Gly Ser Ser Phe Thr Asn
                500                 505                 510

Asn Gly Glu Ile Tyr Leu Asp Ser Ser Gly Leu Val Lys Ser Thr Ala
                515                 520                 525

Tyr Leu Tyr Ala Arg Glu Trp Thr Asn Asn Gly Leu Ile Val Ala Tyr
                530                 535                 540

Gln Asn Gln Lys Ala Ala Gly Asn Ile Ala Phe Gly Thr Ala Tyr Gln
545                 550                 555                 560

Thr Ile Thr Asn Asn Gly Gln Ile Cys Leu Arg His Gln Asp Phe Val
                565                 570                 575

Pro Ala Thr Lys Ile Lys Gly Thr Gly Cys Val Thr Ala Asp Glu Asp
                580                 585                 590

Thr Trp Ile Lys Leu Gly Asn Thr Ile Leu Ser Val Glu Pro Thr His
                595                 600                 605

Asn Phe Tyr Leu Lys Asp Ser Lys Ser Ser Leu Ile Val His Ala Val
                610                 615                 620

Ser Ser Asn Gln Thr Phe Thr Val His Gly Phe Gly Asn Gly Asn Lys
625                 630                 635                 640

Leu Gly Leu Thr Leu Pro Leu Thr Gly Asn Arg Asp His Phe Arg Phe
                645                 650                 655

Glu Tyr Tyr Pro Asp Thr Gly Ile Leu Gln Leu Arg Ala Asp Ala Leu
                660                 665                 670

Pro Gln Tyr Phe Lys Ile Gly Lys Gly Tyr Asp Ser Lys Leu Phe Arg
                675                 680                 685

Ile Val Asn Ser Arg Gly Leu Lys Asn Ala Val Thr Tyr Asp Gly Pro
                690                 695                 700

Val Pro Asn Asn Glu Ile Pro Ala Val Cys Leu Ile Pro Cys Thr Asn
705                 710                 715                 720

Gly Pro Ser Ala Pro Glu Ser Glu Ser Asp Leu Asn Thr Pro Thr Thr
                725                 730                 735

Ser Ser Ile Glu Thr Ser Ser Tyr Ser Ser Ala Ala Thr Glu Ser Ser
                740                 745                 750

Val Val Ser Glu Ser Ser Ala Val Asp Ser Leu Thr Ser Ser Ser
                755                 760                 765

Leu Ser Ser Lys Ser Glu Ser Asp Val Val Ser Ser Thr Thr Asn
                770                 775                 780

Ile Glu Ser Ser Ser Thr Ala Ile Glu Thr Thr Met Asn Ser Glu Ser
785                 790                 795                 800

Ser Thr Asp Ala Gly Ser Ser Ile Ser Gln Ser Glu Ser Ser Ser
                805                 810                 815

Thr Ala Ile Thr Ser Ser Ser Glu Thr Ser Ser Ser Glu Ser Met Ser
                820                 825                 830
```

-continued

Ala Ser Ser Thr Thr Ala Ser Asn Thr Ser Ile Glu Thr Asp Ser Gly
        835                 840                 845

Ile Val Ser Gln Ser Glu Ser Ser Asn Ala Leu
    850                 855                 860

<210> SEQ ID NO 32
<211> LENGTH: 860
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
        35                  40                  45

Thr Phe Thr Leu Asn Met Pro Cys Val Phe Lys Phe Thr Thr Ser Gln
    50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

Ser Asn Gly Ile Val Ile Val Ala Thr Thr Arg Thr Val Thr Asp Ser
305                 310                 315                 320

Thr Thr Ala Val Thr Thr Leu Pro Phe Asp Pro Asn Arg Asp Lys Thr

-continued

```
                325                 330                 335
Lys Thr Ile Glu Ile Leu Lys Pro Ile Pro Thr Thr Thr Ile Thr Thr
                340                 345                 350
Ser Tyr Val Gly Val Thr Thr Ser Tyr Ser Thr Lys Thr Ala Pro Ile
                355                 360                 365
Gly Glu Thr Ala Thr Val Ile Val Asp Ile Pro Tyr His Thr Thr Thr
                370                 375                 380
Thr Val Thr Ser Lys Trp Thr Gly Thr Ile Thr Ser Thr Thr Thr His
385                 390                 395                 400
Thr Asn Pro Thr Asp Ser Ile Asp Thr Val Ile Val Gln Val Pro Thr
                405                 410                 415
Ser Arg Ile Asp Arg Gly Gly Ile Gln Gly Phe His Gly Asp Val Lys
                420                 425                 430
Val His Ser Gly Ala Thr Trp Ala Ile Leu Gly Thr Thr Leu Cys Ser
                435                 440                 445
Phe Phe Gly Gly Leu Glu Val Glu Lys Gly Ala Ser Leu Phe Ile Lys
                450                 455                 460
Ser Asp Asn Gly Pro Val Leu Ala Leu Asn Val Ala Leu Ser Thr Leu
465                 470                 475                 480
Val Arg Pro Val Ile Asn Asn Gly Val Ile Ser Leu Asn Ser Lys Ser
                485                 490                 495
Ser Thr Ser Phe Ser Asn Phe Asp Ile Gly Gly Ser Ser Phe Thr Asn
                500                 505                 510
Asn Gly Glu Ile Tyr Leu Asp Ser Ser Gly Leu Val Lys Ser Thr Ala
                515                 520                 525
Tyr Leu Tyr Ala Arg Glu Trp Thr Asn Asn Gly Leu Ile Val Ala Tyr
                530                 535                 540
Gln Asn Gln Lys Ala Ala Gly Asn Ile Ala Phe Gly Thr Ala Tyr Gln
545                 550                 555                 560
Thr Ile Thr Asn Asn Gly Gln Ile Cys Leu Arg His Gln Asp Phe Val
                565                 570                 575
Pro Ala Thr Lys Ile Lys Gly Thr Gly Cys Val Thr Ala Asp Glu Asp
                580                 585                 590
Thr Trp Ile Lys Leu Gly Asn Thr Ile Leu Ser Val Glu Pro Thr His
                595                 600                 605
Asn Phe Tyr Leu Lys Asp Ser Lys Ser Ser Leu Ile Val His Ala Val
                610                 615                 620
Ser Ser Asn Gln Thr Phe Thr Val His Gly Phe Gly Asn Gly Asn Lys
625                 630                 635                 640
Leu Gly Leu Thr Leu Pro Leu Thr Gly Asn Arg Asp His Phe Arg Phe
                645                 650                 655
Glu Tyr Tyr Pro Asp Thr Gly Ile Leu Gln Leu Arg Ala Asp Ala Leu
                660                 665                 670
Pro Gln Tyr Phe Lys Ile Gly Lys Gly Tyr Asp Ser Lys Leu Phe Arg
                675                 680                 685
Ile Val Asn Ser Arg Gly Leu Lys Asn Ala Val Thr Tyr Asp Gly Pro
                690                 695                 700
Val Pro Asn Asn Glu Ile Pro Ala Val Cys Leu Ile Pro Cys Thr Asn
705                 710                 715                 720
Gly Pro Ser Ala Pro Glu Ser Glu Ser Asp Leu Asn Thr Pro Thr Thr
                725                 730                 735
Ser Ser Ile Glu Thr Ser Ser Tyr Ser Ser Ala Ala Thr Glu Ser Ser
                740                 745                 750
```

```
Val Val Ser Glu Ser Ser Ala Val Asp Ser Leu Thr Ser Ser Ser
        755                 760                 765

Leu Ser Ser Lys Ser Glu Ser Ser Asp Val Val Ser Ser Thr Thr Asn
    770                 775                 780

Ile Glu Ser Ser Ser Thr Ala Ile Glu Thr Thr Met Asn Ser Glu Ser
785                 790                 795                 800

Ser Thr Asp Ala Gly Ser Ser Ser Ile Ser Gln Ser Glu Ser Ser Ser
                805                 810                 815

Thr Ala Ile Thr Ser Ser Ser Glu Thr Ser Ser Ser Glu Ser Met Ser
            820                 825                 830

Ala Ser Ser Thr Thr Ala Ser Asn Thr Ser Ile Glu Thr Asp Ser Gly
        835                 840                 845

Ile Val Ser Gln Ser Glu Ser Ser Ser Asn Ala Leu
        850                 855                 860

<210> SEQ ID NO 33
<211> LENGTH: 316
<212> TYPE: PRT
<213> ORGANISM: Candida albicans

<400> SEQUENCE: 33

Gln Asn Gln Lys Ala Ala Gly Asn Ile Ala Phe Gly Thr Ala Tyr Gln
1               5                   10                  15

Thr Ile Thr Asn Asn Gly Gln Ile Cys Leu Arg His Gln Asp Phe Val
            20                  25                  30

Pro Ala Thr Lys Ile Lys Gly Thr Gly Cys Val Thr Ala Asp Glu Asp
        35                  40                  45

Thr Trp Ile Lys Leu Gly Asn Thr Ile Leu Ser Val Glu Pro Thr His
    50                  55                  60

Asn Phe Tyr Leu Lys Asp Ser Lys Ser Ser Leu Ile Val His Ala Val
65                  70                  75                  80

Ser Ser Asn Gln Thr Phe Thr Val His Gly Phe Gly Asn Gly Asn Lys
                85                  90                  95

Leu Gly Leu Thr Leu Pro Leu Thr Gly Asn Arg Asp His Phe Arg Phe
            100                 105                 110

Glu Tyr Tyr Pro Asp Thr Gly Ile Leu Gln Leu Arg Ala Asp Ala Leu
        115                 120                 125

Pro Gln Tyr Phe Lys Ile Gly Lys Gly Tyr Asp Ser Lys Leu Phe Arg
    130                 135                 140

Ile Val Asn Ser Arg Gly Leu Lys Asn Ala Val Thr Tyr Asp Gly Pro
145                 150                 155                 160

Val Pro Asn Asn Glu Ile Pro Ala Val Cys Leu Ile Pro Cys Thr Asn
                165                 170                 175

Gly Pro Ser Ala Pro Glu Ser Glu Ser Asp Leu Asn Thr Pro Thr Thr
            180                 185                 190

Ser Ser Ile Glu Thr Ser Ser Tyr Ser Ser Ala Ala Thr Glu Ser Ser
        195                 200                 205

Val Val Ser Glu Ser Ser Ala Val Asp Ser Leu Thr Ser Ser Ser
    210                 215                 220

Leu Ser Ser Lys Ser Glu Ser Ser Asp Val Val Ser Ser Thr Thr Asn
225                 230                 235                 240

Ile Glu Ser Ser Ser Thr Ala Ile Glu Thr Thr Met Asn Ser Glu Ser
                245                 250                 255

Ser Thr Asp Ala Gly Ser Ser Ser Ile Ser Gln Ser Glu Ser Ser Ser
```

```
                260                 265                 270
Thr Ala Ile Thr Ser Ser Ser Glu Thr Ser Ser Ser Glu Ser Met Ser
            275                 280                 285

Ala Ser Ser Thr Thr Ala Ser Asn Thr Ser Ile Glu Thr Asp Ser Gly
            290                 295                 300

Ile Val Ser Gln Ser Glu Ser Ser Ser Asn Ala Leu
305                 310                 315

<210> SEQ ID NO 34
<211> LENGTH: 415
<212> TYPE: PRT
<213> ORGANISM: Candida albicans

<400> SEQUENCE: 34

Lys Thr Ile Thr Gly Val Phe Asn Ser Phe Asn Ser Leu Thr Trp Ser
1               5                   10                  15

Asn Ala Ala Thr Tyr Asn Tyr Lys Gly Pro Gly Thr Pro Thr Trp Asn
            20                  25                  30

Ala Val Leu Gly Trp Ser Leu Asp Gly Thr Ser Ala Ser Pro Gly Asp
            35                  40                  45

Thr Phe Thr Leu Asn Met Pro Cys Val Phe Lys Phe Thr Thr Ser Gln
        50                  55                  60

Thr Ser Val Asp Leu Thr Ala His Gly Val Lys Tyr Ala Thr Cys Gln
65                  70                  75                  80

Phe Gln Ala Gly Glu Glu Phe Met Thr Phe Ser Thr Leu Thr Cys Thr
                85                  90                  95

Val Ser Asn Thr Leu Thr Pro Ser Ile Lys Ala Leu Gly Thr Val Thr
            100                 105                 110

Leu Pro Leu Ala Phe Asn Val Gly Gly Thr Gly Ser Ser Val Asp Leu
        115                 120                 125

Glu Asp Ser Lys Cys Phe Thr Ala Gly Thr Asn Thr Val Thr Phe Asn
    130                 135                 140

Asp Gly Gly Lys Lys Ile Ser Ile Asn Val Asp Phe Glu Arg Ser Asn
145                 150                 155                 160

Val Asp Pro Lys Gly Tyr Leu Thr Asp Ser Arg Val Ile Pro Ser Leu
                165                 170                 175

Asn Lys Val Ser Thr Leu Phe Val Ala Pro Gln Cys Ala Asn Gly Tyr
            180                 185                 190

Thr Ser Gly Thr Met Gly Phe Ala Asn Thr Tyr Gly Asp Val Gln Ile
        195                 200                 205

Asp Cys Ser Asn Ile His Val Gly Ile Thr Lys Gly Leu Asn Asp Trp
    210                 215                 220

Asn Tyr Pro Val Ser Ser Glu Ser Phe Ser Tyr Thr Lys Thr Cys Ser
225                 230                 235                 240

Ser Asn Gly Ile Phe Ile Thr Tyr Lys Asn Val Pro Ala Gly Tyr Arg
                245                 250                 255

Pro Phe Val Asp Ala Tyr Ile Ser Ala Thr Asp Val Asn Ser Tyr Thr
            260                 265                 270

Leu Ser Tyr Ala Asn Glu Tyr Thr Cys Ala Gly Gly Tyr Trp Gln Arg
        275                 280                 285

Ala Pro Phe Thr Leu Arg Trp Thr Gly Tyr Arg Asn Ser Asp Ala Gly
    290                 295                 300

Ser Asn Gly Ile Val Ile Val Ala Thr Thr Arg Thr Val Thr Asp Ser
305                 310                 315                 320
```

-continued

```
Thr Thr Ala Val Thr Thr Leu Pro Phe Asp Pro Asn Arg Asp Lys Thr
            325             330             335

Lys Thr Ile Glu Ile Leu Lys Pro Ile Pro Thr Thr Thr Ile Thr Thr
            340             345             350

Ser Tyr Val Gly Val Thr Thr Ser Tyr Ser Thr Lys Thr Ala Pro Ile
        355             360             365

Gly Glu Thr Ala Thr Val Ile Val Asp Ile Pro Tyr His Thr Thr Thr
        370             375             380

Thr Val Thr Ser Lys Trp Thr Gly Thr Ile Thr Ser Thr Thr Thr His
385             390             395             400

Thr Asn Pro Thr Asp Ser Ile Asp Thr Val Ile Val Gln Val Pro
                405             410             415
```

COMPOSITIONS AND METHODS FOR TREATING FUNGAL AND BACTERIAL PATHOGENS

FIELD OF THE INVENTION

The present invention relates generally to compositions and methods for detecting, treating and preventing infectious diseases in a subject.

BACKGROUND OF THE INVENTION

The fungus *Candida*, the third most common cause of healthcare-associated bloodstream infections, causes approximately 60,000 cases of hematogenously disseminated candidiasis per year in the United States, resulting in billions of dollars of healthcare expenditures. Despite current antifungal therapy, mortality remains unacceptably high. Because of the rising incidence of life-threatening candidiasis and high treatment failure rates, more effective prophylactic and therapeutic strategies are needed.

Lethal infections of antibiotic resistant pathogenic bacteria, like infections resulting from *Candida*, are becoming increasingly frequent. Moreover, the risk of contracting these lethal infections is extremely high for many at-risk patients in intensive care units (ICUs) every year as well as for soldiers deployed to front line combat zones. *Acinetobacter* species are a frequent source of infection in hospitalized patients and soldiers, in particular the species *Acinetobacter baumannii*. *Acinetobacter* is a genus of gram negative bacteria belonging to the Gammaproteobacteria. *Acinetobacter* species contribute to the mineralization of aromatic compounds in the soil. Unfortunately, no technology presently exists that prevents *Acinetobacter* infections, aside from standard hand washing and other infection control practices in hospital settings.

Another bacterium, *Staphylococcus aureus* is the leading cause of skin and skin structure infections including cellulitis and furunculosis, and is among the most common causes of bacteremia. Strains of *S. aureus* that exhibit the methicillin-resistant (MRSA) phenotype are predominant causes of healthcare- and community-acquired infections, including invasive disease in immune competent hosts, in immune suppression (e.g. neutropenia, solid-organ or bone marrow transplants), and in inherited immune dysfunctions manifesting recurring cutaneous infection (e.g. Job's Syndrome, Chronic Granulomatous Disease). The significant impact of MRSA on public health is of special concern in light of high rates of mortality associated with invasive *S. aureus* disease even with appropriate antimicrobial therapy (e.g. 15-40% in bacteremia and endocarditis). Increasing rates of life-threatening infections and decreasing susceptibility to antibiotics call for development of an effective vaccine targeting *S. aureus*.

There accordingly exists a need for compounds and methods that reduce the risk of infectious diseases related to fungal and bacterial infections and provide effective therapies. The present invention satisfies this need and provides related advantages as well.

SUMMARY OF THE INVENTION

Fragments of the *Candida* cell surface proteins Als3 and Hyr1 and combinations thereof useful in immunizing a subject against fungal or bacterial infections or both are described below.

The amino acid sequence of native *C. albicans* SC5314 Als3 polypeptide is as follows:

```
   1 MLQQYTLLLIYLSVATAKTI TGVFNSFNSLTWSNAATYNY KGPGTPTWNAVLGWSLDGTS
  61 ASPGDTFTLNMPCVFKFTTS QTSVDLTAHGVKYATCQFQA GEEFMTFSTLTCTVSNTLTP
 121 SIKALGTVTLPLAFNVGGTG SSVDLEDSKCFTAGTNTVTF NDGGKKISINVDFERSNVDP
 181 KGYLTDSRVIPSLNKVSTLF VAPQCANGYTSGTMGFANTY GDVQIDCSNIHVGITKGLND
 241 WNYPVSSESFSYTKTCSSNG IFITYKNVPAGYRPFVDAYI SATDVNSYTLSYANEYTCAG
 301 GYWQRAPFTLRWTGYRNSDA GSNGIVIVATTRTVTDSTTA VTTLPFDPNRDKTKTIEILK
 361 PIPTTTITTSYVGVTTSYST KTAPIGETATVIVDIPYHTT TTVTSKWTGTITSTTTHTNP
 421 TDSIDTVIVQVPSPNPTVTT TEYWSQSFATTTTITGPPGN TDTVLIREPPNHTVTTTEYW
 481 SESYTTTSTFTAPPGGTDSV IIKEPPNPTVTTTEYWSESY TTTSTFTAPPGGTDSVIIKE
 541 PPNHTVTTTEYWSQSYTTTT TVTAPPGGTDTVLVREPPNH TVTTTEYWSQSYTTTTTVIA
 601 PPGGTDSVIIREPPNPTVTT TEYWSQSYATTTTITAPPGE TDTVLIREPPNHTVTTTEYW
 661 SQSYATTTTITAPPGETDTV LIREPPNHTVTTTEYWSQSF ATTTTVTAPPGGTDTVIIRE
 721 PPNHTVTTTEYWSQSYATTT TITAPPGETDTVLIREPPNH TVTTTEYWSQSYATTTTIIA
 781 PPGETDTVLIREPPNPTVTT TEYWSQSYTTATTVTAPPGG TDTVIIYDTMSSSEISSFSR
 841 PHYTNHTTLWSTTWVIETKT ITETSCEGDKGCSWVSVSTR IVTIPNNIETPMVTNTVDST
 901 TTESTSQSPSGIFSESGVSV ETESSTVTTAQTNPSVPTTE SEVVFTTKGNNENGPYESPS
 961 TNVKSSMDENSEFTTSTAAS TSTDIENETIATTGSVEASS PIISSSADETTTVTTTAEST
1021 SVIEQPTNNNGGGKAPSATS SPSTTTTANNDSVITGTTST NQSQSQSQYNSDTQQTTLSQ
1081 QMTSSLVSLHMLTTFDGSGS VIQHSTWLCGLITLLSLFI
```

Select Als fragments are as follows.
Als3 (18-324)

In one aspect, the invention features and Als3 (18-324 amino acid fragment). In particular, the invention features an isolated polypeptide optionally fused to a heterologous fusion partner, wherein the amino acid sequence of the polypeptide consists of an amino acid sequence having at least 95% identity to

```
                                                      (SEQ ID NO: 2)
                   KTI TGVFNSFNSLTWSNAATYNY KGPGTPTWNAVLGWSLDGTS

ASPGDTFTLNMPCVFKFTTS QTSVDLTAHGVKYATCQFQA GEEFMTFSTLTCTVSNTLTP

SIKALGTVTLPLAFNVGGTG SSVDLEDSKCFTAGTNTVTF NDGGKKISINVDFERSNVDP

KGYLTDSRVIPSLNKVSTLF VAPQCANGYTSGTMGFANTY GDVQIDCSNIHVGITKGLND

WNYPVSSESFSYTKTCSSNG IFITYKNVPAGYRPFVDAYI SATDVNSYTLSYANEYTCAG

GYWQRAPFTLRWTGYRNSDA GSNG.
```

Als3 (Ser/Thr-Rich Sequence)

In another aspect, the invention features an isolated polypeptide optionally fused to a heterologous fusion partner, wherein the amino acid sequence of the polypeptide consists of an amino acid sequence having at least 95% identity to

```
                                                      (SEQ ID NO: 3)
                     IVIVATTRTVTDSTTA VTTLPFDPNRDKTKTIEILK

PIPTTTITTSYVGVTTSYST KTAPIGETATVIVDIPYHTT TTVTSKWTGTITSTTTHTNP

TDSIDTVIVQVP.
```

Hyr1

In other aspect, the invention features fragments of Hyr1. The amino acid sequence of native *C. albicans* SC5314 Hyr1 polypeptide is as follows:

```
  1 MKVVSNFIFTILLTLNLSAA LEVVTSRIDRGGIQGFHGDV KVHSGATWAILGTTLCSFFG

61 GLEVEKGASLFIKSDNGPVL ALNVALSTLVRPVINNGVIS LNSKSSTSFSNFDIGGSSFT

121 NNGEIYLDSSGLVKSTAYLY AREWTNNGLIVAYQNQKAAG NIAFGTAYQTITNNGQICLR

181 HQDFVPATKIKGTGCVTADE DTWIKLGNTILSVEPTHNFY LKDSKSSLIVHAVSSNQTFT

241 VHGFGNGNKLGLTLPLTGNR DHFRFEYYPDTGILQLRADA LPQYFKIGKGYDSKLFRIVN

301 SRGLKNAVTYDGPVPNNEIP AVCLIPCTNGPSAPESESDL NTPTTSSIETSSYSSAATES

361 SVVSESSSAVDSLTSSSLSS KSESSDVVSSTTNIESSSTA IETTMNSESSTDAGSSSISQ

421 SESSSTAITSSSETSSSESM SASSTTASNTSIETDSGIVS QSESSSNALSSTEQSITSSP

481 GQSTIYVNSTVTSTITSCDE NKCTEDVVTIFTTVPCSTDC VPTTGDIPMSTSYTQRTVTS

541 TITNCDEVSCSQDVVTYTTN VPHTTVDATTTTTSTGGDN STGGNESGSNHGPGNGSTEG

601 SGNGSGAGSNEGSQSGPNNG SGSGSEGGSNNGSGSDSGSN NGSGSGSNNGSGSGSTEGSE

661 GGSGSNEGSQSGSGSQPGPN EGSEGGSGSNEGSNHGSNEG SGSGSGSGSNNGSGSGSQSG

721 SGSGSQSGSESGSNSGSNEG SNPGAGNGSNEGSGQGSGNG SEAGSGQGSGPNNGSGSGHN

781 DGSGSGSNQGSNPGAGSGSG SESGSKAGSHSGSNEGAKTD SIEGFHTESKPGFNTGAHTD

841 ATVTGNSVANPVTTSTESDT TISVTVSITSYMTGFDGKPK PFTTVDVIPVPHSMPSNTTD

901 SSSSVPTIDTNENGSSIVTGG KSILFGLIVSMVVLFM
```

Select fragments of Hyr1 are as follows.
Hyr1 (Hydrophobic Sequence)
In particular, the invention features an isolated polypeptide optionally fused to a heterologous fusion partner, wherein the amino acid sequence of the polypeptide consists of an amino acid sequence having at least 95% identity to

```
                                                  (SEQ ID NO: 5)
TSRIDRGGIQGFHGDVKVHS GATWAILGTTLCSFFGGLEV EKGASLFIKSDNGPVLALNV

ALSTLVRPVINNGVISLNSK SSTSFSNFDIGGSSFTNNGE IYLDSSGLVKSTAYLYAREW

TNNGLIVAY.
```

Hyr1 (154-350)
In another aspect, the invention features an isolated polypeptide optionally fused to a heterologous fusion partner, wherein the amino acid sequence of the polypeptide consists of an amino acid sequence having at least 95% identity to

```
                                                  (SEQ ID NO: 6)
                            QNQKAAG NIAFGTAYQTITNNGQICLR

HQDFVPATKIKGTGCVTADE DTWIKLGNTILSVEPTHNFY LKDSKSSLIVHAVSSNQTFT

VHGFGNGNKLGLTLPLTGNR DHFRFEYYPDTGILQLRADA LPQYFKIGKGYDSKLFRIVN

SRGLKNAVTYDGPVPNNEIP AVCLIPCTNGPSAPESESDL NTPTTSSIET.
```

Hyr1 (201-350)
In another aspect, the invention features an isolated polypeptide optionally fused to a heterologous fusion partner, wherein the amino acid sequence of the polypeptide consists of an amino acid sequence having at least 95% identity to

```
                                                  (SEQ ID NO: 7)
                     DTWIKLGNTILSVEPTHNFY LKDSKSSLIVHAVSSNQTFT

VHGFGNGNKLGLTLPLTGNR DHFRFEYYPDTGILQLRADA LPQYFKIGKGYDSKLFRIVN

SRGLKNAVTYDGPVPNNEIP AVOLIPCTNGPSAPESESDL NTPTTSSIET.
```

Hyr1 (25-469)
In another aspect, the invention features an isolated polypeptide optionally fused to a heterologous fusion partner, wherein the amino acid sequence of the polypeptide consists of an amino acid sequence having at least 95% identity to

```
                                                  (SEQ ID NO: 8)
                     TSRIDRGGIQGFHGDV KVHSGATWAILGTTLCSFFG

GLEVEKGASLFIKSDNGPVL ALNVALSTLVRPVINNGVIS LNSKSSTSFSNFDIGGSSFT

NNGEIYLDSSGLVKSTAYLY AREWTNNGLIVAYQNQKAAG NIAFGTAYQTITNNGQICLR

HQDFVPATKIKGTGCVTADE DTWIKLGNTILSVEPTHNFY LKDSKSSLIVHAVSSNQTFT

VHGFGNGNKLGLTLPLTGNR DHFRFEYYPDTGILQLRADA LPQYFKIGKGYDSKLFRIVN

SRGLKNAVTYDGPVPNNEIP AVCLIPCTNGPSAPESESDL NTPTTSSIETSSYSSAATES

SVVSESSSAVDSLTSSSLSS KSESSDVVSSTTNIESSSTA IETTMNSESSTDAGSSSISQ

SESSSTAITSSSETSSSESM SASSTTASNTSIETDSGIVS QSESSSNAL.
```

Hyr1 (201-469)

In another aspect, the invention features an isolated polypeptide optionally fused to a heterologous fusion partner, wherein the amino acid sequence of the polypeptide consists of an amino acid sequence having at least 95% identity to

```
                                              (SEQ ID NO: 9)
                   DTWIKLGNTILSVEPTHNFY LKDSKSSLIVHAVSSNQTFT

VHGFGNGNKLGLTLPLTGNR DHFRFEYYPDTGILQLRADA LPQYFKIGKGYDSKLFRIVN

SRGLKNAVTYDGPVPNNEIP AVQLIPCTNGPSAPESESDL NTPTTSSIETSSYSSAATES

SVVSESSSAVDSLTSSSLSS KSESSDVVSSTTNIESSSTA IETTMNSESSTDAGSSSISQ

SESSSTAITSSSETSSSESM SASSTTASNTSIETDSGIVS QSESSSNAL.
```

Hyr1 (Ser/Thr-Rich Sequence)

In another aspect, the invention features an isolated polypeptide optionally fused to a heterologous fusion partner, wherein the amino acid sequence of the polypeptide consists of an amino acid sequence having at least 95% identity to

```
                                             (SEQ ID NO: 10)
                    SSYSSAATESSVVS ESSSAVDSLTSSSLSSKSES

SDVVSSTTNIESSSTAIETT MNSESSTDAGSSSISQSESS STAITSSSETSSSESMSASS

TTASNTSIETDSGIVSQSES SSNAL.
```

Hyr1 (154-469)

In another aspect, the invention features an isolated polypeptide optionally fused to a heterologous fusion partner, wherein the amino acid sequence of the polypeptide consists of an amino acid sequence having at least 95% identity to

```
                                             (SEQ ID NO: 33)
                         QNQKAAG NIAFGTAYQTITNNGQICLR

HQDFVPATKIKGTGCVTADE DTWIKLGNTILSVEPTHNFY LKDSKSSLIVHAVSSNQTFT

VHGFGNGNKLGLTLPLTGNR DHFRFEYYPDTGILQLRADA LPQYFKIGKGYDSKLFRIVN

SRGLKNAVTYDGPVPNNEIP AVCLIPCTNGPSAPESESDL NTPTTSSIETSSYSSAATES

SVVSESSSAVDSLTSSSLSS KSESSDVVSSTTNIESSSTA IETTMNSESSTDAGSSSISQ

SESSSTAITSSSETSSSESM SASSTTASNTSIETDSGIVS QSESSSNAL.
```

Any of the above-described polypeptide fragments may be produced recombinantly in *E. coli* or *S. cerevesiae*. Additionally, the invention features Als3/Hyr1 fusion polypeptides and recombinant expression systems producing the same.

*E. coli* Expressed Als3/Hyr1 Fusion Polypeptides

In another aspect, the invention relates to fragments of combinations of Als3 and Hyr1 polypeptides expressed in *E. coli*. In particular, these fragments and linkers joining such fragments are as follows:

Als3

```
                                              (SEQ ID NO: 2)
      A = KTITGVFNSFNSLTWSNAAT YNYKGPGTPTWNAVLGWSLD GTSASPGDTFTLNMPCVFKF

TTSQTSVDLTAHGVKYATCQ FQAGEEFMTFSTLTCTVSNT LTPSIKALGTVTLPLAFNVG

GTGSSVDLEDSKCFTAGTNT VTFNDGGKKISINVDFERSN VDPKGYLTDSRVIPSLNKVS

TLFVAPQCANGYTSGTMGFA NTYGDVQIDCSNIHVGITKG LNDWNYPVSSESFSYTKTCS

SNGIFITYKNVPAGYRPFVD AYISATDVNSYTLSYANEYT CAGGYWQRAPFTLRWTGYRN

SDAGSNG.
```

```
                                              (SEQ ID NO: 3)
      B =          IVIVATTRTVTDS TTAVTTLPFDPNRDKTKTIE ILKPIPTTTITTSYVGVTTS

YSTKTAPIGETATVIVDIPY HTTTTVTSKWTGTITSTTTH TNPTDSIDTVIVQVP
```

Hyr1

```
                                                         (SEQ ID NO: 5)
C = TSRIDRGGIQGFHGDVKVHS GATWAILGTTLCSFFGGLEV EKGASLFIKSDNGPVLALNV

ALSTLVRPVINNGVISLNSK SSTSFSNFDIGGSSFTNNGE IYLDSSGLVKSTAYLYAREW

TNNGLIVAY
```

```
                                                         (SEQ ID NO: 6)
D =           QNQKAAGNIAF GTAYQTITNNGQICLRHQDF VPATKIKGTGCVTADEDTWI

KLGNTILSVEPTHNFYLKDS KSSLIVHAVSSNQTFTVHGF GNGNKLGLTLPLTGNRDHFR

FEYYPDTGILQLRADALPQY FKIGKGYDSKLFRIVNSRGL KNAVTYDGPVPNNEIPAVCL

IPCTNGPSAPESESDLNTPT TSSIET
```

X=is present or absent (designated as -X), wherein X is a linker peptide.
Exemplary fusion polypeptides are as follows:

```
            (SEQ ID NO: 11)          (SEQ ID NO: 12)
    E1 = A-B-X-C-D          E1(-X) = A-B-C-D (SEQ ID NO: 13)          (SEQ ID NO: 14)
    E2 = A-X-C-D            E2(-X) = A-C-D (SEQ ID NO: 15)          (SEQ ID NO: 16)
    E3 = A-X-D              E3(-X) = A-D (SEQ ID NO: 17)          (SEQ ID NO: 18)
    E4 = C-D-X-A-B          E4(-X) = C-D-A-B (SEQ ID NO: 19)          (SEQ ID NO: 20)
    E5 = C-D-X-A            E5(-X) = C-D-A (SEQ ID NO: 21)          (SEQ ID NO: 22)
    E6 = D-X-A-B            E6(-X) = D-A-B (SEQ ID NO: 23)          (SEQ ID NO: 24)
    E7 = D-X-A              E7(-X) = D-A
```

E1=A-B-X-C-D

In another aspect, the invention features an isolated polypeptide including a sequence having substantial identity to the amino acid sequence $$A\text{-}B\text{-}X\text{-}C\text{-}D, \quad (\text{SEQ ID NO: 11})$$

wherein A is SEQ ID NO: 2;
wherein B is SEQ ID NO: 3;
wherein X is absent or is a linker peptide;
wherein C is SEQ ID NO: 5; and
wherein D is SEQ ID NO: 6.

In some embodiments, the isolated polypeptide is substantially identical to A-B-C-D (SEQ ID NO: 12. In other embodiments, the polypeptide is A-B-C-D (SEQ ID NO: 12).

E2=A-X-C-D

In another aspect, the invention features an isolated polypeptide including a sequence having substantial identity to the amino acid sequence $$A\text{-}X\text{-}C\text{-}D, \quad (\text{SEQ ID NO: 13})$$

wherein A is SEQ ID NO: 2;
wherein X is absent or is a linker peptide;
wherein C is SEQ ID NO: 5; and wherein D is SEQ ID NO: 6.

In some embodiments, the polypeptide is substantially identical to A-C-D (SEQ ID NO: 14). In other embodiments, the polypeptide is A-C-D (SEQ ID NO: 14).

E3=A-X-D

In another aspect, the invention features an isolated polypeptide including a sequence having substantial identity to the amino acid sequence $$A\text{-}X\text{-}D, \quad (\text{SEQ ID NO: 15})$$

wherein A is SEQ ID NO: 2;
wherein X is absent or is a linker peptide; and wherein D is SEQ ID NO: 6.

In some embodiments, the polypeptide is substantially identical to A-D SEQ ID NO: 16). In other embodiments, the polypeptide is A-D (SEQ ID NO: 16).

E4=C-D-X-A-B

In another aspect, the invention features an isolated polypeptide including a sequence having substantial identity to the amino acid sequence $$C\text{-}D\text{-}X\text{-}A\text{-}B, \quad (\text{SEQ ID NO: 17})$$

wherein C is SEQ ID NO: 5;
wherein D is SEQ ID NO: 6;
wherein X is absent or is a linker peptide;
wherein A is SEQ ID NO: 2; and
wherein B is SEQ ID NO: 3.

In some embodiments, the polypeptide is substantially identical to C-D-A-B (SEQ ID NO: 18). In other embodiments, the polypeptide is C-D-A-B (SEQ ID NO: 18).

E5=C-D-X-A

In another aspect, the invention features an isolated polypeptide including a sequence having substantial identity to the amino acid sequence $$C\text{-}D\text{-}X\text{-}A, \quad (\text{SEQ ID NO: 19})$$

wherein C is SEQ ID NO: 5;
wherein D is SEQ ID NO: 6;
wherein X is absent or is a linker peptide; and
wherein A is SEQ ID NO: 2.

In some embodiments, the polypeptide is substantially identical to C-D-A (SEQ ID NO: 20). In other embodiments, the polypeptide is C-D-A (SEQ ID NO: 20).

E6=D-X-A-B

In another aspect, the invention features an isolated polypeptide including a sequence having substantial identity to the amino acid sequence $$D\text{-}X\text{-}A\text{-}B, \quad (\text{SEQ ID NO: 21})$$

wherein D is SEQ ID NO: 6;
wherein X is absent or is a linker peptide;

wherein A is SEQ ID NO: 2; and
wherein B is SEQ ID NO: 3.

In some embodiments, the polypeptide is substantially identical to D-A-B (SEQ ID NO: 22). In other embodiments, the polypeptide is D-A-B (SEQ ID NO: 22).

E7 D-X-A

In another aspect, the invention features an isolated polypeptide including a sequence having substantial identity to the amino acid sequence $$D-X-A, \quad \text{(SEQ ID NO: 23)}$$

wherein D is SEQ ID NO: 6;
wherein X is absent or is a linker peptide; and
wherein A is SEQ ID NO: 2.

In some embodiments, the polypeptide is substantially identical to D-A (SEQ ID NO: 24). In other embodiments, the polypeptide is D-A (SEQ ID NO: 24).

S. cerevisiae Expressed Als3/Hyr1 Fusion Polypeptides

In another aspect, the invention relates to fragments of combinations of Als3 and Hyr1 polypeptides expressed in S. cerevisiae. In particular, these fragments and linkers joining such fragments are as follows:

Als3

X=is present or absent, wherein X is a linker peptide.
S1=A-B-X-C-D (SEQ ID NO: 11) S1(-X)=A-B-C-D (SEQ ID NO: 12)
S2=A-X-C-D-E (SEQ ID NO: 25) S2(-X)=A-C-D-E ((SEQ ID NO: 26)
S3=A-X-D-E (SEQ ID NO: 27) S3(-X)=A-D-E (SEQ ID NO: 28)
S4=C-D-E-X-A-B (SEQ ID NO: 29) S4(-X)=C-D-E-A-B (SEQ ID NO: 30)
S5=C-D-X-A-B (SEQ ID NO: 17) S5(-X)=C-D-A-B (SEQ ID NO: 18)
S6=D-X-A-B (SEQ ID NO: 21) S6(-X)=D-A-B (SEQ ID NO: 22)
S7=D-X-A (SEQ ID NO: 23) S7(-X)=D-A (SEQ ID NO: 24)
S1=A-B-X-C-D In another aspect, the invention features an isolated polypeptide including a sequence having substantial identity to the amino acid sequence $$A-B-X-C-D, \quad \text{(SEQ ID NO: 11)}$$

wherein A is SEQ ID NO: 2;
wherein B is SEQ ID NO: 3;
wherein X is absent or is a linker peptide;
wherein C is SEQ ID NO: 5; and
wherein D is SEQ ID NO: 6.

```
                                                   (SEQ ID NO: 2)
A = KTITGVFNSFNSLTWSNAAT YNYKGPGTPTWNAVLGWSLD GTSASPGDTFTLNMPCVFKF

TTSQTSVDLTAHGVKYATCQ FQAGEEFMTFSTLTCTVSNT LTPSIKALGTVTLPLAFNVG

GTGSSVDLEDSKCFTAGTNT VTFNDGGKKISINVDFERSN VDPKGYLTDSRVIPSLNKVS

TLFVAPQCANGYTSGTMGFA NTYGDVQIDCSNIHVGITKG LNDWNYPVSSESFSYTKTCS

SNGIFITYKNVPAGYRPFVD AYISATDVNSYTLSYANEYT CAGGYWQRAPFTLRWTGYRN

SDAGSNG
                                                   (SEQ ID NO: 3)
B =         IVIVATTRTVTDS TTAVTTLPFDPNRDKTKTIE ILKPIPTTTITTSYVGVTTS

YSTKTAPIGETATVIVDIPY HTTTTVTSKWTGTITSTTTH TNPTDSIDTVIVQVP
```

Hyr1

```
                                                   (SEQ ID NO: 5)
C = TSRIDRGGIQGFHGDVKVHS GATWAILGTTLCSFFGGLEV EKGASLFIKSDNGPVLALNV

ALSTLVRPVINNGVISLNSK SSTSFSNFDIGGSSFTNNGE IYLDSSGLVKSTAYLYAREW

TNNGLIVAY
                                                   (SEQ ID NO: 6)
D =          QNQKAAGNIAF GTAYQTITNNGQICLRHQDF VPATKIKGTGCVTADEDTWI

KLGNTILSVEPTHNFYLKDS KSSLIVHAVSSNQTFTVHGF GNGNKLGLTLPLTGNRDHFR

FEYYPDTGILQLRADALPQY FKIGKGYDSKLFRIVNSRGL KNAVTYDGPVPNNEIPAVCL

IPCTNGPSAPESESDLNTPT TSSIET
                                                   (SEQ ID NO: 10)
E =                     SSYSSAATESSVVS ESSSAVDSLTSSSLSSKSES

SDVVSSTTNIESSSTAIETT MNSESSTDAGSSSISQSESS STAITSSSETSSSESMSASS

TTASNTSIETDSGIVSQSES SSNAL
```

In some embodiments, the polypeptide is substantially identical to A-B-C-D (SEQ ID NO: 12). In other embodiments, the polypeptide is A-B-C-D (SEQ ID NO: 12).
S2=A-X-C-D-E In another aspect, the invention features an isolated polypeptide isolated polypeptide including a sequence having substantial identity to the amino acid sequence (SEQ ID NO: 25)
A-X-C-D-E, wherein A is SEQ ID NO: 2;
wherein X is absent or is a linker peptide;
wherein C is SEQ ID NO: 5;
wherein D is SEQ ID NO: 6; and
wherein E is SEQ ID NO: 10.

In some embodiments, the polypeptide is substantially identical to A-C-D-E (SEQ ID NO: 26). In other embodiments, the polypeptide is A-C-D-E (SEQ ID NO: 26).
S3=A-X-D-E In another aspect, the invention features an isolated polypeptide isolated polypeptide including a sequence having substantial identity to the amino acid sequence (SEQ ID NO: 27)
A-X-D-E, wherein A is SEQ ID NO: 2;
wherein X is absent or is a linker peptide;
wherein D is SEQ ID NO: 6; and
wherein E is SEQ ID NO: 10.

In some embodiments, the polypeptide is substantially identical to A-D-E (SEQ ID NO: 28). In other embodiments, the polypeptide is A-D-E (SEQ ID NO: 28).
S4=C-D-E-X-AB In another aspect, the invention features an isolated polypeptide isolated polypeptide including a sequence having substantial identity to the amino acid sequence (SEQ ID NO: 29)
C-D-E-X-A-B, wherein C is SEQ ID NO: 5;
wherein D is SEQ ID NO: 6;
wherein E is SEQ ID NO: 10;
wherein X is absent or is a linker peptide;
wherein A is SEQ ID NO: 2; and
wherein B is SEQ ID NO: 3.

In some embodiments, the polypeptide is substantially identical to C-D-E-A-B (SEQ ID NO: 30). In other embodiments, the polypeptide is C-D-E-A-B (SEQ ID NO: 30).
S5=C-D-X-A-B In another aspect, the invention features an isolated polypeptide isolated polypeptide including a sequence having substantial identity to the amino acid sequence (SEQ ID NO: 17)
C-D-X-A-B, wherein C is SEQ ID NO: 5;
wherein D is SEQ ID NO: 6;
wherein X is absent or is a linker peptide;
wherein A is SEQ ID NO: 2; and
wherein B is SEQ ID NO: 3.

In some embodiments, the polypeptide is substantially identical to C-D-A-B (SEQ ID NO: 18). In other embodiments, the polypeptide is C-D-A-B (SEQ ID NO: 18).
S6=D-X-A-B In another aspect, the invention features an isolated polypeptide isolated polypeptide including a sequence having substantial identity to the amino acid sequence (SEQ ID NO: 21)
D-X-A-B, wherein D is SEQ ID NO: 6;
wherein X is absent or is a linker peptide;
wherein A is SEQ ID NO: 2; and
wherein B is SEQ ID NO: 3.

In some embodiments, the polypeptide is substantially identical to D-A-B (SEQ ID NO: 22). In other embodiments, the polypeptide is D-A-B (SEQ ID NO: 22).
S7=D-X-A In another aspect, the invention features an isolated polypeptide isolated polypeptide including a sequence having substantial identity to the amino acid sequence (SEQ ID NO: 23)
D-X-A, wherein D is SEQ ID NO: 6;
wherein X is absent or is a linker peptide; and
wherein A is SEQ ID NO: 2.

In some embodiments, the polypeptide is substantially identical to D-A (SEQ ID NO: 24). In other embodiments, the polypeptide is D-A (SEQ ID NO: 24).

In other aspects, the invention features an isolated nucleic acid molecule which encodes any of the polypeptides or fusion polypeptides described herein.

In another aspect, the invention features an isolated nucleic acid molecule including a nucleic acid sequence which is substantially identical to any of the isolated nucleic acid molecule which encodes any of the polypeptides or fusion polypeptides described herein.

The invention further features a vector including any of the nucleic acid molecules encoding the polypeptides or fusion polypeptides described herein. The invention accordingly also provides vectors containing the nucleic acids of the invention. Suitable expression vectors are well-known in the art and include vectors capable of expressing a nucleic acid operatively linked to a regulatory sequence or element such as a promoter region or enhancer region that is capable of regulating expression of the nucleic acid. Appropriate expression vectors include vectors that are replicable in eukaryotic cells and/or prokaryotic cells and vectors that remain episomal or integrate into the host cell genome.

The invention also provides a method for expression of a polypeptide as disclosed herein by culturing cells containing a nucleic acid that encodes the polypeptide under conditions suitable for expression of polypeptide. Thus, there is provided a method for the recombinant production of a polypeptide of the invention by expressing the nucleic acid sequences encoding the polypeptide in suitable host cells. Recombinant DNA expression systems that are suitable for production of polypeptides are described herein and are well-known in the art. For example, the above-described nucleotide sequences can be incorporated into vectors for further manipulation. Vectors can include a recombinant DNA or RNA plasmid or virus containing discrete elements that are used to introduce heterologous DNA into cells for either expression or replication thereof.

Similarly, the invention features a cell including any of the nucleic acid molecules encoding polypeptides or fusion polypeptides described herein.

In another aspect, the invention features a method of producing a recombinant polypeptide, the method including the steps of: (a) providing a cell transformed with the nucleic acid molecule of encoding an polypeptide or fusion polypeptide described herein positioned for expression in the cell; (b) culturing the transformed cell under conditions for expressing the nucleic acid molecule, wherein the culturing results in expression of the recombinant polypeptide; and (c) isolating the recombinant polypeptide. In some embodiments, cell is a bacterium (e.g., *E. coli*). In other embodiments, the cell is a yeast cell (e.g., *Saccharomyces cerevisae*). In another aspect, the invention features a recombinant polypeptide produced according to this aforementioned method.

In another aspect, the invention features a substantially pure antibody that specifically recognizes and binds to any one of the polypeptides described herein.

In yet another aspect, the invention features an antigenic composition including the aforementioned polypeptides and a pharmaceutically acceptable carrier, diluent, and/or excipient. In some embodiments, the composition further includes an adjuvant.

In another aspect, the invention features a method of inducing an immune response in a mammal against an antigen including administering any of the aforementioned polypeptides, or the aforementioned antigenic composition to the mammal (e.g., a human), wherein the polypeptide or the composition induces an immune response against the antigen in the mammal. Typically, the mammal is administered a single dose of the polypeptide or the composition. In some embodiments, the mammal is administered a plurality of doses of the polypeptide or the composition. In some embodiments, the plurality of doses are administered at least one day apart (e.g., the plurality of doses are administered at least two weeks apart). In yet other embodiments, the composition is administered twice.

In another aspect, the invention features a vaccine including an immunogenic amount of any of the aforementioned polypeptides, and a pharmaceutically acceptable excipient. In some embodiments, the vaccine includes a mixture of distinct polypeptides of any one of the aforementioned polypeptides. In some embodiments, the vaccine further includes an adjuvant (Alhydrogel). The vaccine of the invention is useful for vaccination of a mammal (e.g., a human) against candidiasis, a bacterial infection such as one caused by *Staphylococcus* or *Acinetobacter*. Typically, the vaccine is to be administered by intramuscular, subcutaneous, or intradermal administration. The vaccine may also be administered by intramuscular administration. Vaccination may further includes administering a booster dose. Candidiasis may take many forms such as disseminated candidiasis (e.g., hematogenously disseminated candidiasis) or mucosal candidiasis. Candidiasis is caused, for example, by *Candida albicans*, *Candida glabrata*, *Candida krusei*, *Candida parapsilosis*, or *Candida tropicalis*. In some embodiments, vaccination is against *Acinetobacter* or *Staphylococcus*.

In other aspects, the invention features a method of producing a chimeric vaccine including the steps of: (a) providing a phage, yeast, or virus; (b) inserting into the phage, yeast, or virus a nucleic acid molecule that encodes any of the aforementioned polypeptides; (c) allowing expression of the polypeptide in the phage, yeast, or virus; (d) isolating the phage, yeast, or virus of step (c) including the expressed polypeptide; and (e) adding a pharmaceutically acceptable excipient to the isolated phage, yeast, or virus of step (d). In some embodiments, the polypeptide is displayed on the surface of the phage, yeast, or virus following step (c).

In other aspects, the invention features an isolated monoclonal antibody that binds to any of the aforementioned polypeptides or fusion polypeptides. Typically, the antibody is human or humanized. The antibody may also be chimeric. The antibody may also be produced recombinantly. A diagnostic composition including these antibodies is within the invention.

Another aspect of the invention relates to a pharmaceutical composition including any of the aforementioned antibodies alone or in combination, and a pharmaceutically acceptable excipient. In some embodiments, the pharmaceutical composition includes a mixture of antibodies with a plurality of distinct specificities.

In still another aspect, the invention features a pharmaceutical composition including polyclonal antibodies that bind to the any of the polypeptides or fusion polypeptides described herein, or that bind to a mixture of distinct polypeptides of such described polypeptides. In some embodiments, the pharmaceutical composition is for use in the passive immunization of a mammal (e.g., a mammal) against candidiasis or a bacterial infection. Typically, the pharmaceutical composition is administered by intramuscular, subcutaneous, or intradermal administration. In some embodiments, the pharmaceutical composition is administered by intramuscular administration. In some embodiments, the candidiasis is disseminated candidiasis, for example, hematogenously disseminated candidiasis. In other embodiments, the candidiasis is mucosal candidiasis. In some embodiments, candidiasis is caused by *Candida albicans*, *Candida glabrata*, *Candida krusei*, *Candida parapsilosis*, or *Candida tropicalis*. In some embodiments, passive immunization is against *Acinetobacter* or *Staphylococcus*.

In another aspect, the invention features a method of passive immunization of a mammal (e.g., a human) against candidiasis or a bacterial infection such as one caused by *Staphyloccocus* or *Acinetobacter* including administering to the mammal an effective amount of any of the pharmaceutical compositions disclosed herein, thereby passively immunizing the mammal against the candidiasis. In some embodiments, the pharmaceutical composition is administered by intramuscular, subcutaneous, or intradermal administration. In other embodiments, the pharmaceutical composition is administered by intramuscular administration. In some embodiments, the candidiasis is disseminated candidiasis, for example, hematogenously disseminated candidiasis. In some embodiments, the candidiasis is mucosal candidiasis. In some embodiments, the candidiasis is caused by *Candida albicans*, *Candida glabrata*, *Candida krusei*, *Candida parapsilosis*, or *Candida tropicalis*.

In another aspect, the invention features an isolated polypeptide including a sequence having substantial identity to the amino acid sequence (SEQ ID NO: 31)
A-B-X-C-D-E, wherein A is absent or is SEQ ID NO: 2;
wherein B is absent or is SEQ ID NO: 3;
wherein X is absent or is a linker peptide;
wherein C is absent or is SEQ ID NO: 5;
wherein D is absent or is SEQ ID NO: 6; and
wherein E is absent or is SEQ ID NO: 10,
provided that two or more of A, B, C, D and E are present in the polypeptide.

In some embodiments, the polypeptide is A-B-C-D-E (SEQ ID NO: 32); A-B-X-C-D (SEQ ID NO: 11); A-B-C-D (SEQ ID NO: 12); A-X-C-D-E (SEQ ID NO: 25); A-C-D-E (SEQ ID NO: 26); A-X-C-D (SEQ ID NO: 13); A-C-D (SEQ ID NO: 14); A-X-D-E (SEQ ID NO: 27); A-D-E (SEQ ID NO: 28); A-X-D (SEQ ID NO: 15); or A-D (SEQ ID NO: 16).

In another aspect, the invention features an isolated polypeptide including a sequence having substantial identity to the amino acid sequence $$C-D-E-X-A-B, \quad (SEQ\ ID\ NO:\ 29)$$

wherein C is absent or is SEQ ID NO: 5;
wherein D is absent or is SEQ ID NO: 6;
wherein E is absent or is SEQ ID NO: 10;
wherein X is absent or is a linker peptide;
wherein A is absent or is SEQ ID NO: 2;
wherein B is absent or is SEQ ID NO: 3,
provided that two or more of C, D, E, A, and B are present in the polypeptide.

In some embodiments, the polypeptide is C-D-E-A-B (SEQ ID NO: 30); C-D-X-A-B (SEQ ID NO: 17); C-D-A-B (SEQ ID NO: 18); D-X-A-B (SEQ ID NO: 21); D-A-B (SEQ ID NO: 22): D-X-A (SEQ ID NO: 23); or D-A (SEQ ID NO: 24).

In still other aspects, the invention features compositions and methods as disclosed herein that are based, at least in part, on the proposition that an immune response, such as antibodies and other mechanisms, that target the a *Candida* HYR1 polypeptide and confer protection from *Acinetobacter* infection such as *Acinetobacter baumannii*. Active or passive immunization approaches using the a HYR1 polypeptide fragment or an Als3/Hyr1 polypeptide fusion proteins disclosed herein are useful to protect against infections caused by gram negative rod bacteria, including, but not limited to, *Acinetobacter baumannii*. Some uses of the compositions and methods disclosed herein include passive vaccination of acutely at-risk patients with a dose of anti-HYR1 or anti-Als/Hyr1 antibody to prevent the acquisition of *Acinetobacter baumannii* infection. Additionally, patients with active *Acinetobacter baumannii* infection can be treated with the antibody alone or combined with other antibacterial agents. Alternatively, patients who are at risk of developing such infections, such as, for example, military personnel, can be actively vaccinated with Hyr1 or Als3/Hyr1 polypeptides or specific *Acinetobacter baumannii* polypeptides disclosed herein to prevent such infections.

In addition to vaccination of subjects susceptible to *Acinetobacter* or *Candida* infections or both, the vaccine compositions of the present invention can also be used to treat, immunotherapeutically, subjects suffering from a variety of gram negative bacterial infections. Accordingly, vaccines that contain one or more of the polypeptides and/or antibody compositions described herein in combination with adjuvants, can act for the purposes of prophylactic or therapeutic treatment of infections from gram negative bacteria. In one embodiment, vaccines of the present invention will induce the body's own immune system to seek out and inhibit gram negative bacteria or *Candida* or both.

Vaccines according to the invention refer to a composition that can be administered to an individual to protect the individual against an infectious disease. Vaccines protect against diseases by inducing or increasing an immune response in an animal against the infectious disease. An exemplary infectious disease amenable to treatment with the vaccines of the invention include severe pneumonia, infections of the urinary tract, infections of the bloodstream and infections of other parts of the body. The vaccine-mediated protection can be humoral and/or cell mediated immunity induced in host when a subject is challenged with, for example, or an immunogenic portion of a polypeptide or protein described herein.

Accordingly, in some embodiments, the invention provides a method of treating or preventing an infection from gram negative bacteria in a subject in need thereof by administering a therapeutically effective amount of a pharmaceutical composition as disclosed herein or a vaccine composition as disclosed herein. For example, the invention provides methods of treating or preventing infections caused by one or more gram negative bacteria including bacteria of the *Acinetobacter* genus, such as *A. baumannii, A. iwoffii, A. haemolyticus, A. calcoaceticus, A. johnsonii, A. radioresistens*, and *A. junii*, bacteria of the *Haemophilus* genus, such as *H. aegyptius, H. aphrophilus, H. avium, H. ducreyi, H. felis, H. haemolyticus, H. influenza, H. parainfluenzae, H. paracuniculus, H. parahaemolyticus, H. pittmaniae*, and *H. somnus*, bacteria of the *Bordetella* genus, such as *B. ansorpii, B avium, B. bronchiseptica, B. hinzii, B. holmesii, B. parapertussis, B. pertussis, B. petrii*, and *B. trematum*, bacteria of the *Salmonella* genus, such as *S. typhimurium, S. bongori, S. enterica* subsp. *enterica, S. enterica* subsp. *salamae, S. arizonae, S. enterica* subsp. *diarizonae, S. enterica* subsp. *houtenae*, and *S. enterica* subsp. *indica*, bacteria of the *Yersina* genus, such as *Yersina pseudotuber, Y. aldovae, Y. aleksiciae, Y. bercovieri, Y. enterocolitica, Y. frederiksenii, Y. intermedia, Y. kristensenii, Y. mollaretii, Y. pestis, Y. pseudotuberculosis, Y. rohdei*, and *Y. ruckeri*, bacteria of the *Escherichia* genus, such as *E. albertii, E. blattae, E. coli, E. fergusonii, E. hermannii* and *E. vulneris*, bacteria of the *Pedobacter* genus, such as *P. heparinus, P. roseus* sp. *nov*. and *P. aquatilis* sp. *nov*, bacteria of the *Pseudomonas* genus, such as *P. aeruginosa, P. alcaligenes, P. mendocina, P. fluorescens, P. monteilii, P. oryzihabitans, P. luteola, P. putida, P. cepacia, P. stutzeri, P. maltophilia, P. putrefaciens, P. mallei* and *P. pseudomallei*, or bacteria of the *Klebsiella* genus, such as *K. pneumoniae, K. planticola K. oxytoca* and *K. rhinoscleromatis*. In other embodiments, *Candida* species as disclosed herein may be treated or prevented.

By "adjuvant" is meant one or more substances that cause stimulation of the immune system. In this context, an adjuvant is used to enhance an immune response to one or more vaccine antigens or antibodies. An adjuvant may be administered to a subject before, in combination with, or after administration of the vaccine or antibody. Examples of chemical compounds used as adjuvants include, but are not limited to, aluminum compounds (e.g., alum, Alhydrogel), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

By "antibody" is meant whole antibodies, immunoglobulins, or any antigen-binding fragment or single chains thereof. Antibodies, as used herein, can be mammalian (e.g., human or mouse), humanized, chimeric, recombinant, synthetically produced, or naturally isolated, and can be, e.g., monoclonal or polyclonal. In most mammals, including humans, whole antibodies have at least two heavy (H) chains and two light (L) chains connected by disulfide bonds. Each heavy chain consists of a heavy chain variable region (abbreviated herein as $V_H$) and a heavy chain constant region. The heavy chain constant region consists of three domains, $C_H1$, $C_H2$, and $C_H3$ and a hinge region between $C_H1$ and $C_H2$. Each light chain consists of a light chain variable region (abbreviated herein as $V_L$) and a light chain constant region. The light chain constant region consists of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies of the present invention include all known forms of antibodies and other protein scaffolds with antibody-like properties. For example, the antibody can be a human antibody, a humanized antibody, a bispecific antibody, a chimeric antibody, or a protein scaffold with antibody-like properties, such as fibronectin or ankyrin repeats. The antibody also can be a Fab, Fab'2, scFv, SMIP, diabody, nanobody, aptamers, or a domain antibody. The antibody can have any of the following isotypes: IgG (e.g., IgG1, IgG2, IgG3, and IgG4), IgM, IgA (e.g., IgA1, IgA2, and IgAsec), IgD, or IgE.

The term "antibody fragment," as used herein, refers to one or more fragments of an antibody that retain the ability to specifically bind to an antigen. The antigen-binding function of an antibody can be performed by fragments of a full-length antibody, which include but are not limited to: (i) a Fab fragment, a monovalent fragment consisting of the $V_L$, $V_H$, $C_L$, and $C_H1$ domains; (ii) a $F(ab')_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment (Ward et al., *Nature* 341:544-546 (1989)), which consists of a $V_H$ domain; (vii) a dAb which consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., *Science* 242:423-426 (1988) and Huston et al., *Proc. Natl. Acad. Sci. USA* 85:5879-5883 (1988)). These antibody fragments are obtained using conventional techniques known to those with skill in the art, and the fragments are screened for utility in the same manner as are intact antibodies. Antibody fragments can be produced by recombinant DNA techniques, or by enzymatic or chemical cleavage of intact immunoglobulins.

By "antigen" is meant a molecule to which an antibody can selectively bind. The target antigen may be a protein (e.g., an antigenic peptide), carbohydrate, nucleic acid, lipid, hapten, or other naturally occurring or synthetic compound. The target antigen may be a polypeptide or peptide mimic. An antigen may also be administered to an animal to generate an immune response in the animal.

By "carrier" in the context of a conjugate is meant a moiety or particle, e.g., KLH, CRM197, tetanus toxoid, a phage, a yeast, a virus, a virosome, or a recombinant virus-like particle, that is suitable for being linked to or displaying a polypeptide as described herein.

By "chimeric antibody" is meant an immunoglobulin or antibody whose variable regions derive from a first species and whose constant regions derive from a second species. Chimeric antibodies can be constructed, for example, by genetic engineering, from immunoglobulin gene segments belonging to different species (e.g., from a mouse and a human).

By "chimeric vaccine" is meant a vaccine that includes at least two distinct antigens, e.g., joined covalently. An example of a chimeric vaccine is a composition that includes a polypeptide displayed, e.g., on the surface of a particle such as a phage, virus, yeast, virosome, or recombinant virus-like particle.

By "conjugate" is meant a compound that includes a polypeptide of the invention linked to another moiety or particle, e.g., KLH, CRM197, tetanus toxoid, a phage, a yeast, a virus, a virosome, or a recombinant virus-like particle.

By "conservative substitution" in an amino acid sequence is meant replacement of an amino acid for another within a family of amino acids that are related in the chemical nature of their side chains.

Genetically encoded amino acids can be divided into four families: acidic (aspartate, glutamate); basic (lysine, arginine, histidine); nonpolar (alanine, valine, leucine, isoleucine, proline, phenylalanine, methionine, tryptophan); and uncharged polar (glycine, asparagine, glutamine, cysteine, serine, threonine, tyrosine). Phenylalanine, tryptophan, and tyrosine are sometimes grouped as aromatic amino acids. In similar fashion, the amino acids can also be separated into the following groups: acidic (aspartate, glutamate); basic (lysine, arginine, histidine); alipathic (glycine, alanine, valine, leucine, isoleucine, serine, threonine), with serine and threonine optionally grouped separately as alipathic-hydroxyl; aromatic (phenylalanine, tyrosine, tryptophan); amide (asparagine, glutamine); and sulfur-containing (cysteine, methionine).

Whether a change in the amino acid sequence results in a functional variant can be determined by assessing the ability of the variant polypeptide to function in a fashion similar to the wild-type polypeptide using standard methods such as those described herein.

By "diagnostic composition" is meant a composition containing a polypeptide, conjugate, vaccine, or antibody of the invention, formulated for use in conjunction with a diagnostic method.

By "effective amount" in the context of passive immunization using a pharmaceutical composition, e.g., comprising an antibody, is meant the amount of the pharmaceutical composition required to passively immunize in a clinically relevant manner. An effective amount of pharmaceutical composition used to practice the methods of passive immunization described herein varies depending upon the manner of administration, the age, body weight, and general health of the subject. Ultimately, the prescribers will decide the appropriate amount and dosage regimen.

By "flanking amino acid" is meant an amino acid in a polypeptide sequence that is immediately adjacent to the N- or C-terminus of a particular defined sequence. Desirably, a flanking amino acid is present on the N- and/or C-terminus of the amino acid sequence of SEQ ID NO: 1 or 2 or a fragment thereof; and more desirably, 1, 2, 3, 4, 5, 6, 7, 8, 9, or 10 flanking amino acids are present at the N- and/or C-terminus of the amino acid sequence of SEQ ID NO: 1 or 2, or fragment thereof.

By "fusion protein" is meant a protein that includes a polypeptide of the invention, e.g., a peptide fragment or variant, and a fusion partner.

By "fusion partner" is meant a heterologous sequence that can be fused to a polypeptide or peptide of the invention, e.g., one or more of Peptide 3-11 or variants thereof. Examples of fusion partners are described herein and include detection markers, stabilizing domains, sequences which aid in production or purification of the protein, or domains which increase the antigenicity of the polypeptide.

By "immunogenic" is meant any substance that is capable of inducing an immune response in a subject.

By "immunogenic amount" in the context of a vaccine is meant an amount of the vaccine required to induce an immune response in a subject in a clinically relevant manner. An immunogenic amount of vaccine used to practice the methods of vaccination as described herein varies depending upon the manner of administration, the age, body weight, and general health of the subject. Ultimately, the prescribers will decide the appropriate amount and dosage regimen.

By "isolated" or "purified" is meant separated from other naturally accompanying components. Typically, a compound (e.g., nucleic acid, polypeptide, antibody, or small molecule) is substantially isolated when it is at least 60%, by weight, free from the proteins and/or naturally occurring organic molecules with which it is naturally associated. The definition also extends, e.g., to a polypeptide or nucleic acid molecule separated from its flanking sequences (e.g., for an amino acid sequence, isolated refers to a sequence that is free from the flanking amino acids with which the sequence is naturally associated in a polypeptide). In some instances, the compound is at least 75%, more preferably at least 90%, and most preferably at least 99%, by weight, isolated. An isolated compound, e.g., polypeptide, may be obtained by standard techniques, for example, by extraction from a natural source (e.g., purification from a cell infected with *Candida*); by expression of a recombinant nucleic acid encoding an Als3 or CNA fragment or variant, or a fusion protein thereof; or by chemically synthesizing the polypeptide. Purity can be measured by any appropriate method, e.g., by column chromatography, polyacrylamide gel electrophoresis, or HPLC analysis.

By "linked to" or "conjugated to" in the context of a conjugate is meant a covalent or non-covalent interaction between the polypeptide and the carrier or fusion partner. Non-covalent interactions include, but are not limited to, hydrogen bonding, ionic interactions among charged groups, electrostatic binding, van der Waals interactions, hydrophobic interactions among non-polar groups, lipophobic interactions, and Log P-based attractions.

By "linker" as used herein is meant an amino acid sequence of one or more amino acids in length, e.g., that is not cleavable, for example, by auto-cleavage, enzymatic, or chemical cleavage. The linker can include nonpolar, polar, and/or charged amino acids. In some embodiments, linkers include or consist of flexible portions, e.g., regions without significant fixed secondary or tertiary structure. Exemplary flexible linkers are glycine-rich linkers, e.g., containing at least 50%, 60%, 65%, 70%, 75%, 80%, 85%, 90%, 95%, or even 100% glycine residues. Linkers may also contain, e.g., serine residues. In some cases, the amino acid sequence of linkers consists only of glycine and serine residues. A linker can be, for example, 1 to 100 amino acids in length, for example, 1, 2, 3, 4, 5, 10, 15, 20, 25, 30, 35, 40, 45, 50, 55, 60, 65, 70, 75, 80, 85, 90, 95, or 100 amino acids in length.

By "monoclonal antibody" is meant an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. Monoclonal antibodies can be prepared using any art recognized technique and those described herein such as, for example, a hybridoma method, as described by Kohler et al., *Nature* 256:495 (1975), a transgenic animal (e.g., Lonberg et al., *Nature* 368(6474):856-859 (1994)), recombinant DNA methods (e.g., U.S. Pat. No. 4,816,567), or using phage, yeast, or synthetic scaffold antibody libraries using the techniques described in, for example, Clackson et al., *Nature* 352:624-628 (1991) and Marks et al., *J. Mol. Biol.* 222:581-597 (1991).

By "nucleic acid molecule" is meant a molecule, e.g., RNA or DNA, having a sequence of two or more covalently bonded, naturally occurring or modified nucleotides. The nucleic acid molecule may be, e.g., single or double stranded, and may include modified or unmodified nucleotides, or mixtures or combinations thereof. Various salts, mixed salts, and free acid forms are also included.

By "patient" or "subject" is meant a mammal, including, but not limited to, a human or non-human mammal, such as a bovine, equine, canine, ovine, or feline.

The terms "peptide," "polypeptide," and "protein" are used interchangeably and refer to any chain of two or more natural or unnatural amino acids, regardless of post-translational modification (e.g., glycosylation or phosphorylation), constituting all or part of a naturally-occurring or non-naturally occurring polypeptide or peptide, as is described herein. Such polypeptides typically are continuous and unbranched peptide. A peptide is a short polymer of amino acid monomers. "Proteins" are intended to include one or more polypeptides arranged in a biologically functional way. The amino acids comprising the polypeptides of the invention may be linked by peptide bonds or other bonds, for example, ester or ether bonds. The amino acids comprising the polypeptides of the invention can include non-genetically coded amino acids that either occur naturally or are chemically synthesized.

A polypeptide of the invention can also encompass one or more conservative substitutions. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are also included within polypeptides of the invention so long as the polypeptide retains some or all of its function as described herein.

The invention polypeptides can also include derivatives, analogues and functional mimetics thereof, provided that such polypeptide retains some or all of its function as disclosed herein. For example, derivatives can include chemical modifications of the polypeptide such as alkylation, acylation, carbamylation, iodination, or any modification that derivatizes the polypeptide. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine. Also included as derivatives or analogues are those peptides which contain one or more naturally occurring amino acid derivatives of the twenty standard amino acids, for example, 4-hydroxyproline, 5-hydroxylysine, 3-methylhistidine, homoserine, ornithine or carboxyglutamate, and can include amino acids that are not linked by peptide bonds. Polypeptides of the present invention also include any polypeptide having one or more additions and/or deletions of residues, relative to the sequence of a polypeptide whose sequence is shown herein, so long as immunogenic activity as disclosed herein is maintained.

The invention polypeptides can be isolated by a variety of methods well-known in the art, for example, recombinant expression systems, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, (1990)). Alternatively, the isolated polypeptides of the present invention can be obtained using well-known recombinant methods (see, for example, Ausubel et al., "Immunology," *Short Protocols in Molecular Biology, John Wiley & Sons, Inc.* Chapter 11. Page 11.1-11.29 (1999); Sambrook and Russell, "Molecular Cloning: A Laboratory Manual," *Cold Spring Harbor Laboratory* (2001)). The methods and conditions for biochemical purification of a polypeptide of the invention can be chosen by those skilled in the art, and purification monitored, for example, by an immunological assay or a functional assay.

An example of the means for preparing an invention polypeptide is to express nucleic acids encoding a polypeptide of the invention in a suitable host cell, such as a bacterial cell, a yeast cell, an amphibian cell such as an oocyte, or a mammalian cell, using methods well known in the art, and recovering the expressed polypeptide, again using well-known purification methods, so described herein. Invention polypeptides can be isolated directly from cells that have been transformed with expression vectors as described herein. The invention polypeptides can also be produced by chemical synthesis. Methods for chemically synthesizing polypeptides are well known in the art and are commercially available.

Recombinantly expressed polypeptides of the invention can also be expressed as fusion proteins with appropriate fusion partners. An appropriate fusion partner can be an amino acid sequence that is not normally connected to the amino acid sequence such as an heterologous sequence, which serves a particular function or provides additional characteristic to the polypeptides of the invention. Non-limiting examples of suitable heterologous sequences include a detectable marker, a stabilizing domain, a carrier protein for the generation of antibodies, a linker sequence and a sequence that aids in the purification of the polypeptide. Sequences that can aid in the purification of the invention polypeptides include affinity tags, such as glutathione S transferase (GST) or poly His. Thus, in some aspects, the invention provide a fusion protein having a polypeptide as disclosed herein fused to a heterologous sequence, a carrier protein, an affinity tag or a linker sequence or other polypeptides as disclosed herein.

As used herein, a natural amino acid is a natural α-amino acid having the L-configuration, such as those normally occurring in natural polypeptides. Unnatural amino acid refers to an amino acid that normally does not occur in polypeptides, e.g., an epimer of a natural α-amino acid having the L configuration, that is to say an amino acid having the unnatural D-configuration; or a (D,L)-isomeric mixture thereof; or a homolog of such an amino acid, for example, a β-amino acid, an α,α-disubstituted amino acid, or an α-amino acid wherein the amino acid side chain has been shortened by one or two methylene groups or lengthened to up to 10 carbon atoms, such as an α-amino alkanoic acid with 5 up to and including 10 carbon atoms in a linear chain, an unsubstituted or substituted aromatic (α-aryl or α-aryl lower alkyl), for example, a substituted phenylalanine or phenylglycine.

The terms "pharmaceutically acceptable carrier" and "pharmaceutically acceptable excipient" are used interchangeably and mean a carrier or excipient that is physiologically acceptable to the treated patient while retaining the therapeutic properties of the compound with which it is administered. One exemplary pharmaceutically acceptable carrier substance is physiological saline. Other physiologically acceptable carriers and their formulations are known to those skilled in the art and described, for example, in Remington's Pharmaceutical Sciences, (20$^{th}$ edition), ed. A. Gennaro, 2000, Lippincott, Williams & Wilkins, Philadelphia, Pa.

By "pharmaceutical composition" is meant a composition containing a polypeptide, conjugate, vaccine, or antibody of the invention, formulated with a pharmaceutically acceptable excipient, and manufactured or sold with the approval of a governmental regulatory agency as part of a therapeutic regimen for the treatment or prevention of a disease or event in a mammal. Pharmaceutical compositions can be formulated, for example, for intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

By "specifically binds" is meant the preferential association of a binding moiety (e.g., an antibody, antibody fragment, receptor, ligand, or small molecule portion of an agent as described herein) to a target molecule (e.g., a polypeptide or conjugate including same) or to a cell or tissue bearing the target molecule (e.g., a cell surface antigen, such as a receptor or ligand) and not to non-target molecules, cells, or tissues lacking the target molecule. It is recognized that a certain degree of non-specific interaction may occur between a binding moiety and a non-target molecule (present alone or in combination with a cell or tissue). Nevertheless, specific binding may be distinguished as mediated through specific recognition of the target molecule. Specific binding results in a stronger association between the binding moiety (e.g., an antibody) and the target molecule (e.g., a polypeptide or conjugate including same) than between the binding moiety and, e.g., non-target molecules or other compositions lacking the target molecule. Specific binding typically results in greater than 2-fold, preferably greater than 5-fold, more preferably greater than 10-fold and most preferably greater than 100-fold increase in amount of bound binding moiety (per unit time) to e.g., a cell or tissue bearing the target molecule or marker as compared to a cell or tissue lacking that target molecule or marker. Binding moieties bind to the target molecule or marker with a dissociation constant of e.g., less than $10^{-6}$M, less than $10^{-7}$M, $10^{-8}$M, $10^{-9}$M, $10^{-10}$M, $10^{-11}$M, or $10^{-12}$M, or even less than $10^{-13}$M, $10^{-14}$M, or $10^{-15}$M. Specific binding to a protein under such conditions requires a binding moiety that is selected for its specificity for that particular protein. A variety of assay formats are appropriate for selecting binding moieties (e.g., antibodies) capable of specifically binding to a particular target molecule. For example, solid-phase ELISA immunoassays are routinely used to select monoclonal antibodies specifically immunoreactive with a protein. See Harlow & Lane, Antibodies, A Laboratory Manual, Cold Spring Harbor Publications, New York (1988), for a description of immunoassay formats and conditions that can be used to determine specific immunoreactivity.

By "substantially identical" is meant an amino acid sequence or nucleic acid sequence that exhibits at least 50% identity to a reference sequence. Such a sequence is generally at least, e.g., 50%, 60%, 70%, 75%, 80%, 85%, 90%, 95%, 96%, 97%, 98%, or 99% identical at the amino acid level or nucleic acid level to a reference sequence. In general, for polypeptides, the length of comparison sequences can be at least five amino acids, e.g., 10, 20, 30, 40, 50, 60, 70, 80, 90, 100, 125, 150, 175, 200, 250, 300, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., J. Mol. Biol. 147:195-7, 1981) and BLAST (Basic Local Alignment Search Tool; Altschul et al., J. Mol. Biol. 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared.

By "Staphylococcus aureus skin or soft tissue infection", "Staphylococcus aureus SSTI", "Staphylococcus aureus skin/skin structure infection", and "Staphylococcus aureus SSSI" are used interchangeably herein and refer to a skin or soft tissue infection (e.g. cellulitis, soft tissue abscess, dermonecrosis, myositis, or other infections) resulting from S. aureus entering the body at a site where a cut, scrape, bite, or other wound has broken the skin. In some instances, S. aureus SSSI is the result of S. aureus living on the body, and may occur spontaneously in the absence of a visible site of skin injury or wound. Such infections may affect the layers of the skin or deeper tissues, such as muscle and connective tissue (the interlacing framework of tissue that forms ligaments, tendons, and other supporting structures of the body). Skin abscesses may also occur in areas of the skin where the body has been fighting a S. aureus infection. The more important strains of S. aureus responsible for skin or soft tissue infections are the antibiotic-resistant Staphylococcus known as methicillin-resistant Staphylococcus aureus (MRSA); vancomycin-resistant and daptomycin-resistant strains of S. aureus may also cause SSSI. MRSA is resistant to commonplace antibiotics. Staphylococcus aureus SSSIs may also be caused by methicillin-sensitive Staphylococcus aureus (MSSA).

Mammals which are at risk of developing a S. aureus skin or soft tissue infection can be treated in a prophylactic mode. Alternatively, mammals may be treated when presenting with symptoms of a S. aureus skin or soft tissue infection. Vaccination as described herein will reduce the severity, delay, or prevent the development of symptoms. Mammals are at elevated risk of infection if they are hospitalized or living in an institutionalized community, antibiotic treated, or immunosuppressed including children having HIV/AIDS or other diseases that compromise immune function, individuals having frequent contact with the healthcare system, having a chronic illness such as diabetes, cancer, HIV/AIDS, being very young or very old, frequent use of antibiotics, having an open wound, dermatitis or skin lesions, poor nutrition or poor hygiene. Other mammals at risk include those living in crowded living conditions, military personnel, especially deployed troops, athletes, and prison inmates. Still others at risk of developing a S. aureus skin or soft tissue infection are those individuals previously having such infections or individuals scheduled for or having had a surgical or invasive medical procedure.

A "target molecule" or "target cell" is meant a molecule (e.g., a polypeptide, epitope, antigen, receptor, or ligand) or cell to which a binding moiety (e.g., an antibody) can specifically bind. In some instances, target molecules are exposed on the exterior of a target cell (e.g., a cell surface or secreted protein), but target molecules may alternately or also be present in the interior of a target cell.

By "treating" or "treatment" is meant the medical management of a patient with the intent to cure, ameliorate, stabilize, reduce the likelihood of, or prevent a disease, pathological condition, disorder, or event, by administering a pharmaceutical composition. This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief of symptoms rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

By "vaccine," as used herein, is meant a composition that elicits an immune response in a subject to which it is administered.

By "vaccinate," as used herein, is meant to treat a patient by administering a vaccine, e.g., to prevent or ameliorate a disease, pathological condition, disorder, or event.

By "variant" in the context of a polypeptide or portion thereof as described herein, or a nucleic acid molecule encoding same, is meant to include substitutions or alterations in the amino acid sequence or nucleic acid sequence, e.g., resulting in a substantially identical sequence. A polypeptide having a variant sequence may maintain at least one biological activity of the original polypeptide, e.g., immunogenic activity. The term "variant" includes, e.g., amino acid insertional derivatives such as amino and/or carboxyl-terminal fusions, as well as intrasequence insertions of single or multiple amino acids. Insertional amino acid variants are those in which one or more amino acid residues are introduced into a predetermined site in the protein. Random insertion is also possible with suitable screening of the resulting product. Deletional variants are characterized by removal of one or more amino acids from the sequence. Substitutional amino acid variants are those in which at least one residue inserted in its place. Where the protein is derivatized by amino acid substitution, amino acids are generally replaced by conservative substitutions, e.g., other amino acids having similar physical chemical properties such as hydrophobicity, hydrophilicity, electronegativity, bulky sidechains and the like.

For purposes of the present invention, variants also include single or multiple substitutions, deletions and/or additions of any component(s) naturally or artificially associated with the portion of a naturally occurring protein from which the polypeptide may be derived, such as carbohydrate, lipid and/or other proteinaceous moieties. All such molecules are encompassed by the term "variant."

By "variant sequence" is meant the amino acid or nucleic acid sequence of a variant as defined herein.

Other features and advantages of the invention will be apparent from the following Detailed Description and the claims.

DETAILED DESCRIPTION OF THE INVENTION

The identification of the Als3 and Hyr1 polypeptide fragments and Als3/Hyr1 fusion polypeptides and other compositions described herein allow, e.g., for the effective treatment of and vaccination against candidiasis or bacterial infections such as those caused by any of those disclosed herein.

The invention provides polypeptides, e.g., derived from Als3 or Hyr1 or Als3/Hyr1 fusion polypeptides, conjugates, vaccines, antibodies, compositions, methods of vaccination using same, and methods of production of same, as described in further detail below.

Polypeptides

The invention features polypeptides derived from Als3 or Hyr1. The amino acid sequence of rAls3 protein is as follows:

```
  1 KTITGVFNSFNSLTWSNAAT YNYKGPGTPTWNAVLGWSLD GTSASPGDTFTLNMPCVFKF
 61 TTSQTSVDLTAHGVKYATCQ FQAGEEFMTFSTLTCTVSNT LTPSIKALGTVTLPLAFNVG
121 GTGSSVDLEDSKCFTAGTNT VTFNDGGKKISINVDFERSN VDPKGYLTDSRVIPSLNKVS
181 TLFVAPQCANGYTSGTMGFA NTYGDVQIDCSNIHVGITKG LNDWNYPVSSESFSYTKTCS
241 SNGIFITYKNVPAGYRPFVD AYISATDVNSYTLSYANEYT CAGGYWQRAPFTLRWTGYRN
301 SDAGSNGIVIVATTRTVTDS TTAVTTLPFDPNRDKTKTIE ILKPIPTTTITTSYVGVTTS
361 YSTKTAPIGETATVIVDIPY HTTTTVTSKWTGTITSTTTH TNPTDSIDTVIVQVP
```

The amino acid sequence of the rHyr1 protein is as follows:

```
  1 TSRIDRGGIQGFHGDVKVHS GATWAILGTTLCSFFGGLEV EKGASLFIKSDNGPVLALNV
 61 ALSTLVRPVINNGVISLNSK SSTSFSNFDIGGSSFTNNGE IYLDSSGLVKSTAYLYAREW
121 TNNGLIVAYQNQKAAGNIAF GTAYQTITNNGQICLRHQDF VPATKIKGTGCVTADEDTWI
181 KLGNTILSVEPTHNFYLKDS KSSLIVHAVSSNQTFTVHGF GNGNKLGLTLPLTGNRDHFR
241 FEYYPDTGILQLRADALPQY FKIGKGYDSKLFRIVNSRGL KNAVTYDGPVPNNEIPAVCL
301 IPCTNGPSAPESESDLNTPT TSSIETSSYSSAATESSVVS ESSSAVDSLTSSSLSSKSES
361 SDVVSSTTNIESSSTAIETT MNSESSTDAGSSSISQSESS STAITSSSETSSSESMSASS
401 TTASNTSIETDSGIVSQSES SSNAL
```

The invention features polypeptides having substantial identity to any of the polypeptides described herein, including the following.

Als3

(SEQ ID NO: 2)
```
A = KTITGVFNSFNSLTWSNAAT YNYKGPGTPTWNAVLGWSLD GTSASPGDTFTLNMPCVFKF
    TTSQTSVDLTAHGVKYATCQ FQAGEEFMTFSTLTCTVSNT LTPSIKALGTVTLPLAFNVG
```

```
GTGSSVDLEDSKCFTAGTNT VTFNDGGKKISINVDFERSN VDPKGYLTDSRVIPSLNKVS

TLFVAPQCANGYTSGTMGFA NTYGDVQIDCSNIHVGITKG LNDWNYPVSSESFSYTKTCS

SNGIFITYKNVPAGYRPFVD AYISATDVNSYTLSYANEYT CAGGYWQRAPFTLRWTGYRN

SDAGSNG.
                                                         (SEQ ID NO: 3)
B = IVIVATTRTVTDS       TTAVTTLPFDPNRDKTKTIE ILKPIPTTTITTSYVGVTTS

YSTKTAPIGETATVIVDIPY HTTTTVTSKWTGTITSTTTH TNPTDSIDTVIVQVP
```

Hyr1

```
                                                         (SEQ ID NO: 5)
C = TSRIDRGGIQGFHGDVKVHS GATWAILGTTLCSFFGGLEV EKGASLFIKSDNGPVLALNV

ALSTLVRPVINNGVISLNSK SSTSFSNFDIGGSSFTNNGE IYLDSSGLVKSTAYLYAREW

TNNGLIVAY
                                                         (SEQ ID NO: 6)
D = QNQKAAGNIAF         GTAYQTITNNGQICLRHQDF VPATKIKGTGCVTADEDTWI

KLGNTILSVEPTHNFYLKDS KSSLIVHAVSSNQTFTVHGF GNGNKLGLTLPLTGNRDHFR

FEYYPDTGILQLRADALPQY FKIGKGYDSKLFRIVNSRGL KNAVTYDGPVPNNEIPAVCL

IPCTNGPSAPESESDLNTPT TSSIET
```

X = is present or absent (-X), wherein X is a linker peptide.

```
        (SEQ ID NO: 11)          (SEQ ID NO: 12)
E1= A-B-X-C-D              E1(-X)= A-B-C-D (SEQ ID NO: 13)          (SEQ ID NO: 14)
E2= A-X-C-D                E2(-X)= A-C-D (SEQ ID NO: 15)          (SEQ ID NO: 16)
E3= A-X-D                  E3(-X)= A-D (SEQ ID NO: 17)          (SEQ ID NO: 18)
E4= C-D-X-A-B              E4(-X)= C-D-A-B (SEQ ID NO: 19)          (SEQ ID NO: 20)
E5= C-D-X-A                E5(-X)= C-D-A (SEQ ID NO: 21)          (SEQ ID NO: 22)
E6= D-X-A-B                E6(-X)= D-A-B (SEQ ID NO: 23)          (SEQ ID NO: 24)
E7= D-X-A                  E7(-X)= D-A
```

Als3

```
                                                         (SEQ ID NO: 2)
A = KTITGVFNSFNSLTWSNAAT YNYKGPGTPTWNAVLGWSLD GTSASPGDTFTLNMPCVFKF

TTSQTSVDLTAHGVKYATCQ FQAGEEFMTFSTLTCTVSNT LTPSIKALGTVTLPLAFNVG

GTGSSVDLEDSKCFTAGTNT VTFNDGGKKISINVDFERSN VDPKGYLTDSRVIPSLNKVS

TLFVAPQCANGYTSGTMGFA NTYGDVQIDCSNIHVGITKG LNDWNYPVSSESFSYTKTCS

SNGIFITYKNVPAGYRPFVD AYISATDVNSYTLSYANEYT CAGGYWQRAPFTLRWTGYRN

SDAGSNG
                                                         (SEQ ID NO 3)
B =          IVIVATTRTVTDS TTAVTTLPFDPNRDKTKTIE ILKPIPTTTITTSYVGVTTS

YSTKTAPIGETATVIVDIPY HTTTTVTSKWTGTITSTTTH TNPTDSIDTVIVQVP
```

Hyr1

```
                                                         (SEQ ID NO: 5)
C = TSRIDRGGIQGFHGDVKVHS GATWAILGTTLCSFFGGLEV EKGASLFIKSDNGPVLALNV

ALSTLVRPVINNGVISLNSK SSTSFSNFDIGGSSFTNNGE IYLDSSGLVKSTAYLYAREW

TNNGLIVAY
```

```
                                                    (SEQ ID NO: 6)
D =         QNQKAAGNIAF GTAYQTITNNGQICLRHQDF VPATKIKGTGCVTADEDTWI

KLGNTILSVEPTHNFYLKDS KSSLIVHAVSSNQTFTVHGF GNGNKLGLTLPLTGNRDHFR

FEYYPDTGILQLRADALPQY FKIGKGYDSKLFRIVNSRGL KNAVTYDGPVPNNEIPAVCL

IPCTNGPSAPESESDLNTPT TSSIET (SEQ ID NO: 10)
E =                   S SYSSAATESSVVS      ESSSAVDSLTSSSLSSKSES

SDVVSSTTNIESSSTAIETT MNSESSTDAGSSSISQSESS STAITSSSETSSSESMSASS

TTASNTSIETDSGIVSQSES SSNAL
```

X=is present or absent (-X), wherein X is a linker peptide.

```
         (SEQ ID NO: 11)         (SEQ ID NO: 12)
S1= A-B-X-C-D             S1(-X)= A-B-C-D (SEQ ID NO: 25)         (SEQ ID NO: 26)
S2= A-X-C-D-E             S2(-X)= A-C-D-E (SEQ ID NO: 27)         (SEQ ID NO: 28)
S3= A-X-D-E               S3(-X)= A-D-E (SEQ ID NO: 29)         (SEQ ID NO: 30)
S4= C-D-E-X-A-B           S4(-X)= C-D-E-A-B (SEQ ID NO: 17)         (SEQ ID NO: 18)
S5= C-D-X-A-B             S5(-X)= C-D-A-B (SEQ ID NO: 21)         (SEQ ID NO: 22)
S6= D-X-A-B               S6(-X)= D-A-B (SEQ ID NO: 23)         (SEQ ID NO: 24)
S7= D-X-A                 S7(-X)= D-A
```

In some instances, a modification to a polypeptide as described herein does not substantially reduce the biological activity, e.g., immunogenic activity, of the polypeptide. The modified polypeptide may have or may optimize a characteristic of a polypeptide, such as in vivo stability, bioavailability, toxicity, immunological activity, immunological identity, or conjugation properties.

Modifications include those by natural processes, such as posttranslational processing, or by chemical modification techniques known in the art. Modifications may occur anywhere in a polypeptide including the polypeptide backbone, the amino acid side chains, and the amino- or carboxy-terminus. The same type of modification may be present in the same or varying degrees at several sites in a given polypeptide, and a polypeptide may contain more than one type of modification.

A variant or otherwise modified polypeptide can also include one or more amino acid insertions, deletions, or substitutions, either conservative or non-conservative (e.g., D-amino acids, desamino acids) in the polypeptide sequence. For example, the addition of one or more cysteine residues to the amino or carboxy terminus of any of the polypeptides of the invention can facilitate conjugation of these polypeptides. Exemplary polypeptides having an N- or C-terminal cysteine.

Amino acid substitutions can be conservative (i.e., wherein a residue is replaced by another of the same general type or group) or non-conservative (i.e., wherein a residue is replaced by an amino acid of another type). In addition, a non-naturally occurring amino acid can be substituted for a naturally occurring amino acid (i.e., non-naturally occurring conservative amino acid substitution or a non-naturally occurring non-conservative amino acid substitution).

Polypeptides made synthetically, e.g., using methods known in the art, can include substitutions of amino acids not naturally encoded by DNA (e.g., non-naturally occurring or unnatural amino acid). Examples of non-naturally occurring amino acids include D-amino acids, an amino acid having an acetylaminomethyl group attached to a sulfur atom of a cysteine, a pegylated amino acid, the omega amino acids of the formula $NH_2(CH_2)_n COOH$ wherein n is 2-6, neutral nonpolar amino acids, such as sarcosine, t-butyl alanine, t-butyl glycine, N-methyl isoleucine, and norleucine. Phenylglycine may substitute for Trp, Tyr, or Phe; citrulline and methionine sulfoxide are neutral nonpolar, cysteic acid is acidic, and ornithine is basic. Proline may be substituted with hydroxyproline and retain the conformation conferring properties.

Variants may be generated by substitutional mutagenesis and retain or even increase the biological activity, e.g., immunogenic activity, of the original polypeptide.

The polypeptides described herein can be obtained, e.g., by chemical synthesis using a commercially available automated peptide synthesizer. The synthesized protein or polypeptide can be precipitated and further purified, for example by high performance liquid chromatography (HPLC). Alternatively, the proteins and polypeptides can be obtained by recombinant methods, e.g., that are well-known in the art.

Conjugates

Polypeptides of the invention may be conjugated to another moiety or particle.

Protein Moieties

In some instances, it may be useful to conjugate the polypeptide to a protein that is immunogenic in the species to be immunized, e.g., keyhole limpet hemocyanin (KLH), CRM197, tetanus toxoid, diptheria toxoid, serum albumin, bovine thyroglobulin, soybean trypsin inhibitor, or a polycation (poly-L-Lysine or poly-L-arginine), e.g., using a bifunctional or derivatizing agent as known in the art, for example, maleimidobenzoyl sulfosuccinimide ester (conjugation through cysteine residues), N-hydroxysuccinimide (through lysine residues), glutaraldehyde, or succinic anhydride.

In some instances, the conjugate may be a recombinant fusion protein, e.g., to facilitate expression and purification of the polypeptide.

Particles for Conjugation or Display of Polypeptides

In some instances, polypeptides are conjugated to or displayed on a particle, e.g., a phage, a yeast, a virus, a virosome, or a recombinant virus-like particle.

For example, one or more polypeptides may be conjugated to a phage, a yeast, or a virus particle, e.g., to the surface of the particle. In one embodiment, a nucleic acid molecule encoding the polypeptide is inserted into the phage, yeast, or virus particle, resulting in expression of the polypeptide in the phage, yeast, or virus, e.g., at the surface of the particle. The phage, yeast, or virus population containing the polypeptide may then be isolated and prepared, e.g., as a vaccine, by adding a pharmaceutically acceptable excipient.

In some embodiments, polypeptides as described herein are conjugated to a virosome or virus-like particle (VLP). Virosomes and VLPs generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. Viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p 1). Virosomes are discussed further in, e.g., Gluck et al. (2002), *Vaccine* 20:B10-B16, which is incorporated by reference in its entirety.

VLPs are discussed further, e.g., in Niikura et al. (2002), *Virology* 293:273-280; Lenz et al. (2001), *J Immunol* 166: 5346-5355; Pinto et al. (2003), *J Infect Dis* 188:327-338; Gerber et al. (2001), *Viral* 75:4752-4760; WO03/024480; and WO03/024481, each of which is incorporated by reference in its entirety.

Antibodies

The invention features monoclonal and polyclonal antibodies that bind to the polypeptides or conjugates described herein.

Monoclonal Antibodies

Monoclonal antibodies may be made, e.g., using the hybridoma method first described by Kohler et al., *Nature* 256:495, 1975, or may be made by recombinant DNA methods (see, e.g., U.S. Pat. No. 4,816,567). In the hybridoma method, a mouse or other appropriate host animal, such as a hamster or macaque monkey, is immunized, e.g., using a polypeptide or conjugate described herein, to elicit lymphocytes that produce or are capable of producing antibodies that will specifically bind to the polypeptide or conjugate used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103, Academic Press, 1986).

The hybridoma cells thus prepared are seeded and grown in a suitable culture medium that can contain one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Exemplary myeloma cells are those that fuse efficiently, support stable high-level production of antibody by the selected antibody-producing cells, and are sensitive to a medium such as HAT medium. Among these, particular myeloma cell lines that may be considered for use are murine myeloma lines, such as those derived from MOPC-21 and MPC-11 mouse tumors available from the Salk Institute Cell Distribution Center, San Diego, Calif., USA, and SP-2 or X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.* 133:3001, 1984; Brodeur et al., Monoclonal Antibody Production Techniques and Applications, pp. 51-63, Marcel Dekker, Inc., New York, 1987).

Culture medium in which hybridoma cells are growing is assayed for production of monoclonal antibodies directed against the antigen. The binding specificity of monoclonal antibodies produced by hybridoma cells can be determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, clones may be subcloned by limiting dilution procedures and grown by standard methods (Goding, Monoclonal Antibodies: Principles and Practice, pp. 59-103, Academic Press, 1986). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described, for example, in McCafferty et al., *Nature* 348:552-554, 1990.

Clackson et al., *Nature* 352:624-628, 1991 and Marks et al., *J. Mol. Biol.* 222:581-597, 1991, describe the isolation of murine and human antibodies, respectively, using phage libraries. Subsequent publications describe the production of high affinity (nM range) human antibodies by chain shuffling (Marks et al., *Bio/Technology* 10:779-783, 1992), as well as combinatorial infection and in vivo recombination as a strategy for constructing very large phage libraries (Waterhouse et al., *Nucl. Acids. Res.* 21:2265-2266, 1993). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison et al., *Proc. Natl. Acad. Sci. U.S.A.* 81:6851, 1984), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Polyclonal Antibodies

Polyclonal antibodies are typically raised in animals by multiple injections, e.g., subcutaneous or intraperitoneal injections, of the relevant antigen and an adjuvant. In some instances, it may be useful to conjugate the polypeptide to a protein that is immunogenic in the species to be immunized, e.g., keyhole limpet hemocyanin (KLH), CRM197, tetanus toxoid, diptheria toxoid, serum albumin, bovine thyroglobulin, soybean trypsin inhibitor, or a polycation (poly-L-Lysine or poly-L-arginine), e.g., using a bifunctional or derivatizing agent as known in the art, for example, maleimidobenzoyl sulfosuccinimide ester (conjugation through cysteine residues), N-hydroxysuccinimide (through lysine residues), glutaraldehyde, or succinic anhydride.

Vaccines and Antibody-Containing Pharmaceutical Compositions

Formulations for vaccines and antibody-containing pharmaceutical compositions (collectively "compositions") as described herein can be prepared using standard pharmaceutical formulation chemistries and methodologies that are readily available to the reasonably skilled artisan. For example, polypeptides, conjugates, or antibodies as described herein can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions may include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e.g., sterile pyrogen-free water) prior to parenteral administration of the reconstituted composition. The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions that are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Alternatively, the polypeptides, conjugates, and antibodies described herein may be encapsulated, adsorbed to, or associated with particulate carriers. Suitable particulate carriers include those derived from polymethyl methacrylate polymers, as well as PLG microparticles derived from poly(lactides) and poly(lactide-co-glycolides). See, e.g., Jeffery et al. (1993) Pharm. Res. 10:362-368. Other particulate systems and polymers can also be used, for example, polymers such as polylysine, polyarginine, polyornithine, spermine, spermidine, as well as conjugates of these molecules.

The formulated compositions will include an amount of one or more polypeptides or conjugates described herein that is sufficient to mount an immunological response. An immunogenic amount can be readily determined by one of skill in the art. Such an amount will fall in a relatively broad range that can be determined through routine trials. The compositions may contain from about 0.1% to about 99.9% of the polypeptides, conjugates, or antibodies, and can be administered directly to the subject or, alternatively, delivered ex vivo, to cells derived from the subject, using methods known to those skilled in the art.

Compositions can include a mixture of distinct polypeptides, conjugates, or antibodies as described herein. For example, vaccines may include, e.g., 2, 3, 4, 5, 6, 7, 8, or more distinct polypeptides or conjugates as described herein, e.g., containing or consisting of the amino acid sequences disclosed herein, or a variant sequence thereof having up to three substitutions, deletions, or additions to the amino acid sequence of any one of amino acid sequences disclosed herein. In one embodiment, a vaccine includes eight distinct polypeptides, wherein the amino acid sequence of the eight polypeptides consist of the sequence of the amino acid sequences disclosed herein. In another embodiment, antibody-containing pharmaceutical compositions may include a mixture of monoclonal or polyclonal antibodies, e.g., having distinct specificities to polypeptides or conjugates as described herein.

Substances that stimulate the immune response, e.g., adjuvants, may be included in the compositions, e.g., in vaccines. Examples of chemical compounds used as adjuvants include, but are not limited to, aluminum compounds (e.g., alum, Alhydrogel), oils, block polymers, immune stimulating complexes, vitamins and minerals (e.g., vitamin E, vitamin A, selenium, and vitamin B12), Quil A (saponins), bacterial and fungal cell wall components (e.g., lipopolysaccarides, lipoproteins, and glycoproteins), hormones, cytokines, and co-stimulatory factors.

Methods of Treatment

The invention features methods of vaccinating a mammal against candidiasis including administering to the animal a vaccine as described herein, thereby vaccinating the mammal against candidiasis. Additionally, the invention features methods of passive immunization of a mammal against candidiasis including administering to the mammal an effective amount of a pharmaceutical composition as described herein, thereby passively immunizing the mammal against candidiasis. Candidiasis may include, e.g., disseminated candidiasis, e.g., hematogenously disseminated candidiasis, or mucosal candidiasis. In some instances, the candidiasis is caused, e.g., by *Candida albicans, Candida glabrata, Candida krusei, Candida parapsilosis,* or *Candida tropicalis*. Other *Candida* species include *Candida lusitaniae* and *Candida stellatoidea*.

Additionally, the compositions and methods described herein may be used, e.g., to vaccinate a human at risk for the development of a *S. aureus* systemic infection or a skin or soft tissue infection against *S. aureus*. First, a human at risk for the development of a *S. aureus* infection or a *S. aureus* SSSI is identified. Second, the human is administered an immunogenic amount of a vaccine comprising a polypeptide described herein, in a pharmaceutically acceptable medium with or without an adjuvant. For example, the human is administered between one and three doses of a polypeptide disclosed herein containing between 3 and 1000 µg of the polypeptide per dose, with multiple doses occurring at intervals of two weeks to six months.

It is expected that, following administration of the vaccine, the human is at decreased risk for the development of a *S. aureus* infection or an *S. aureus* SSSI for a period lasting from one month to several years or more.

Likewise, a human who is identified as having an *S. aureus* infection or an *S. aureus* SSSI may be treated by administration of an immunogenic amount of a pharmaceutical composition comprising a Peptide 1 in a pharmaceutically acceptable medium with or without an adjuvant. For example, the human is administered between one and three doses of a polypeptide disclosed herein containing between 3 and 1000 µg of the polypeptide per dose, with multiple doses occurring at intervals of two weeks to six months.

Again, it is expected that, following administration of the pharmaceutical composition, the *S. aureus* SSSI of the human is decreased in severity.

The compositions and methods described herein may be used, e.g., to vaccinate a bovine species at risk for the development of a systemic *S. aureus* infection or even *S. aureus* skin or soft tissue infection against *Staphylococcus aureus*. In particular, the bovine species may be at risk of developing bovine mastitis caused by *S. aureus*. First, a bovine species at risk for the development of an *S. aureus* SSSI, e.g., bovine mastitis, is identified. For example, any milk-producing bovine may be considered to be at risk of developing bovine mastitis caused by *S. aureus*. Second, the bovine species is administered an immunogenic amount of a vaccine comprising one or more of the polypeptides disclosed herein in a pharmaceutically acceptable medium with or without an adjuvant. For example, the bovine species is administered between one and three doses of a polypeptide disclosed herein containing between 3 and 1000 µg of the polypeptide per dose, with multiple doses occurring at intervals of two weeks to six months.

It is expected that, following administration of the vaccine, the bovine species is at decreased risk for the development of an *S. aureus* SSSI, e.g., bovine mastitis.

Likewise, a bovine species identified as having an *S. aureus* SSSI, e.g., bovine mastitis, may be treated by administration of an immunogenic amount of a pharmaceutical composition comprising one or more polypeptides disclosed herein in a pharmaceutically acceptable medium with or without an adjuvant. For example, the bovine species is administered between one and three doses of the polypeptide containing between 3 and 1000 µg of the polypeptide per dose, with multiple doses occurring at intervals of two weeks to six months.

It is expected that, following administration of the pharmaceutical composition, the *S. aureus* SSSI, e.g., bovine mastitis, of the bovine species is decreased in severity.

Vaccines and antibody-containing pharmaceutical compositions (collectively "compositions") as described herein can be administered prophylactically or therapeutically on their own or in combination with other art-known compositions that induce protective responses against pathogens (e.g., viral, bacterial, fungal, or parasitic pathogens), tumors or cancers, allergens, autoimmune disorders, or graft rejection. For example, the compositions can be administered simultaneously, separately, or sequentially, e.g., with another immunization vaccine, such as a vaccine for, e.g., influenza, malaria, tuberculosis, smallpox, measles, rubella, mumps, or any other vaccines known in the art.

Compositions as described herein can be delivered to a mammalian subject (e.g., a human or other mammal described herein) using a variety of known routes and techniques. For example, a composition can be provided as an injectable solution, suspension, or emulsion, and administered via intramuscular, subcutaneous, intradermal, intracavity, parenteral, epidermal, intraarterial, intraperitoneal, or intravenous injection using a conventional needle and syringe, or using a liquid jet injection system. Compositions can also be administered topically to skin or mucosal tissue, such as nasally, intratracheally, intestinal, rectally or vaginally, or provided as a finely divided spray suitable for respiratory or pulmonary administration. Other modes of administration include oral administration, suppositories, and active or passive transdermal delivery techniques.

The compositions described herein can be administered to a mammalian subject (e.g., a human or other mammal described herein) in an amount that is compatible with the dosage formulation and that will be prophylactically and/or therapeutically effective. An appropriate effective amount will fall in a relatively broad range but can be readily determined by one of skill in the art by routine trials. The "Physicians Desk Reference" and "Goodman and Gilman's The Pharmacological Basis of Therapeutics" are useful for the purpose of determining the amount needed.

Prophylaxis or therapy can be accomplished by a single direct administration at a single time point or by multiple administrations, optionally at multiple time points. Administration can also be delivered to a single or to multiple sites. Those skilled in the art can adjust the dosage and concentration to suit the particular route of delivery. In one embodiment, a single dose is administered on a single occasion. In an alternative embodiment, a number of doses are administered to a subject on the same occasion but, for example, at different sites. In a further embodiment, multiple doses are administered on multiple occasions. Such multiple doses may be administered in batches, i.e. with multiple administrations at different sites on the same occasion, or may be administered individually, with one administration on each of multiple occasions (optionally at multiple sites). Any combination of such administration regimes may be used.

In one embodiment, different compositions of the invention may be administered at different sites or on different occasions as part of the same treatment regime.

Different administrations may be performed on the same occasion, on the same day, one, two, three, four, five or six days apart, or one, two, three, four or more weeks apart. In some instances, administrations are 1 to 5 weeks apart, e.g., 2 to 4 weeks apart, such as 2 weeks, 3 weeks or 4 weeks apart. The schedule and timing of such multiple administrations can be optimised for a particular vaccine or pharmaceutical composition by one of skill in the art by routine trials.

Dosages

An adequate dose of the vaccines or antibody-containing pharmaceutical compositions described herein may vary depending on such factors as preparation method, administration method, age, body weight and sex of the patient, severity of symptoms, administration time, administration route, rate of excretion, and responsivity. A physician of ordinary skill in the art will easily determine and diagnose the administration dose effective for treatment.

Compositions may be prepared into unit-dose or multiple-dose preparations by those skilled in the art using a pharmaceutically acceptable carrier and/or excipient according to a method known in the art.

Vectors

The invention also provides vectors containing the nucleic acids encoding the polypeptides disclosed herein. Suitable expression vectors are well-known in the art and include vectors capable of expressing a nucleic acid operatively linked to a regulatory sequence or element such as a promoter region or enhancer region that is capable of regulating expression of the nucleic acid. Appropriate expression vectors include vectors that are replicable in eukaryotic cells and/or prokaryotic cells and vectors that remain episomal or integrate into the host cell genome.

The terms "vector", "cloning vector" and "expression vector" mean the vehicle by which a nucleic acid can be introduced into a host cell. The vector can be used for propagation or harboring a nucleic acid or for polypeptide expression of an encoded sequence. A wide variety of vectors are known in the art and include, for example, plasmids, phages and viruses. Exemplary vectors can be found described in, for example, Sambrook et al., "Molecular Cloning: A Laboratory Manual," 3$^{rd}$ Edition. Cold Spring Harbor Laboratories, Cold Spring Harbor, N.Y., 2001; and Ausubel et al., "Current Protocols in Molecular Biology," John Wiley and Sons, Baltimore, Md. (1999)).

Promoters or enhancers, depending upon the nature of the regulation, can be constitutive or regulated. The regulatory sequences or regulatory elements are operatively linked to a nucleic acid of the invention such that the physical and functional relationship between the nucleic acid and the regulatory sequence allows transcription of the nucleic acid.

Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like. The vectors of the invention are useful for subcloning and amplifying a nucleic acid molecule and for recombinantly expressing a polypeptide as disclosed herein. A vector of the invention can include, for example, viral vectors such as a bacteriophage, a baculovirus or a retrovirus; cosmids or plasmids; and, particularly for cloning large nucleic acid molecules, bacterial artificial chromosome vectors (BACs) and yeast artificial chromosome vectors (YACs). Such vectors are commercially available, and their uses are well known in the art. One skilled in the art will know or can readily determine an appropriate promoter for expression in a particular host cell.

The invention additionally provides recombinant cells containing nucleic acids of the invention. The recombinant cells are generated by introducing into a host cell a vector containing a nucleic acid molecule. The recombinant cells are transducted, transfected or otherwise genetically modified. Exemplary host cells that can be used to express recombinant molecules include mammalian primary cells; established mammalian cell lines, such as COS, CHO, HeLa, NIH3T3, HEK 293 and PC12 cells; amphibian cells, such as *Xenopus* embryos and oocytes; and other vertebrate cells. Exemplary host cells also include insect cells such as *Drosophila*, yeast cells such as *Saccharomyces cerevisiae*, *Saccharomyces pombe*, or *Pichia pastoris*, and prokaryotic cells such as *Escherichia coli*.

Embodiments of the present invention also provide specific Als3 or Hyr1 polypeptides or Als3/Hyr1 polypeptides that can act as antigens for generating an immune response to *Candida*, gram negative bacteria including bacteria of the *Acinetobacter* genus, for example, *Acinetobacter baumannii*, as well as a staphylococcal bacterium.

In some aspects of the invention, the polypeptides of the invention include substantially the same amino acid sequence set forth in any one of the amino acid sequences described herein. For example, the amino acid sequence can have at least 65%, 70%, 75%, 80%, 85%, 90%, 95%, 98% or 99% sequence identity to any one of SEQ ID NOS: 1-33. In other aspects, such polypeptides are immunogenic and capable of eliciting production of an anti-Als3 antibody, anti-HYR1 antibody, and Als3/Hyr1 antibody or immunogenic response in a subject.

As described herein, the polypeptides of the invention can encompass substantially similar amino acid sequences having at least about 65% identity with respect to the reference amino acid sequence, and retaining comparable functional and biological activity characteristic of the reference amino acid sequence. In one aspect, polypeptides having substantially the same amino acid sequence will have at least 50% or 60% identity, at least 65% identity, at least 70% identity, at least 75% identity, at least 80% identity, at least 85% identity, at least 90% identity, at least 95% identity, at least 98% identity, or at least 99% identity. It is recognized, however, that polypeptides, or encoding nucleic acids, containing less than the described levels of sequence identity arising as splice variants or that are modified by conservative amino acid substitutions, or by substitution of degenerate codons are also encompassed within the scope of the present invention.

Assessment

The following examples are intended to illustrate the invention. These are not meant to limit the invention in any way.

Methods and Materials for Evaluating Treatment of Candidiasis

*Candida* Strains and Growth Conditions

*C. albicans* 15663, *C. glabrata* 31028, *C. parapsilosis* 22019 and *C. tropicalis* 4243 are clinical bloodstream isolates collected from Harbor-UCLA Medical Center. *C. krusei* 91-1159 was generously provided by Michael Rinaldi, San Antonio, Tex. *C. albicans* strains CAAH-31 and THE31 are as described in the literature. All tested strains were routinely grown in YPD (2% Bacto Peptone, 1% yeast extract, 2% dextrose). Cell densities were determined by counting in a hemacytometer.

Recombinant Polypeptides and Rabbit Polyclonal Antibodies

Recombinant polypeptides are generated according to standard methods. To generate antibodies, the peptides may be purified and conjugated to keyhole limpet hemocyanin (KLH) before raising rabbit antiserum individually using a standard immunization protocol. Total IgG from pooled serum is affinity purified using Pierce Protein A plus Agarose (Thermo Scientific, Rockford, Ill.) prior to administering in passive immunization studies.

Immunization Protocol and Animal Studies

All active vaccinations are conducted according to standard methods. In brief, juvenile (10-12 week) Balb/C mice are vaccinated subcutaneously with 30 µg of a polypeptide mixed with alum (2% Alhydrogel; Brenntag Biosector, Frederikssund, Denmark) as an adjuvant in phosphate buffered saline (PBS) on day 0, boosted with the same dose on day 21, then infected via the tail vein on day 35. Control mice are vaccinated with alum alone.

To test the efficacy of the vaccine in immunocompromised mice, mice are vaccinated as above prior to inducing neutropenia by intraperitoneal injection of 200 mg/kg of cyclophosphamide on day −2 followed by another dose of 100 mg/kg on day +7 relative to infection. This regimen results in approximately 10 days of leucopenia with reduction in neutrophil, lymphocyte and monocyte counts according to standard methods. For both immunocompetent and neutropenic mice differences in survival between vaccinated and adjuvant vaccinated mice are compared by the Log Rank test.

For passive immunization, immune IgG is administered intraperitoneally to naïve mice 2 h before infecting i.v. with *C. albicans*. Control mice are given isotype matching IgG (Innovative Research, USA). IgG doses are repeated 3 days after infection, and survival of mice was monitored twice daily.

Quantitative culturing of kidneys from vaccinated or control mice to be infected with different species of *Candida* is performed according to standard methods. In brief, mice are infected through tail veins. Kidneys are harvested 3 day post infection, homogenized, serially diluted in 0.85% saline, and quantitatively cultured on YPD that contained 50 µg/mL chloramphenicol. Colonies are counted after incubation of the plates at 37° C. for 24 to 48 h, and results are expressed as log CFU per gram of infected organ.

Concomitant with the fungal burden experiment, kidneys are removed aseptically from two mice per group for histopathological examination. Kidneys are immersed in zinc formalin fixative until examination. Fixed organs are dehydrated in graded alcohol solutions, embedded in paraffin, and cut into 6-µm-thick sections. Mounted sections are stained with Gomori methenamine silver and examined by light microscopy (Davis et al. (2000) Infect Immun 68: 5953-5959).

Enzyme-Linked Immunosorbent Assay (ELISA)

To test if a polypeptide induces an immune response, antibody titers of serum samples are collected from vaccinated and control mice are determined by ELISA in 96-well plates as previously described (Ibrahim et al. (2005) Infect Immun 73: 999-1005). Wells are coated at 100 µl per well with a peptide (e.g., one of more of peptide 2-11) at 5 µg/ml in PBS. Mouse sera are incubated for 1 h at room temperature following a blocking step with Tris-buffered saline (TBS; 0.01 M Tris HCl [pH 7.4], 0.15 M NaCl) containing 3% bovine serum albumin. The wells are then washed three times with TBS containing 0.05% Tween 20, followed by another three washes with TBS. Goat anti-mouse secondary antibody conjugated with horseradish peroxidase (Sigma) is added at a final dilution of 1:5000, and the plate is further incubated for 1 h at room temperature. Wells are then washed with TBS and incubated with substrate containing 0.1 M citrate buffer (pH 5.0), 50 mg of o-phenylenediamine (Sigma), and 10 µl of 30% $H_2O_2$. The color is allowed to develop for 30 min, after which the reaction is terminated by addition of 10% $H_2SO_4$ and the optical density (OD) at 490 nm is determined in a microtiter plate reader. Negative control wells received only diluent, and background absorbance is subtracted from the test wells to obtain final OD readings. The ELISA titer is taken as the reciprocal of the last serum dilution that gave a positive OD reading (i.e., more than the mean OD of negative control samples plus 2 standard deviations).

$F(ab')_2$ Blocking Assay

To study the mechanism of protection mediated by anti-polypeptides (e.g., one described herein) antibodies in phagocyte-mediated killing of *C. albicans*, HL-60 cells that have been differentiated to neutrophil-like phenotype are employed (Luo et al., (2010) J Infect Dis 201: 1718-1728). A killing assay is conducted in the presence of anti-peptide IgG or $F(ab')_2$ fragments as described before (Luo (2010) J Infect Dis 201: 1718-1728). In brief, HL-60 cells are induced with 2.5 µM of retinoic acid and 1.3% DMSO for three days at 37° C. with 5% $CO_2$. Immune anti-Als3 or anti-Hyr1 or anti-Als3/Hyr1 polypeptide sera are, if desired, pooled and total IgG is isolated using protein A agarose (Thermo Scientific). Serum collected from the same rabbits prior to immunization with the polypeptides serves as control serum. The $F(ab')_2$ fragments from immune or control IgG is purified with Pierce $F(ab')_2$ Preparation Kit according to the manufacturer's instruction. SDS-PAGE analysis is utilized to indicate >95% of Fc fragment is digested. Next, *C. albicans* cells overexpressing or suppressing Als3 is incubated with 50 µg/ml of vaccinated or control $F(ab')_2$ fragments on ice for 45 min. *C. albicans* cocultured with the $F(ab')_2$ fragments is incubated with HL-60 derived neutrophils for 1 h at 37° C. with 5% $CO_2$ prior to sonication and quantitative culturing on YPD plates. % killing is calculated by dividing the number of CFU after coculturing with HL-60 derived neutrophils by the number of CFU from *C. albicans* incubated with media without neutrophil-like cells.

Statistical Analysis

The nonparametric log rank test is used to determine differences in the survival times of the mice. Neutrophil killing assay, titers of antibody, and tissue fungal burden is compared by the Mann-Whitney U test for unpaired comparisons. Correlations are calculated with the Spearman rank sum test. P values of <0.05 are considered significant.

Expected Results

Peptides that significantly improved survival and decreased fungal burden in immunocompetent mice challenged i.v. with *C. albicans* are taken as being useful in the invention. Similarly, polypeptides that statistically protect immunocompromised mice against candidiasis are useful in the invention. Mice protected from fungal infection after receiving purified IgG targeting a polypeptide disclosed herein in a dose specific manner are not only taken as an indication of the usefulness of passive immunization strategies for treating candidiasis but also for the usefulness of the polypeptide antigen used to raise an immune response. Polypeptide vaccines that substantially reduce tissue fungal burden in BALB/c mice challenged with several non-*albicans* species of *Candida* are likewise taken as being useful in the invention.

Methods and Materials for Evaluating Treatment of an *Acinetobacter* Infection

Recombinant polypeptides disclosed herein are produces according to standard methods, for example, using *E. coli* expression system. The recombinant polypeptide is then used to actively vaccinate mice. Mice, for example, are immunized with aluminum hydroxide alone or the recombinant polypeptide mixed with aluminum hydroxide (n=9) on day 0, and boosted on day 21. The vaccinated mice are subsequently infected with *A. baumannii* on day 35. Polypeptide vaccines providing statistically significant survival compared to control mice are taken as useful in the invention. Additionally, measurement of bacterial burden in the tissue of mice vaccinated and infected similarly are examined. The bacterial burden as measured by the number of colony forming units per gram of tissue showing that tissue isolates from kidney, lung and spleen have a lower bacterial burden as compared to control tissue samples are also taken as indicative of useful polypeptide vaccines.

In another working example, overall passive immunization against *Acinetobacter baumannii* infection may also be assayed in diabetic mice. Purified IgG from the eight different polyclonal antibodies are given to diabetic mice 2 hours prior to infection. Commercially available unrelated rabbit IgG is given to diabetic control mice. The mice are then infected with a lethal dose of *Acinetobacter baumannii* via tail vein injection. Mice identified as significantly surviving longer after receiving a single dose of the appropriate IgG than mice receiving the control IgG (e.g., ~80% survival in the anti-polypeptide IgG vs. 0% in the control arm, p<0.0001 by Log Rank test) are taken as evidence of the effectiveness of the polypeptide antigen.

Methods and Materials for Evaluating Treatment of a Staphylococcal Infection

Briefly, to determine whether a polypeptide described herein protects against *S. aureus*, female Balb/c mice are vaccinated with complete Freund's Adjuvant according to standard methods with a regimen on day 0, followed by a booster dose in Incomplete Freund's Adjuvant at 3 weeks. Two weeks following vaccination, mice are infected via the tail-vein with a lethal dose of *S. aureus* strain 67-0, which is methicillin-resistant and is known to be virulent in animal models. Polypeptides mediating improved long-term survival in these infected mice are taken as being useful in the invention.

Polypeptides may also be tested in the following murine model of skin or soft tissue infection. Polypeptide vaccination is evaluated across a dose range using a regimen of alhydrogel adjuvant. Doses of 3, 10, 30, 100, or 300 µg (IM) are studied in parallel. Primary vaccination (day 0) is followed by an identical boost on study day 21. Mice are infected with *S. aureus* 14 days after boost (study day 35). A subcutaneous skin/soft tissue abscess model is modified from Ding et al. (*J. Bacteriol.* 2008 190:7123-9) and/or Voyich et al. (*J. Infect. Dis.* 2006 194:1761-1770) for these studies. On study day 35, mice are anesthesized, flanks were shaved and sterilized, and 2×107 CFU inocula (without beads or matrix) is introduced into the subcutaneous compartment by injection (100 µl). A minimum of 20 mice per control or vaccine-regimen groups is used in each study. Abscess area/volume is then measured in each mouse flank during the study period up to 14 days post-challenge. To do so, mice are anesthetized, and the lesion site length (l) and width (w) is assessed to quantify abscess or dermonecrosis area (cm2). Abscess volume ($cm^3$) is calculated per the formula for a spherical ellipsoid: [v=(n/6)×l×w2]. For quantitative culture analyses, at pre-selected times post-infection, mice were humanely sacrificed and processed for quantitative culture of abscesses. Each flank are aseptically dissected, the abscess removed and prepared for culture. Abscesses are individually homogenized, and serially diluted in sterile PBS for quantitative culture onto sheep blood agar plates. Cultures are incubated (37° C.) for 24 hours, and resulting colonies enumerated. For statistical analyses, differences in experimental results are compared based on power estimates indicating that 16-20 mice per group yields >85% power to detect 1 log difference in CFU per gram tissue, or 2 mm abscess area (a=0.05; Mann-Whitney U test. P values are defined according to standard methods.

Expected Results

Polypeptide vaccines that significantly reduce the abscess area, volume, or CFU densities in the murine model of MRSA skin or soft tissues assay are taken as being useful in the invention. Such results are taken to indicate that the polypeptide vaccine tested is useful as a means to prevent or mitigate MRSA skin infection or abscesses or both in mammals.

Additional Assessment Utilizing Human PMBCs

Useful polypeptide antigens described herein are also identified using standard human PMBCs. PMBCs are obtained from individuals vaccinated using an Als3 or Hyr1 at various time points following vaccination. Collected PMBCs are stored at −80° C. and thawed before use.

For an assay, ELISpot plates coated with antibodies to specific human cytokines or chemokines, e.g. IFN-γ, IL-17A, IL-4, or GRO are used. PBMC samples are then activated in culture for 48 h and are distributed in 96-well ELISpot plates at 200,000 cells per well. Specific polypeptides and/or combinations of polypeptides are added to triplicate wells and incubated for 48-96 h and then the supernatants from each well are removed for analysis. The ELISpot plates are developed to reveal the spot forming units per well reflecting the number or cells in the well that produce the compound of interest. Peptides or combination of peptides having an increase in cytokine or chemokine production relative to unstimulated PMBCs are taken as being useful in the invention.

Other Embodiments

All publications, patents, and patent applications mentioned in the above specification are hereby incorporated by reference. Various modifications and variations of the described methods of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A composition comprising an isolated polypeptide consisting of an amino acid sequence having at least 95% sequence identity to SEQ ID NO: 6 over the entire length of SEQ ID NO: 6 and a pharmaceutically acceptable carrier, diluent, and/or excipient.

2. The composition of claim 1, further comprising an adjuvant.

3. The composition of claim 2, wherein the adjuvant is Alhydrogel.

4. A method of inducing an immune response in a mammal comprising administering the composition of claim 1 to said mammal, wherein said composition induces an immune response against said polypeptide in said mammal.

5. The method of claim 4, wherein the mammal is administered a single dose or a plurality of doses of said composition.

6. The method of claim 5, wherein said composition is administered at least one day apart or at least two weeks apart.

7. The method of claim 4, wherein said mammal is a human.

8. The method of claim 4, wherein the composition is administered by intramuscular, subcutaneous, or intradermal administration.

9. The method of claim 4 further comprising administering a booster dose of the composition.

10. The composition of claim 1, wherein the amino acid sequence of the polypeptide consists of at least 97% sequence identity to SEQ ID NO: 6 over the entire length of SEQ ID NO: 6.

11. The composition of claim 10, wherein the amino acid sequence of the polypeptide consists of at least 99% sequence identity to SEQ ID NO: 6 over the entire length of SEQ ID NO: 6.

12. The composition of claim 11, wherein the amino acid sequence of the polypeptide consists of the amino acid sequence of SEQ ID NO: 6.

\* \* \* \* \*